United States Patent
Fixler et al.

(10) Patent No.: US 10,335,041 B2
(45) Date of Patent: Jul. 2, 2019

(54) NON-INVASIVE METHOD AND SYSTEM FOR DETECTION OF CANCER OR ARTERIAL VASCULAR DISORDERS USING METAL NANOPARTICLES

(71) Applicant: BAR ILAN UNIVERSITY, Ramat Gan (IL)

(72) Inventors: Dror Fixler, Ganey Tikva (IL); Rinat Ankri, Netanya (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 1088 days.

(21) Appl. No.: 14/668,353

(22) Filed: Mar. 25, 2015

(65) Prior Publication Data

US 2015/0196200 A1 Jul. 16, 2015

Related U.S. Application Data

(63) Continuation-in-part of application No. 14/149,925, filed on Jan. 8, 2014, now abandoned.

(Continued)

(51) Int. Cl.
*A61B 5/00* (2006.01)
*A61K 41/00* (2006.01)
(Continued)

(52) U.S. Cl.
CPC ........ *A61B 5/02007* (2013.01); *A61B 5/0075* (2013.01); *A61K 49/0423* (2013.01); *B82Y 15/00* (2013.01); *A61B 5/418* (2013.01); *A61B 90/39* (2016.02); *B82Y 20/00* (2013.01); *G01N 2800/323* (2013.01); *G02B 1/11* (2013.01); *G02B 1/113* (2013.01)

(58) Field of Classification Search
CPC .......................... A61B 5/0075; A61K 49/0423
See application file for complete search history.

(56) References Cited

U.S. PATENT DOCUMENTS

2006/0063995 A1* 3/2006 Yodh .................... A61B 5/0059
600/323
2009/0117606 A1 5/2009 Tunnell
(Continued)

OTHER PUBLICATIONS

Rinat Ankri et al; "A new method for cancer detection based on diffusion reflection measurements of targeted gold nanorods" International Journal of Nanomedicine 7:449-455. (2012).
(Continued)

*Primary Examiner* — Baisakhi Roy
(74) *Attorney, Agent, or Firm* — Symbus Law Group, LLC; Clifford D. Hyra

(57) ABSTRACT

Non-invasive methods and systems for detection of cancer or arterial vascular disorder involving administering to an individual a composition comprising noble metal nanoparticles that accumulate in a cancerous or injured vascular tissue; optically irradiating an area of a tissue suspected of being a cancerous or injured vascular tissue with a light source outputting an optical signal of at least one wavelength; and measuring diffusion reflection of the area of the irradiated tissue using at least one detector, whereby detection from the measured diffusion reflection of accumulation of the noble metal nanoparticles in this area indicates that the irradiated tissue is a cancerous or injured vascular tissue.

21 Claims, 25 Drawing Sheets

Related U.S. Application Data

(60) Provisional application No. 61/749,939, filed on Jan. 8, 2013, provisional application No. 61/969,901, filed on Mar. 25, 2014.

(51) Int. Cl.

| | | |
|---|---|---|
| *A61B 5/02* | (2006.01) | |
| *B82Y 15/00* | (2011.01) | |
| *A61K 49/04* | (2006.01) | |
| *G02B 1/113* | (2015.01) | |
| *B82Y 20/00* | (2011.01) | |
| *G02B 1/11* | (2015.01) | |
| *A61B 90/00* | (2016.01) | |

(56) References Cited

U.S. PATENT DOCUMENTS

2011/0236596 A1   9/2011  Skorb
2013/0115295 A1*  5/2013  Wang .................. A61K 41/0057
                                                      424/491

OTHER PUBLICATIONS

Rinat Ankri et al; "In-vivo tumor detection using diffusion reflection measurements of targeted gold nanorods—a quantitative study" Journal of Biophotonics 5:3:263-273 .(2012).
Rinat Ankri et al; "Intercoupling surface plasmon resonance and diffusion reflection measurements for real-time cancer detection" Journal of Biophotonics 6:2:188-196. (2013).
J. Baselga ; "The EGFR as a target for anticancer therapy—focus on cetuximab" European Journal of Cancer 37: S16-S22. (2001).
Irving J. Bigio et al; "Diagnosis of breast cancer using elastic-scattering spectroscopy: preliminary clinical results" Journal of Biomedical Optics 5:2:221-228 .(2000).
Robert F. Bonner et al "A random walk theory of time-resolved optical absorption spectroscopy in tissue" Photon Migration in Tissues, 11-23. (1989).
Albert E. Cerussi et al; "Diffuse optical spectroscopic imaging correlates with final pathological response in breast cancer neoadjuvant chemotherapy" Philosophical transactions of the Royal Society 369:4512-4530. (2011).
Rinaldo Cubeddn et al; "A solid tissue phantom for photon migration studies" Physics in medicine and biology 42: 1971-1979. (1997).
Leonarodo Dagdug et al; "Effects of anisotropic optical properties on photon migration in structured tissues" Physics in medicine and biology 48:1361-1370. (2003).
Jan S. Dam et al; "Fiber-optic probe for noninvasive real-time determination of tissue optical properties at multiple wavelengths" Applied optics 40,:7:1155-1164. (2001).
Bruce T. Draine et al; "User Guide for the Discrete Dipole Approximation Code DDSCAT 7.0" (2009).
J W Feather et al; "A portable reflectometer for the rapid quantification of cutaneous haemoglobin and melanin" Physics in medicine and biology 33:6:711-722. (1988).
Andre M. Gobinet al; "Near-Infrared Resonant Nanoshells for Combined Optical Imaging and Photothermal Cancer Therapy" Nano Letters 7:7:1929-1934. (2007).
Andreas H. Hielscher et al; "Influence of particle size and concentration on the diffuse backscattering of polarized light from tissue phantoms and biological cell suspensions" Applied Optics 36:1:125-135. (1997).
Xiaohua Huang et al; "Cancer Cell Imaging and Photothermal Therapy in the Near-Infrared Region by Using Gold Nanorods" Journal of American Chemical Society 128:2115-2120. (2006).
Steven L. Jacques et al: "Tutorial on diffuse light transport" Journal of Biomedical Optics 13:4: 041302-19.(2008).
Surbhin Lal et al; "Nanoshell-Enabled Photothermal Cancer Therapy: Impending Clinical Impact" Accounts of chemical research 41:12:1842-1851.(2008).
Alexander J Lin et al; "Spatial Frequency Domain Imaging of Intrinsic Optical Property Contrast in a Mouse Model Df Alzheimer's Disease" Annals of Biomedical Engineering, 39:4:1349-1357. (2011).
Amanda R Lowery et al; "Immunonanoshells for targeted photothermal ablation of tumor cells" International Journal of Nanomedicine 1:2:149-154. (2006).
Srivalleesha Mallidi et al; "Multiwavelength Photoacoustic Imaging and Plasmon Resonance Coupling of Gold Nanoparticles for Selective Detection of Cancer" Nano Letters 9:8:2825-2831. (2009).
Babak Nikoobakht et al; "Preparation and Growth Mechanism of Gold Nanorods (NRs) Using Seed-Mediated Growth Method" Chemistry of materials 15:1957-1962. (2003).
Tuan H. Pham. H. et al; "Broad bandwidth frequency domain instrument for quantitative tissue optical spectroscopy" Review of scientific instruments 71, No. 6.:500-2513. (2000).
Tobi Reuveni et al; "Targeted gold nanoparticles enable molecular CT imaging of cancer: an in vivo study" International Journal of Nanomedicine 6 :2859-2864. (2011).
J. M. Schmitt et al; "Multilayer model of photon diffusion in skin" The Journal of the Optical Society of America A 7 :141-2153. (1990)
M Shimada et al; "Estimation of the absorption coefficients of two-layered media by a simple method using spatially and time-resolved reflectances" Physics in medicine and biology 54:5057-5071. (2009).
P. Stanton et al; "Epidermal growth factor receptor expression by human squamous cell carcinomas of the head and neck, cell lines and xenografts" British journal of cancer 70:427-433. (1994).
Bruce J. Tromberg; "Non-invasive measurements of breast tissue optical properties using frequency-domain photon migration" Philosophical Transactions of the Royal Society B 352:661-668. (1997).
Yuanglong Yang et al; "UV Reflectance Spectroscopy Probes DNA and Protein Changes in Human Breast Tissues" Journal of Clinical Laser Medicine & Surgery 19:1:35-39. (2001).
Giovanni Zaccanti et al; "Method for measuring the mean time of flight spent by photons inside a volume element of a highly diffusing medium" Optis Letters 24:18:1290-1292. (1999).
Changfang Zhu et al; "Diagnosis of Breast Cancer Using Diffuse Reflectance Spectroscopy: Comparison of a Monte Carlo Versus Partial Least Squares Analysis Based Feature Extraction Technique" Lasers in Surgery and Medicine 38:714-724 (2006).
Office Action dated Nov. 16, 2015 for U.S. Appl. No. 14/149,925 1, filed Jan. 8, 2014.

\* cited by examiner

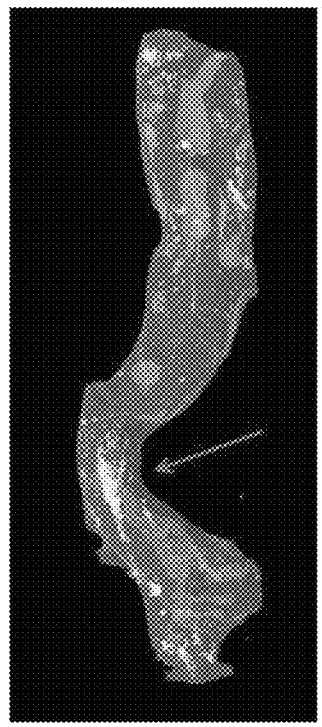
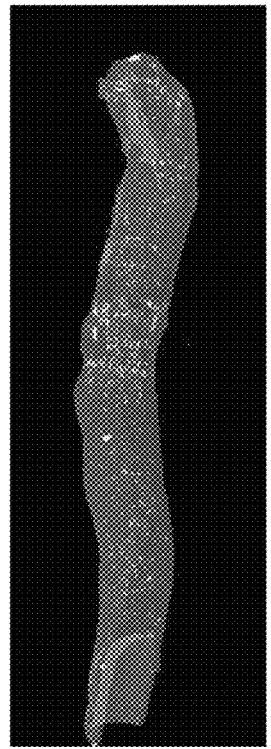
Fig. 25A
Fig. 25B

NON-INVASIVE METHOD AND SYSTEM FOR DETECTION OF CANCER OR ARTERIAL VASCULAR DISORDERS USING METAL NANOPARTICLES

CROSS-REFERENCE TO RELATED PATENT APPLICATIONS

This application is a Continuation in Part (CIP) of U.S. patent application Ser. No. 14/149,925 filed Jan. 8, 2014, which claims priority from U.S. provisional patent application No. 61/749,939 filed on Jan. 8, 2013, and is also based on U.S. provisional patent application No. 61/969,901 filed Mar. 25, 2014, all applications upon which the present CIP application is based being hereby incorporated herein by reference as if fully disclosed herein.

FIELD OF THE INVENTION

The present invention relates to methods and systems for detection of diseases and/or disorders using metal nanoparticles and, more particularly, to non-invasive methods and systems for detection of cancer and arterial vascular disorders using metal nanoparticles.

BACKGROUND OF THE INVENTION

Nanoparticle-based contrast agents for molecular imaging became a mainstay imaging tool for selectively detecting and imaging biological processes and diseases. The use of the enhanced scattering properties of gold nanoparticles as near infrared (NIR) contrast agents is under intensive investigation. This promising field builds on the safety of non-ionizing radiation, ease of generation, relatively high tissue penetration depth, and reduced auto-fluorescence of the tissue in this spectral range. In addition, the particles' superior absorption properties have been utilized for photo-thermal therapy.

The Diffusion Reflection (DR)-based medical imaging method is very attractive since it is non-ionizing, low cost, convenient to generate and detect, and highly sensitive to the optical properties of the tissue. In the last decade, several diagnostic methods were developed based on DR measurements. For example, Yang et al., 2001, suggested UV reflectance spectroscopy for DNA and protein changes probing in human breast tissues. Zhu et al. 2006, presented method for diagnosis of breast cancer using DR spectroscopy, where a physical model (Monte Carlo inverse model) and an empirical model (partial least squares analysis) based approaches were compared for extracting diagnostic features from, the diffuse reflectance spectra. Cerussi et at, 2011, presented diffuse optical spectroscopic imaging (DOSI), which enables the measurement of tissue hemoglobin, water and lipid. Still, as many other spectroscopic methods, the DR technique suffers from multiple scattering which dominates light propagation in tissue. Therefore, a diagnostic tool which can diminish the scattering interruption on the DR signal is desired.

Despite recent therapeutic advances, atherosclerosis and its major vascular complications—myocardial infarction and ischemic cerebrovascular accident remain a leading cause of premature morbidity and mortality. Over the last decades, non-invasive methods have been developed in order to detect atherosclerotic disease before it becomes symptomatic. These have included anatomical imaging techniques such as coronary calcium scoring by Computed Tomography (CT), carotid intimal media thickness (IMT) measurement by ultrasound, and magnetic resonance imaging (MRI). The measurement of various biological markers is also available such as: lipoprotein subclass analysis, hs-CRP, and other inflammatory marker levels. Although there is a rapid progression in imaging techniques, the identification of early, inflamed "active" lesions within the coronary circulation, remains elusive due to small plaque size, cardiac and respiratory motion, and lack of a suitable tracer/marker specific for the unstable plaque. Furthermore, anatomic detection methods are generally more expensive, and the physiologic methods do not quantify the current state of the disease accurately enough to track its progression, in addition, invasive methods, such as angiography, demonstrate changes in the lumen, but not disease within the vessel wall Development of a new, easy to use, and non-invasive method at low cost, to locate atherosclerotic vascular disease (ASVD) at its early stages is desired.

Current imaging techniques are limited to detect early ASVD. Invasive techniques such as angiography have been widely employed to visualize the inside, or lumen, of blood vessels, with particular emphasis on the coronary arteries. Another invasive technique is the intravascular ultrasound (IVUS) that provides cross-sectional images of blood vessels, having the ability to detect and characterize atherosclerotic plaque. Non-invasive CT angiography can also detect significant narrowing and occluding processes in the lumens of various blood vessels. However, these methods focus on detecting significant luminal narrowing, and to a lesser extern on characterizing the underlying ASVD disease.

The ASVD plaques are divided into two broad categories: stable and unstable (also called vulnerable plaques). Stable atherosclerotic plaques tend to be rich in extracellular matrices and smooth muscle cells, while unstable plaques are rich in macrophages, foam cells and inflammatory cells, and usually have a weak fibrous cap. The unstable plaques are prone to rupture into the circulation, inducing thrombus formation in the lumen. Therefore, their detection is critical. One of the most common and fatal complications of ASVD is ruptured unstable plaque followed by thrombotic occlusion, causing myocardial infarction. Meanwhile, there is no reliable method that can distinguish between these two kinds of plaques or detect unstable plaques, prone to rupture.

SUMMARY OF THE INVENTION

According to certain embodiments, the present invention provides a non-invasive and real-time optical method based on diffusion reflection measurements for detection of cancer or arterial vascular disorders comprising the steps of; (a) administering to an individual a composition comprising noble metal nanoparticles that accumulate in a cancerous or injured vascular tissue; (b) optically irradiating an area of a tissue suspected of being a cancerous or injured vascular tissue with a light source outputting an optical signal of at least one wavelength; and (c) measuring diffusion reflection of the area of the irradiated tissue using at least one detector; whereby detection from the measured diffusion reflection of accumulation of the noble metal nanoparticles in the area indicates that the irradiated tissue is a cancerous or injured vascular tissue.

In certain embodiments, measuring of the diffusion reflection is carried out by detecting the changes in intensities of the area of the irradiated tissue for different distances between the light source and the at least one detector (at several distances from the light source, referred to herein also as source-detector separation).

The irradiation may be carried out with a laser device alone or together with at least one optical fiber for guiding light outputted from the laser device to the tissue area.

The nanoparticles for use in toe present invention may be selected from noble metal nanoparticles, e.g., gold, copper, silver, or a combination of them, that present highly tunable optical properties, which can be easily tuned to desirable wavelengths according to their shape (e.g., nanoparticles, nanoshells, nanorods, etc.), size (e.g., 1 to 100 nm), and composition (e.g., core/shell or alloy noble metals), enabling their imaging applications under native tissue. In certain embodiments, the noble metal nanoparticles are gold nanoparticles, optionally selected from gold nanorods (GNRs) or gold nanospheres (GNSs).

According to certain embodiments, the at least one wavelength outputted by the light source device is in the range of 500-900 nm to optimize absorption or scattering of the gold nanoparticles.

According to certain embodiments, the method of the invention is for detection of cancer and the gold nanoparticles are conjugated to targeting moieties that specifically home the golden nanoparticles to the cancerous tissue.

According to certain embodiments, the method comprises the steps of: (i) administering to an individual suspected of having EFGR expressing cancer a composition of gold nanorods (GNRs) conjugated to anti-EGFR antibodies; (ii) optically irradiating the area with a light source outputting an optical signal of wavelength 650 nm or 780 nm; and (m) measuring diffusion reflection of the tissue area; whereby detection from the measured diffusion reflection of accumulation of the conjugated GNRs in the area indicates that the irradiated tissue is a cancerous tissue of a EGFR-expressing cancer.

The EGFR-expressing cancer may be melanoma or head and neck squamous cell carcinoma.

According to some embodiments, the method for detection of cancer further includes measuring the concentration of the conjugated gold nanoparticles in the irradiated tissue, based on calculation of red-shift of the reflected light caused by surface plasmon resonance of the conjugated gold nanoparticles.

According to certain other embodiments, the method of the invention is for detection of arterial vascular disorders, in which case gold nanoparticles are up taken by macrophages and other phagocytic cells present in injured vascular tissue. Optionally, the arterial vascular disorder to be detected is atherosclerotic vascular disease (ASVD) and the injured vascular tissue is inflammatory active atherosclerotic plaque.

According to certain other embodiments of the present invention, there is provided a non-invasive and real time optical system based on diffusion reflection measurements for detection of cancer or arterial vascular disorders, comprising: (a) an optical source setup for irradiating an area of a tissue of an individual to whom a composition of a noble metal nanoparticles has been administered, wherein the optical source comprises a laser device configured for outputting an optical signal of at least one wavelength; (b) at least one detector configured for detecting light reflected from the area of the irradiated tissue; and (c) a processing unit, for receiving output data from the at least one detector in real time and processing thereof for measuring diffusion reflection of the irradiated tissue, whereby detection from the measured diffusion reflection of accumulation of the noble metal nanoparticles in this area indicates that the irradiated tissue is a cancerous or injured vascular tissue.

In certain embodiments of the system, the optical source setup and/or the at least one detector is configured for changing location thereof for measuring reflected light for various source-detector separations, wherein measuring of the diffusion reflection is carried out by detecting the changes in intensities of the irradiated tissue for different source-detector separations.

In certain embodiments, the detector or at least part of the optical source setup may be optionally configured for being moved at predefined distance intervals for changing the source-detector separation or for continuous measuring of spatial reflectance from said irradiated area.

In certain embodiments, the system comprises multiple optical detectors or camera and/or multiple optical fibers for guiding the output light from the laser device to multiple locations, for allowing simultaneous detection of reflected light for multiple source-detector separations for the diffusion reflection measuring.

In certain embodiments, the optical source setup further comprises at least one optical fiber for guiding light outputted by the laser device to the area for irradiating tissue therein, and said optical source setup comprises at least one micrometer plate attached to a distal edge of said at least one optical fiber. The plate may be used for allowing easy displacement of the irradiating fiber edge for displacement of the light source used for the DR measuring.

According to some embodiments, the system further comprises a signal collecting unit for collecting output signals from said at least one detector and outputting signal related data, wherein, the signal collecting unit is configured to transmit the signal related data to the processing unit in real time or near real time via at least one communication link.

The signal collecting unit of the system can be, for instance, an oscilloscope, a central processing unit (CPU) communicating with said processing unit or a software program operable through the processing unit capable of receiving input data from the at least one detector through hardware of the processing unit.

In some embodiments of the system, the optical source setup comprises at least one laser diode outputting an optical signal of a narrow wavelength bandwidth.

In some embodiments of the system, the at least one detector is further configured for detecting frequency spectral data of the optical signal reflected from the irradiated tissue, where the processing unit processes the received spectral data for measuring the concentration of the noble metal nanoparticles in the irradiated tissue, based on calculation of red-shift of the reflected light caused by surface plasmon resonance of the noble metal nanoparticles.

BRIEF DESCRIPTION OF THE DRAWINGS

FIG. 10A shows a homogeneous phantom with a reduced scattering property of m0s_1:45 mm_1, and ma ¼ 0:0137 mm_1 following 650 and 780 nm illuminations (the triangle marked and the solid line, respectively) and a solid phantom containing 0.0.1 mg/ml GNR650 following 650 and 780 nm illuminations (the cross and circle marked lines, respectively); and FIG. 10B shows the same homogeneous phantom following 650 and 780 nm illumination (the triangle marked and the solid line, respectively) and solid phantom containing 0.02 mg/ml GNR780 following 650 and 780 nm illuminations (the cross and circle marked lines, respectively).

FIG. 13A presents the DR profiles of cancerous tissue with a relatively low GNR$_{650}$ concentration; while the reflectance slope following 780 nm illumination presents the same value as before illumination (circle and asterisk marked lines before and after illumination, respectively), 650 nm illumination introduced a sharper slope (triangle marked line) compared to the slope before the GNR injection (solid line). The graph in FIG. 13B indicates the DR profiles of tested cancerous and non-cancerous tissues presenting a higher GNR$_{650}$ concentration. The DR profiles of the tumor following 650 nm and 780 nm illuminations (triangle and asterisk marked lines, respectively) introduced an increase in the curves' slopes compared to the non-cancerous tissue before the GNR$_{650}$ injection (solid and circle marked lines).

FIG. 21A—before incubation with GNS; FIG. 21B—incubation with 0.02 mg/ml of GNS; FIG. 21C—incubation with 0.2 mg/ml of GNS.

FIGS. 25A-25B show ex-vivo high resolution computer tomography (CT) scan of rat injured and healthy arteries. FIG. 25A shows the injured artery. The arrow indicates the distortion in the artery, caused by the injury. It is clearly evident that the GNRs were accumulated in the injured rat area, most probably due to accumulation in macrophages or in other mononuclear cells. FIG. 25B shows the healthy artery, A lower amount of GNRs was accumulated. In addition, the GNRs were homogeneously spread within the artery, rather than amassed in one area.

DETAILED DESCRIPTION OF THE INVENTION

Figure 1:
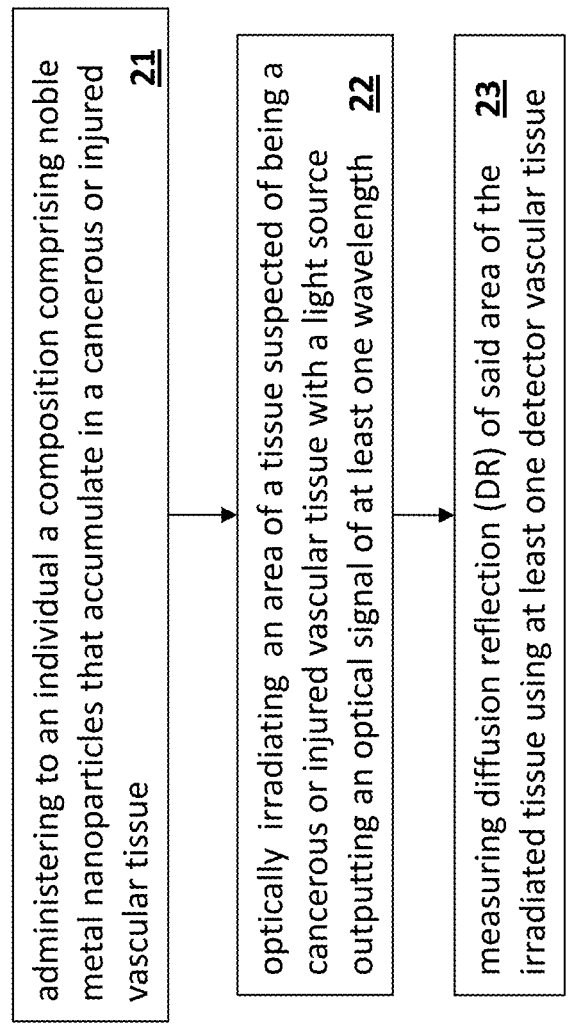
FIG. 1 is a flowchart illustrating a method for detection of cancer or arterial vascular disorders based on diffusion reflection measurements, according to some embodiments of the invention.

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The present invention provides a new, simple and very sensitive non-invasive and real-time optical methods and systems based on diffusion reflection measurements for detection of biological processes related to diseases and disorders such as cancer and arterial vascular disorders based on detection of accumulation of noble metal nanoparticles in the tested tissues. The noble metal nanoparticles used herein are gold nanoparticles (GNPs) such as gold nanorods (GNRs) or gold nanospheres (GNPs) (see Ankri et al. 2012(a), 2012(b) and Fixler et at, 2013(a)). The accumulation of the nanoparticles in the tested area of the tested tissue is carried out by optically irradiating this tissue in the tested area with a light source and measuring diffusion reflection (DR) from the irradiated tissue.

The DR technique, in some embodiments of the present invention, is based at least on an optical source and one or more detectors, which are placed along surface of an area in which tissue is to be optically irradiated. The distance between the source and the detector is changed, e.g. from a few millimeters to a few centimeters, and intensities of light reflected from the irradiated tissue in the tested area is measured for each source-detector separation for DR measuring.

The detector can be any known in the art device configured for optically detecting light reflected within the wavelength range suited to the metal nanoparticles' optical properties such as Infrared camera, photodiode and the like.

Various similar or other DR measuring techniques can be used such as techniques described in Keinle et al., 1996 and Doornbos et al., 1999. GNPs have long been used in the detection and imaging of biological processes and diseases. Examples of such techniques are described in Popovzer et al. (2008), Zhang et al. (2009), Robinson et al. (2010) and Fixler et al. (2013(b)). The broad range of applications for GNPs is based on their unique chemical and physical properties and, in particular, on their optical properties from the visible to the infrared (IR) region, depending on the particle size, shape, and structure (see Eustic et al (2006) and Jain et al. (2006)). Once the GNPs accumulate in the specific tissue, the DR profile changes according to the optical properties of the GNPs.

In certain embodiments, the DR measuring technique of the present invention can be used for detection of cancer, e.g., melanoma or head and neck cancer such as head and neck squamous cell carcinoma, or for arterial vascular disorders such as atherosclerotic vascular disease (ASVD) and other vascular injuries.

According to some embodiments of the invention, the DR measuring method is used for detection of cancer by detection of accumulated noble metal nanoparticles in the irradiated tissue, the nanoparticles in this case having been modified by conjugation with moieties that target the conjugated nanoparticles to bind to specific receptors of cancer cells of the cancerous tissue to be detected.

In other certain embodiments, the DR technique of the invention is used for detection of arterial vascular disorders by detection of accumulation of phagocytes, particularly macrophages, that up take the noble metal nanoparticles therein.

The metal nanoparticles for use in the present invention may be selected from noble metal nanoparticles, e.g., gold, copper, silver, or a combination of them, that, present highly tunable optical properties, which can be easily tuned to desirable wavelengths according to their shape (e.g., nanoparticles, nano-shells, nanorods, etc.), size (e.g., 1 to 100 nm), and composition (e.g., core/shell or alloy noble metals), enabling their imaging applications under native tissue.

These noble metal nanoparticles can also be easily functionalized with or conjugated to a biocompatible polymer, e.g., polyethylene glycol (PEG), or with moieties such as antibodies, peptides, and/or DNA/RNA to specifically target, different cells for cancer detection purposes.

The terms "nanoparticles" and "metal nanoparticles" are used herein interchangeably for metal nanoparticles. The term "targeted nanoparticles" as used herein refers to nanoparticles as described above which are configured in a way such that they bind specifically to cancer cells and thus accumulate in a cancerous tissue.

In certain embodiments, the nanoparticles used in the present invention are gold nanoparticles such as gold nanorods (GNRs). Since most cancer cells present epidermal growth factor receptor (EGFR) molecules on their surface, in certain embodiments the gold nanoparticles can be conjugated to an anti-EFGR antibody, e.g., Cetuximab, forming targeted nanoparticles that home specifically to cancer cells. In some embodiments, the EGFR-bearing cancer cells are, without being limited to, melanoma and squamous cell carcinoma of head and neck cancer.

According to certain embodiments of the invention, the noble metal nanoparticles are administered to an individual in compositions comprising the noble metal nanoparticles along with suitable pharmaceutically acceptable carriers.

The composition is administered to the individual by any suitable mode of administration. In certain embodiments, the composition is administered by intravenous injection.

The distance between the detector(s) detecting the irradiated Sight from the tissue and the light source emitting light for irradiating the same tissue is defined herein as "source-detector separation".

According to certain embodiments of the method of the present invention for the detection of cancer, an area of a tissue in which the targeted nanoparticles are accumulated is optically irradiated with a light source that outputs optical signal of one or more wavelengths. Cancerous tissue can be identified by detecting intensity of light emitted from the irradiated tissue for different distances between the light source and the detector(s) and calculating optical properties such as absorption and/or scattering coefficients of the irradiated tissue based on diffusion reflection mathematical models which define the relation between the intensity, the source-detector separation and the absorption/scattering coefficients of the tissue.

Certain aspects of the experimental and theoretical aspects and details of the present invention have been disclosed by the inventors in the following publications: Ankri R et. al. (2012a, 2012b, 2013), all of which are incorporated by reference herein in their entirety as if folly described herein.

The diffusion reflectance (DR) profile of an irradiated tissue depends on its absorption and scattering coefficients (Jacques et al., 2008). The absorption coefficient of a tissue is predominantly determined by the concentration of the absorbance molecules, while the scattering coefficient depends mainly on the size and shape of the scattering components in the tissue, rather than their concentration (Shimada et al., 2009). Since imaging techniques that are based on scattering (with or without nanoparticles as contrast agents) suffer from relatively high background noise and low contrast, the diffusion reflection (DR) method is designed herein to focus mainly on the absorption properties of the targeted nanoparticles rather than their scattering properties. As a result, no contrast interruptions are expected.

Since GNRs have unique size- and shape-dependent optical properties, they can cause a significant change in the optical properties of the targeted tissue. Previous studies have presented diffuse reflectance measurements for cancer diagnosis (Bigio et al., 2000) but without nanoparticles as contrast agents. The diffusion reflectance method described in the present invention presents higher efficiency and sensitivity resulting from the GNR insertion that specifically target cancerous cells and significantly change their absorption.

In certain embodiments, the invention relates to measuring the diffusion reflectance for head and neck cancer (HNC) using GNRs that are targeted to the cancerous tissue. The head and neck lymph nodes are located adjacent to the skin where visible-NIR light can easily penetrate when using a light source that radiates the tissue in a non-invasive manner by, for example, placing an outlet of an optical fiber connected to a laser light source over the patient's skin in the head and/or neck area where a cancerous tumor is suspected to be located, after targeted nanoparticles have been administered.

One of the major diagnosis challenges in HNC today is reliable detection of involved lymph nodes, since their status is one of the most important prognosis predictors and is also pivotal for appropriate treatment. However, assessment of lymph nodes based on currently available imaging techniques is limited in sensitivity and specificity and fails to distinguish between non-neoplastic and malignant processes. These limitations lead to the routine performance of prophylactic procedures such as extensive neck dissection and radiation. Hence, the development of more sensitive in vivo detection techniques is of major importance and could substantially improve HNC treatment and potential cure.

According to some embodiments, the method of the present invention is applied for HNC detection, wherein targeted EGFR-conjugated GNRs are intravenously injected into the patient; and the diffusion reflection technique is used to detect cancer based on the absorption coefficient differences between cancerous and normal tissues in a specific head and/or neck area of said patient.

The diffusion reflection is based on a diffusion model (Jacques et al., 2008), which assumes that light can be treated as a concentration of optical energy that diffuses down a concentration gradient. The loss of energy is caused by the absorbing and scattering of components within the tissue (Jacques et al., 2008). The diffusion model can solve several classes of image or property recovery problems. One of the most common among them is the measured $\Gamma(\rho)$ function. This $\Gamma(\rho)$ function, which describes the reflected light intensity (defined as $\Gamma$) at the tissue surface in several light source-detector separations (defined as $\rho$), presents a strong correlation to the tissue optical properties, such as the absorption coefficient $\mu_a$ and the reduced scattering coefficient $\mu_s'$. The intensity of the reflected light $\Gamma(\rho)$ function is described by the general formula of (Schmitt et al., 1990 and Farreil et al., 1992):

$\Gamma(\rho)=[c_1/(\rho)^n]\cdot\exp(-\mu\rho)$, referred to hereinafter as Equation 1.

$C_1$ is a constant, depending on the optical properties of the medium and on the sizes of the source and detector apertures; n is the power of $\rho$, which depends on $\rho$'s range and on the ratio $\mu_a/\mu_s'$, $\mu$ is an effective attenuation coefficient given by $\mu=\sqrt{(3\cdot\mu_a\cdot\mu_s')}$, referred to hereinafter as Equation 2 (Jacques et al., 2008).

"n" is the power of $\rho$, which depends on $\rho$'s range and on the scattering properties of the tissue (Farrell et al., 1992). "n" depends also on the tissue absorption properties, as in the limit of zero absorption n is nearly 2 (Schmitt et al., 1990). In the case of n=2, the reflectance profile is highly sensitive to the optical properties of the tissue and, as a result, better distinguishes between absorption coefficients that only slightly differ from each other.

By inserting n=2 to Equation (Eq. 1), it can be rewritten as:

$\ln(\rho^2\Gamma(\rho))=c_2-\mu^*\rho$, referred to hereinafter as Eq. 3.

Eq. 3 presents a linear correlation between $\ln(\rho^2\Gamma(\rho))$ and $\mu$.

Resulting from Eq. 2 and Eq. 3, the square slope of the linear curve depends on the product between the absorption and the reduced scattering coefficients of the tissue.

Reference is now made to FIG. 1, which is a flowchart schematically illustrating a non-invasive and real-time optical method based on DR measurements for detection of cancer or arterial vascular disorders, according to some embodiments of the invention. In the first step, a composition comprising noble metal nanoparticles such as gold nanoparticles is administered to an individual 21. The nanoparticles composition is designed to accumulate in a cancerous or injured vascular tissue and may require an incubation period of a few hours. After the administering of the composition, an area of a tissue suspected of being a cancerous or injured vascular tissue is optically irradiated with a light source such as a laser device outputting an optical signal of at least one wavelength 22. Reflected light from the tested area is then detected according to a special detection technique for measuring diffusion reflection of this tested area of the irradiated tissue using at least one detector. For example the DR is measured by measuring the intensities of reflected light from the area for different source-detector separations i.e. for different distances between the light source and the detector. The method relies on the fact that cancerous or injured tissue will cause accumulation of the noble metal nanoparticles and therefore the detection of the disease is based on detection of accumulated nanoparticles in the irradiated tissue of the tested area. Therefore, detection from the measured diffusion reflection of accumulation of the noble metal nanoparticles in the tested area indicates that the irradiated tissue therein is a cancerous or injured vascular tissue.

In certain embodiments, the method is used for detection of superficial tumors such as for detection of head and neck cancer, and the light source (e.g. a laser diode or any other laser configured for outputting monochromatic optical signals in the NIR range) is located in or guided to an external body area that is in proximity to the inner tissue area that is to be irradiated. The emitted light can non-invasively penetrate the skin to reach inner tissue thereof for irradiation of the internal tissue.

Accumulation of nanoparticles in the tissue in the tested area can be detected, according to some embodiments, by detecting intensity of optical signal emitted from the irradiated tissue, for example using one or more optical detectors such as photodiodes adapted to detect, optical signals of wavelengths/frequencies in the range of the irradiated tissue, for various distances from the detector to the light source and calculating absorption/scattering optical properties of the tissue including the accumulated nanoparticles, using a diffusion reflection based mathematical model.

The optical properties deduced from the detected intensities (e.g., deduced from amplitudes of the detected signals) and optionally also from wavelength properties in correlation to the source-detector separations may be further processed using image analysis to convert the data received from the detector(s) into a two or three dimensional image of the tissue area for cancer or vascular disorder detection (e.g. by using a distinguishable color for the detected nanoparticles accumulation zones contrasted by other colors of the tissue areas with no nanoparticles accumulation).

According to certain embodiments, a designated computer program may be used, which enables receiving and processing the detector's output data according to predefined algorithms capable of producing, inter alia, imagery output and for calculating the tissue zones having clusters of accumulated nanoparticles. This program may also be configured for identifying borders of a tumor by identifying where concentrations of the nanoparticles (coloring the overall image of the tissue) rapidly decrease, for example, or by using any other method(s) for border identification that relate to the DR imagery of the tested tissue/area.

According to certain embodiments of the invention, the nanoparticles are gold nanorods (GNRs). To prevent aggregation, to stabilize the particles in physiological solution and to improve blood circulation time, the gold nanorods can be coated with a layer of polyethylene glycol (mPEG-SH, for example of molecular weight MW 5.000 g/mol). This layer also provides the chemical groups that are required for conjugation with the antibodies (SH-PEG-COOH, MW+ 3400 g/nol) as described according to the invention. Thus, in certain embodiments, the antibodies are conjugated to polyethyleneglycol coated-gold nanorods.

To allow the gold nanorods to bind to cancer cells, the gold nanorods are conjugated with targeting moieties specific to receptors present, on the surface of the specific cancer cells. For instance, to allow the gold nanorods to bind to cancer cells bearing EGFR such as melanoma and head and neck cancer squamous cell carcinoma, the targeting moieties are antibodies to EGFR; for binding to HER2 (human EGFR2)-positive breast cancer cells, the gold nanorods are conjugated to anti-HER2 antibodies such as Herceptin.

The targeted nanoparticles, e.g. the antibody-conjugated gold nanorods, are administered to an individual suspected of having cancer at a certain time prior to the optical irradiation of the cancerous tissue for allowing them to accumulate in the tissue. The detection of nanoparticles in the tissue should start after a minimum accumulation period for allowing the nanoparticles to reach the designated tissue area and to bind to cancer cells in the tissue.

Figure 2A:
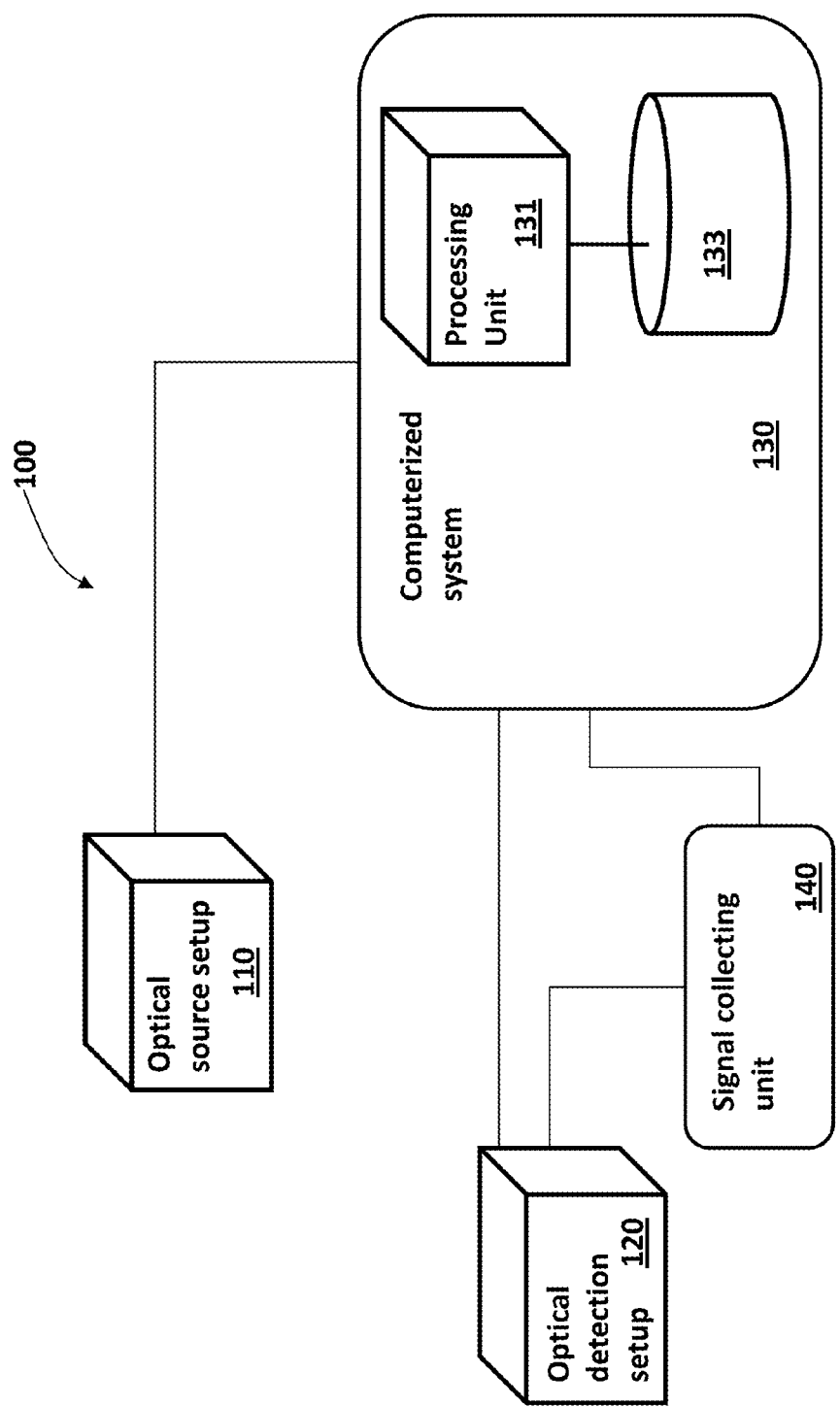
FIG. 2A schematically illustrates a system for detection of cancer or arterial vascular disorders based on diffusion reflection measurements, according to some embodiments of the invention.

Reference is now made to FIG. 2A showing a block diagram, which generally portrays a system 100 for noninvasive detection of cancer or arterial vascular disorders, according to some embodiments of the invention. The system 100 includes an optical source setup 110 configured for outputting an optical signal (beam) at one or more wavelength or wavelength bands that correspond to excitation wavelength/wavelength band of the nanoparticles administered to a patient and for noninvasively irradiating inner and/or external tissues of the patient's body in one or more selected body areas. This means that the output of the optical source setup 110 (e.g. a laser device that outputs a monochromatic coherent optical signal at a predefined wavelength where the output light thereof is guided via an optical fiber) is placed over or near the patient's skin or any other exposed tissue to irradiate internal and/or external tissue proximal to the positioning of the optical source output. The system 100 also includes a detection setup 120 including one or more detectors such as one or more photodiodes or cameras such as IR cameras, or a charged coupled device (CCD) cameras and the like, for noninvasively detecting Sight reflected from the irradiated tissue. This means that each detector is placed over or in proximity to the patient's skin or other exposed tissue for detecting light scattered from the irradiated tissue including the irradiated nanoparticles therein. In cases in which the system 100 is used for detecting cancerous tissue related to head and neck cancer, the detector and output of the light source are located in proximity to the skin surface.

Output of the detector(s) from the detection setup 120 is collected and processed at a computerized system 130 having one or more processors 131 and one or more data storage units such as a database 133.

The processing unit is configured to operate one or more software based applications/algorithms for receiving data indicative of the detected light and calculate according to the received data, absorption and/or scattering properties of the irradiated tissue for detecting nanoparticles therein and their location in the tissue. To identify those optical properties, the diffusion reflection methodic is used, where the relation between the intensity (which may be deduced from signal amplitude detection) and source-detector separation is taken from the below described equations.

The system 100 optionally includes a signal collecting unit 140 in cases in which the output of the detector is not directly transmitted to the processing unit but through a mediating hardware/software means such as through an oscilloscope, a computer processing unit (CPU), for example. For example, the data from the detection setup 120 may be transmitted through cables to the computerized system 130, which may operate a designated LabView™ program configured for converting the detector data into computer readable information for identifying, for instance, the intensity vs. the source-detector separation values and optionally also the frequency/wavelength thereof.

The detector may be configured, for measuring light signal intensity (amplitude) and frequency. The detected intensity is then analyzed in respect to each source-detector separation value it is associated with, to allow calculating the diffusion reflection (DR) based absorption/scattering properties of the tissue for detection of nanoparticles accumulation therein and therefore for the detection of cancerous or vascular injured tissue.

The optical source setup 110 may include any known in the art light source that is configured to produce light of the desired wavelength/wavelength, hand such as a laser diode source, a Xenon illumination source and the like. The optical source setup 110 may also include optical devices and elements for noninvasively directing and/or guiding light to the selected external body area from which the tissue is to be irradiated such as one or more optical fibers, one or more lenses and/or phase elements, filters and the like.

According to some embodiments of the invention, the optical source and detection setups 110 and 120, respectively, are combined in a single device that is configured for both transmitting and detecting optical signals over the skin of a patient. Optionally, the combined device includes a processor for on-chip processing of the detected signals from the optical detector(s) configured for carrying out at least some of the required processing or for conversion of the signal into computer-readable data.

Figure 2B:
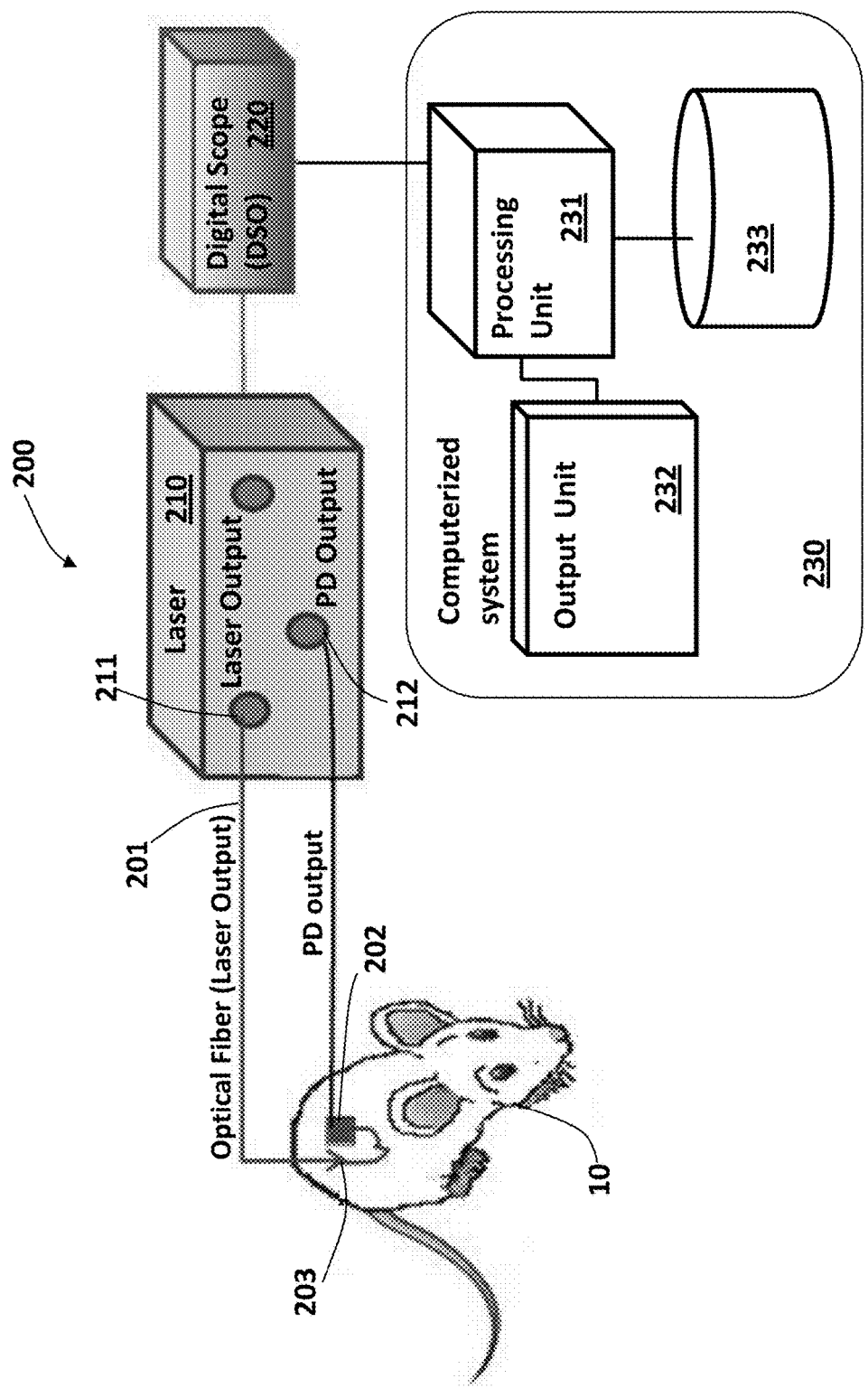
FIG. 2B schematically illustrates a system for detection of cancer or arterial vascular disorders based on diffusion reflection measurements that includes a laser diode source for emitting NIR light, according to some embodiments of the invention.

Reference is now made to FIG. 2B, which schematically illustrates a system 200 for detection of cancer or arterial vascular disorders that uses a laser diode source device for emitting NIR light, according to some embodiments of the invention. This system 200 includes a laser diode based laser device 210 configured for outputting an optical signal at one or more narrow wavelength band such as at 650 nm for targeted gold nanorods for cancer detection. The system 200 also used an optical fiber 201 connected to the output 211 of the laser device 210 for directing the outputted light therethrough to allow irradiating the desired inner and/or outer tissue of the respective patient by noninvasively approximating the output of the fiber 201 to the patient's 10 exposable tissue. The system 200 additionally includes one or more optical sensors configured for sensing light scattered from the irradiated tissue at the wavelength range of the scattered light adapted for light scattered from the particular type of nanoparticles being used, such as a photodiode (PD) 202. The location of the PD 202 can be shifted to allow changing the distance between the PD 202 and the fiber 201 output (source) for measuring intensity of reflected light from the irradiated tissue at different source-detector separations "ρ".

The output of the optical fiber 201 may optionally be coupled to localizing device such as to a micrometer plate 203 for allowing easy displacement of the output of the fiber 201 outputting end and holding it in each location in respect to the patient's skin, to change the distance between the light source and the detector.

According to some embodiments, the optical fiber 201 is configured for guiding optical signals (beams) at one or more wavelengths/frequencies or wavelength/frequency ranges adapted to the output of the laser diode.

According to this method, the source-detector separations "ρ" is changed over time by changing the distance between the light source (e.g. end of output of the fiber 201) and the PD 202 by changing over time the location of at least one of: the fiber 201 output end and/or the PD 202 and taking a measurement of the intensity of the irradiated tissue at this location of the PD 202 for each source-detector separations "ρ".

According to other embodiments of the invention, the intensity is measured for various source-detector separations "ρ" simultaneously. This may be abled by having a system in which there are multiple PDs each located at a different location near the area that is to be tested for tumor detection. According to other embodiments of the invention, the optical sensor includes one or more optical cameras sensitive to the respective wavelength being used, each camera configured for simultaneously measuring the intensity of irradiated light from within the tissue for several source-detector separations.

According to some embodiments of the invention, as illustrated in FIG. 2B, the system 200 also includes a digital oscilloscope 220 such as a digital storage oscilloscope (DSO) and a computerized system 230 communicative with the digital scope 220. The oscilloscope 220 is configured for collecting the reflected intensity $\Gamma(\rho)$ (in volts). The intensity measurements data is transferred whether in real time or not, to the computerized system 230 for further processing thereof. The computerized system may include, as illustrated in FIG. 28, any known in the art computerized means for receiving, transmitting, storing, processing and outputting of data such as a processing unit 231, one or more output units such as a screen 232 and a data storage unit (e.g. database) 233.

The processing unit 231 receives the raw data from the digital oscilloscope 220 indicative of intensities of reflected light measured by the PD 202, and analyzes this data to calculate one or more related measures associated with these detected intensities in response to known source detector separation values each associated with a different intensity detection, which may be known, where the relation between the source-detector separation and the reflection intensity (or a logarithm thereof) corresponds to the diffusion reflection (energy concentration gradient) of light of the irradiated tissue.

According to other embodiments of the invention, methods and systems based on dark field microscopy and imaging may be used for detection and analysis of the reflected (scattered) light; where scattered beams are excluded from the imaging.

According to some embodiments several detectors may be used and one or more light sources e.g. a single laser device radiating the tissue through several optical fibers guiding the laser output therethrough for simultaneously measuring reflected light for multiple source-detector separations.

Figure 3:
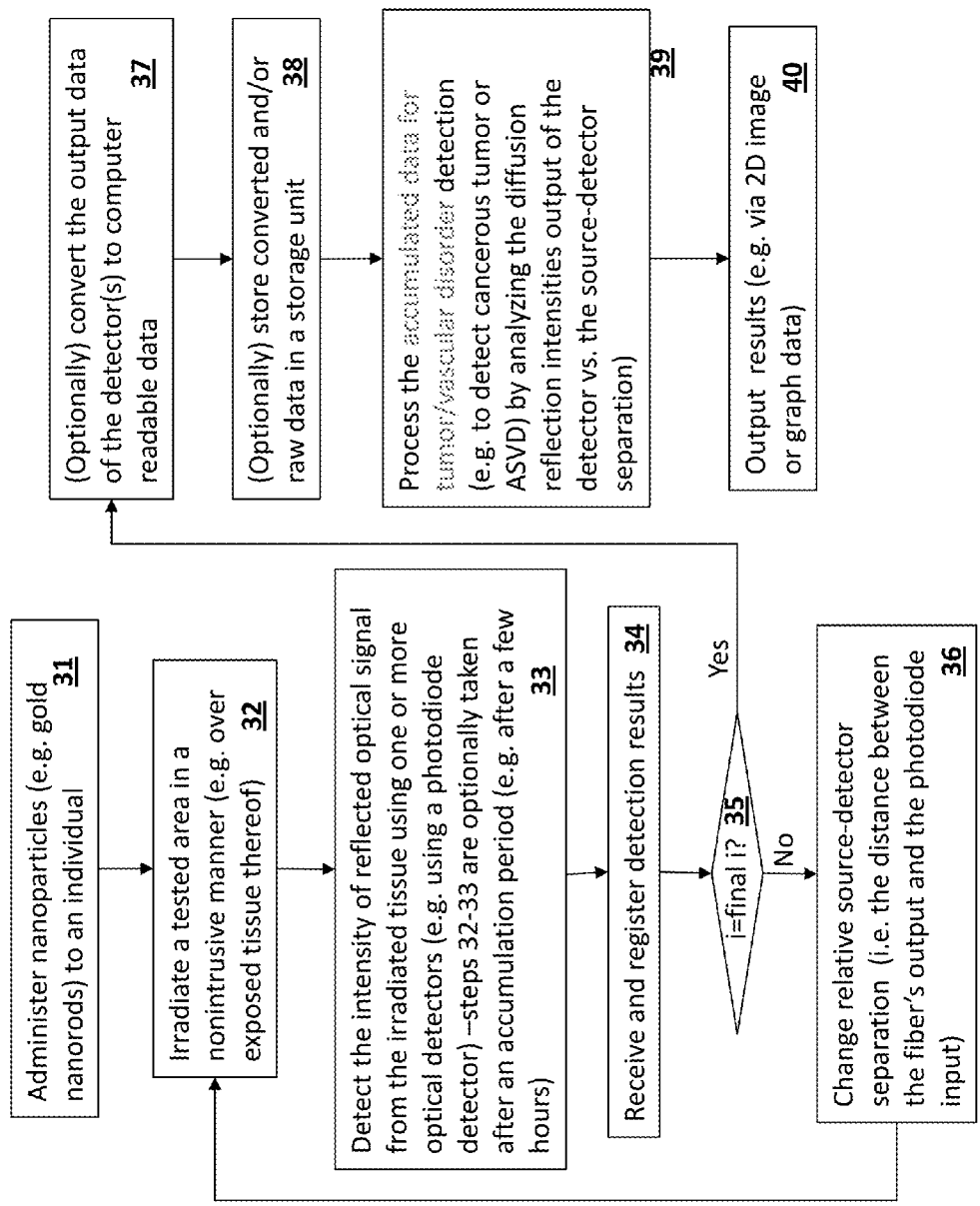
FIG. 3 is a flowchart illustrating a method for detection of cancer or arterial vascular disorders using detector/source displacement, according to some embodiments of the invention.

Reference is now made to FIG. 3, which is a flowchart schematically illustrating a detailed method for DR measuring using nanoparticles, according to some embodiments of the invention. This method includes administering the nanoparticles to the patient 31. After the administration of the targeted nanoparticles 31, the tested tissue is noninvasively irradiated 32 with an optical signal of at least one wavelength within a predefined range (such as the NIR range) and corresponding irradiated tissue detection is carried out 33.

The irradiation of the tissue is carried out, for example, by using a laser diode source and an optical fiber that guides and directs the coherent monochromatic laser light beam therethrough and outputs it in proximity or over the patient's skin in proximity externally and the tested tissue. The detector used may include one or more PDs or a CCD camera placed in proximity or over the patient's skin close to the output of the optical fiber. The source-detector separation is changed at each measurement over time 35-36 by, for example, changing a location of the optical fiber output, and/or by changing the location of the PD for changing the respective distance therebetween, which defines the source-detector separation "ρ". Optionally the source-detector separation is varied at predefined equal distance intervals. This allows measuring the irradiation for various values of source-detector separations for identifying the diffusive behavior of light in the tested tissue.

The detector detects the intensity/amplitude of optical signals of light reflected from the irradiated tissue. This tissue may be located under the exposed tissue. The signal outputted from the detector is then optionally converted to a computer/processor readable data 37 and stored 38 in a computerized storage. The accumulated data including the intensity/amplitude values of various source-detector separations is then processed 39 by a computerized system (e.g. PC computer) for analyzing DR optical properties such as slope thereof which is indicative of how the irradiated light diffuses through the tested tissue to detect accumulation of administered nanoparticles in the irradiated tissue in the tested area. The results of the processing may be outputted 38 using imagery presentation of the tested tissue that shows thereof in multiples colors where each color represents the presence of the nanoparticles indicating the different concentrations thereof over the tested tissue, which may indicate the location and presence of tumorous (cancerous) tissues for identifying borders of the tumor in the tested area.

According to some embodiments of the present invention, the method additionally includes identifying concentration of nanoparticles in the tissue by using an additional measurement and processing method that is based on intercepting surface plasmon resonance (SPR) occurring when the nanoparticles are densely accumulated in the tissue.

SPR is achieved by using light (such as infrared (IR) or NIR mono or multi chromatic laser beam) for excitation of metallic surfaces of nanoparticles causing oscillations thereof. These oscillations exhibit enhanced near-field amplitudes at the resonance wavelength, where this field is localized, meaning that the field amplitude decreases dramatically when distance from the nanoparticle's surface increases, providing thereby a high spatial resolution, allowing easy distinction between the resonating nanoparticles surfaces and their non-resonating environment. This resonating causes a slight yet distinguishable red-shift in the wavelength of the light irradiated from those inter-coupled nanoparticles allowing identification thereof by detecting the wavelength/frequency of the optical signal irradiated from the tissue (in addition to detection of the signal's intensity/amplitude).

In this method, the area where the nanoparticles are highly concentrated (the tumor area/peripheries or the injured vascular tissue) is distinguished from the normal concentrated healthy tissue by detection of the nanoparticles accumulation in the areas of the diseased tissue. The inter-particle plasmon resonance pattern of the highly concentrated nanoparticles leads to an extension and a red-shift (Δλ) in the absorption spectrum of the concentrated nanoparticles and thereby allows detection of the nanoparticles accumulation after a much lower accumulation time.

Different doses and concentrations of the administered nanoparticles composition can be used to improve identification of the red-shift as well as using multi-chromatic source such as a multi-chromatic laser or a multiplicity of laser diodes, each outputting optical signal of a different wavelength.

Gold nanorods (GNRs) have unique size and shape dependent optical properties. They have the ability to resonantly absorb and scatter visible and NIR light upon the excitation of their surface plasmon oscillation and usually present intense and narrow absorption/scattering peaks (Jain et al., 2006). Since the $\Gamma(\rho)$ profile highly depends on the tissue absorption and scattering properties, decorating the tumor with specifically targeted GNRs changes the measured $\Gamma(\rho)$ in the tumor compared with normal tissue. This phenomenon exists as long as the reflected intensity is measured at a wavelength corresponding to the GNRs absorption/scattering SPR peak. In the current invention, tissue-like phantoms and mice were irradiated with a 650 nm laser. At this wavelength, certain sizes of GNRs can have significant absorption but a negligible scattering coefficient. As a result, the measurements in this work focused on the change in tissue absorption following the GNRs injection, rather than on the change in its scattering properties which is mostly measured in NIR molecular spectroscopy and imaging techniques.

According to other embodiments of the invention, the frequency domain photon migration (FDPM) method (Pham et al., 2000; Cerrusi et al., 2011) is used for GNR-based imaging. The FDPM method is a multi-wavelength, high bandwidth (1 GHz) method that has been developed for quantitative and non-invasive measurements of tissue optical and physiological properties (Tromberg et al., 1997). FDPM is used to generate optical absorption and scattering maps at different wavelengths in the NIR region (650-1000 nm), wherein tissue absorption is relatively low and light can penetrate deep volumes of tissue-up to several centimeters (Lin et al., 2011). The detected penetration depth of the photons within the tissue measured by the FDPM method is higher compared to the DR method which measure the reflected intensity only (enabling a detection depth of few millimeters as described in 34 (i)).

The invention will now be illustrated by the following non-limiting Examples.

Materials and Methods

The Diffusion Reflection Method

The diffusion model (Jacques et al., 2008), as described above, is among the main approaches that best describe the light path in tissues. This approach assumes that light can be treated as a concentration of optical energy that diffuses down a concentration gradient. The loss of energy is caused by the absorbing and scattering components within the tissue (Jacques et al., 2008). The diffusion model can solve several classes of image or property recovery problems. One of the most common among them is the measured $\Gamma(\rho)$. This $\Gamma(\rho)$ function, which describes the reflected light intensity (defined as $\Gamma$) at the tissue surface in several light source-detector separations "ρ", presents a strong correlation to the tissue optical properties, such as the absorption coefficient $\mu_a$ and the reduced scattering coefficient $\mu_s'$, as discussed above (Schmitt et al., 1990): $\Gamma(\rho)=[c_1/(\rho)^n]\cdot\exp(-\mu\rho)$.

The $\Gamma(\rho)$ profile is influenced by the optical properties of the tested tissue, such as its absorption and scattering coefficients ($\mu_s$ and $\mu_a$, respectively) and the anisotropy factor "g". Whereas $\mu_a$ is mainly related to tissue's chromophores (Feather et al., 1998), $\mu_s$ and g reflect the form and concentration of the scattering components in the irradiated tissue (Hielscher et al., 1997). As the biological tissue is defined as a turbid three-dimensional medium, the scattering property of the tissue is usually defined by the reduced scattering coefficient, $\mu_s'$, calculated by the following equation:

$$\mu_s'=(1-g)\mu_s$$

There are several researches that presented the influence of the tissue's optical parameters on the light path within the tissue. These include the effect of anisotropic optical properties on the photon migration (Dagdug et al., 2003), the time of flight and photon path length for photons in tissues using the radiation transfer equation (Zaccanti et al., 1999) and the penetration depth in irradiated tissue (Bonner et al., 1998).

Experiments Set I:
Materials and Methods
Gold Nanorods (GNR) Fabrication and Targeting In this experiment, GNR were synthesized using the seed mediated growth method (Nikoobakht et al., 2003). The size, shape, and uniformity of the NGRs were characterized using transmission electron microscopy, and the resultant size was 25 nm×65 nm, with narrow size distribution (10%). A solution of GNR suspended in cetyltrimethylammonium bromide (CTAB) (Sigma-Aldrich, St Louis, Mo.) was centrifuged at 11,000 g for ten minutes, decanted, and resuspended in water to remove excess CTAB. To prevent aggregation, the particles were stabilized in physiological solution, and to improve blood circulation time, a layer of polyethylene glycol (mPEG-SH, molecular weight [MW] 5000 g/mol) (creative PEGWorks, Winston-Salem, N.C.) was adsorbed onto the GNR. This layer also provided the chemical groups that are required for antibody conjugations (SH-PEG-COOH, MW 3400 g/mol). The absorption spectrum of bare GNR. PEGylated and anti-EGFR-coated GNR solutions were measured. Zeta potentials (Maldiney et al., 2011) (ZetaSizer 3000HS, Malvern Instruments. Worcestershire. UK) of the resulting GNR were measured and are presented in the following Table 1:

TABLE 1

| Sample | Zeta potential (mV) |
| --- | --- |
| Bare GNR | +13.1 |
| PEG-coated GNR | +0.87 |
| Anti-EGFR coated GNR | +5 |

The zeta potentials were measured while the GNR were suspended in water with excess cetyltrimethyl ammonium bromide (CTAB).

The zeta potential indicates the stability of colloidal dispersions. With regard to the GNR, the zeta potential refers to the repulsion between adjacent, similarly charged particles. GNR stabilized in CTAB solution showed cationic surfaces (+13.1 mV). This was due to adsorbed CTAB that has a quaternary amine as a hydrophilic head. In contrast, PEG-modified GNR showed a nearly neutral surface (+0.87 mV). To specifically target SCC HNC, the PEGylated GNR were coated with Cetuximab (Erbitux, Merck KGaA, Germany), a monoclonal antibody against EGFRs that is highly sensitive to HNC SCC. The binding of the EGFRs to the GNR was confirmed by zeta potential measurement, resulting in a positive potential (+5 mV, see Table 1). The antibody conjugated GNR were stable for up to 3 months, confirmed by their maintenance of the same plasmon resonance.

Figure 4:
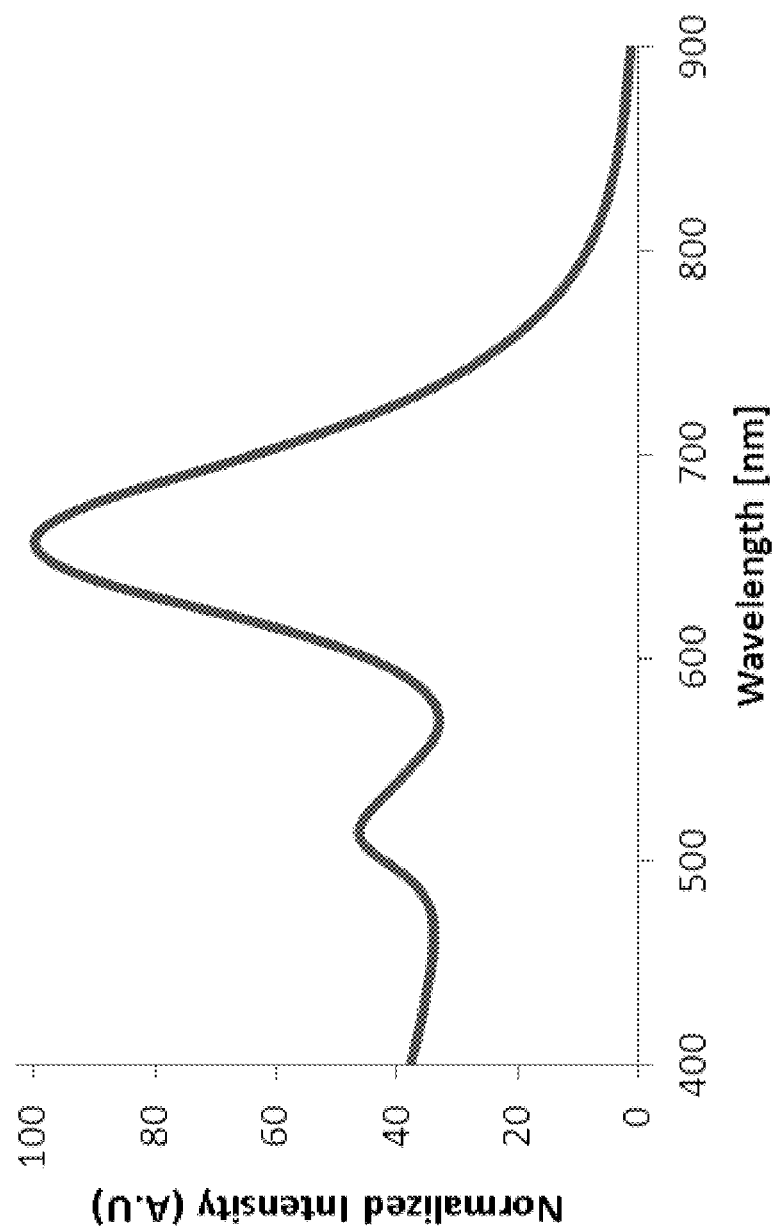
FIG. 4 is a diagram showing the absorption spectra of gold nanorods (GNR); Ultra-violet visible absorption spectra (normalized) of bare GNRs (25 nm*65 nm), PEG-coated and anti-EGFR-coated GNRs, and transmission electron microscopy image of the bare GNRs (inset).

FIG. 4 shows the absorption spectra of GNR for varying wavelengths within the NIR range. It is clear form this testing that the best absorption is performed at a wavelength of 650 nm. This preliminary testing was used to determine the optical wavelength to use when irradiating the tissue/phantom in the following experiments.

System Setup:

For this experiment, the system used 200 was the one described in FIG. 2B. In this system 200 a laser diode based laser device 210 connected to an optical fiber 201 is used to emitting coherent laser beam of 650 nm, which is guided by the optical fiber 201 towards the skin of the patient 10 (in this case a mouse bearing human HNC) for detecting the irradiated light from the cancerous tissue, using a PD 202 detector suitable for detection of light at a wavelength range of the irradiated tissue. The fiber 201 used was 125 µm in diameter and was connected at its output end to a micrometer plate 203 for enabling consecutive reflected light intensity Γ measuring. In this experiment the micrometer plate 203 was moved in twenty incremental steps of 250 µm per step to allow changing the source-detector separation "ρ", varying between 1-6 mm. The source-detector separation "ρ" is defined, in this experiment, as the distance between the PD 202 location and the light source (i.e. the output of the optical fiber 201 location). The reflected intensity Γ(ρ) (in volts) was collected from the digital scope 220 (Mso/7034a; Agilent Technologies, Santa Clara, Calif.), and the data was processed by using, inter alia, Matlab based analysis algorithms that were developed especially for experiments, systems and methods of the present invention.

Phantom Preparation:

Solid phantoms with different absorption coefficients were prepared in order to simulate skin tissues with different optical properties (Dam et al., 2001). The phantoms were prepared using India ink 0.1% as an absorbing component, Intralipid® 20% (Lipofundin MCT/LCT 20%, B, Braun Melsungen AG, Melsungen, Germany) as a scattering component (Cubeddu et al., 1997), and 1% agarose powder (SeaKem LB Agarose, Lonza, Norwalk, Conn.) in order to convert the solution into a gel. The solutions were heated and mixed (at a mixing temperature of ~90° C.) while the agarose powder was slowly added. The absorption spectrum of the India ink was determined using a spectrophotometer, and the absorption coefficient of each phantom was calculated according to the concentration of the ink in each solution. The scattering properties of the phantoms were determined according to the scattering coefficients presented by Cubeddu et al., 1997.

The phantoms were prepared in cell culture plates (90 mm) and were cooled under vacuum conditions (to avoid bubbles). Five phantoms with the same scattering properties and different absorption coefficients were prepared. Each phantom contained 2% of Intralipid and increasing concentrations of India ink; 5.0×10−4, 2.5×10−3, 5.0×10−3, 7.0×10−3, and 1.0×10−2(%). The resulted scattering coefficient was ~1.6 mm−1, and the resulting absorption coefficients were $\mu_a$=0.0064, 0.0126, 0.0180, 0.0227, and 0.0295 mm−1, respectively. GNRs (10 mg/mL) were added into two identical phantom solutions, containing 2×10$^{-3}$% of ink and 2% of Intralipid (optical properties of $\mu_a$=0.0115 mm−1 and µs'=1.6 mm−1) to achieve final concentrations of 0.03 and 0.008 mg/mL of gold in the phantoms. The solutions were heated and mixed at a temperature of approximately 90° C. while the agarose powder was slowly added. Then, the phantom solutions were poured into a 24-well plate (each well with a 16 mm diameter) and were cooled under vacuum conditions.

In Vitro Experiment:

A-431 cells (2.5×10$^6$) in 5 mL Dulbecco's modified Eagle's medium containing 5% fetal calf serum, 0.5% penicillin, and 0.5% glutamine were divided into two groups for a quantitative cell binding study (each experimental group was run in triplicate). The first group was incubated with 50 μL of anti-EGFR-coated GNR (25 mg/mL) for 30 minutes at 37° C., and the second group (negative control) was incubated under the exact same conditions with anti-rabbit immunoglobulin G (IgG)-coated GNR. After incubation, the medium was washed twice with phosphate buffered saline (PBS) followed by the addition of 1 mL of aqua regia HCl:$HNO_3$ (1:3) (Sigma-Aldrich). After evaporation of the acid, the sediment was dissolved in 5 mL 0.05 M HCl. The gold concentrations of the samples were quantified by atomic absorption spectroscopy (AA 140; Agilent Technologies, Santa Clara, Calif.).

In Vivo Experiment:

Embodiments of the present invention for tumor detection were evaluated using mice bearing human head and neck cancer (HNC) derived from an A-431 SCC cell line. A-431 cells ($2 \times 10^6$) were infected subcutaneously into the back flank area of 10-11-week-old nude mice. These cells express from $2 \times 10^4$ to $2 \times 10^6$ EGFRs per cell (Stanton et al., 1994; Todd et al., 1999). When the tumor reached a size of 7-9 mm in diameter, the mice received 100 μL (25 mg/mL) of immune-targeted GNR by tail vein injection. Mice tumor and normal tissue (control #1; identical organ on the opposite side, without tumor, after the GNR injection) were scanned immediately after GNR injection and up to ten hours post-injection.

As a control experiment, the same mice were scanned (tumor and normal tissues) before GNR injection (control #2 and #3, respectively). Diffusion reflection measurements were performed on all samples to test the ability to specifically and sensitively detect tumors. All in vivo measurements were performed under appropriate anesthesia: the mice barrier-controlled facility was under the strict care of the veterinarian in charge of the Institutional Animal Care and Use Committee (IACUC).

Figure 5:
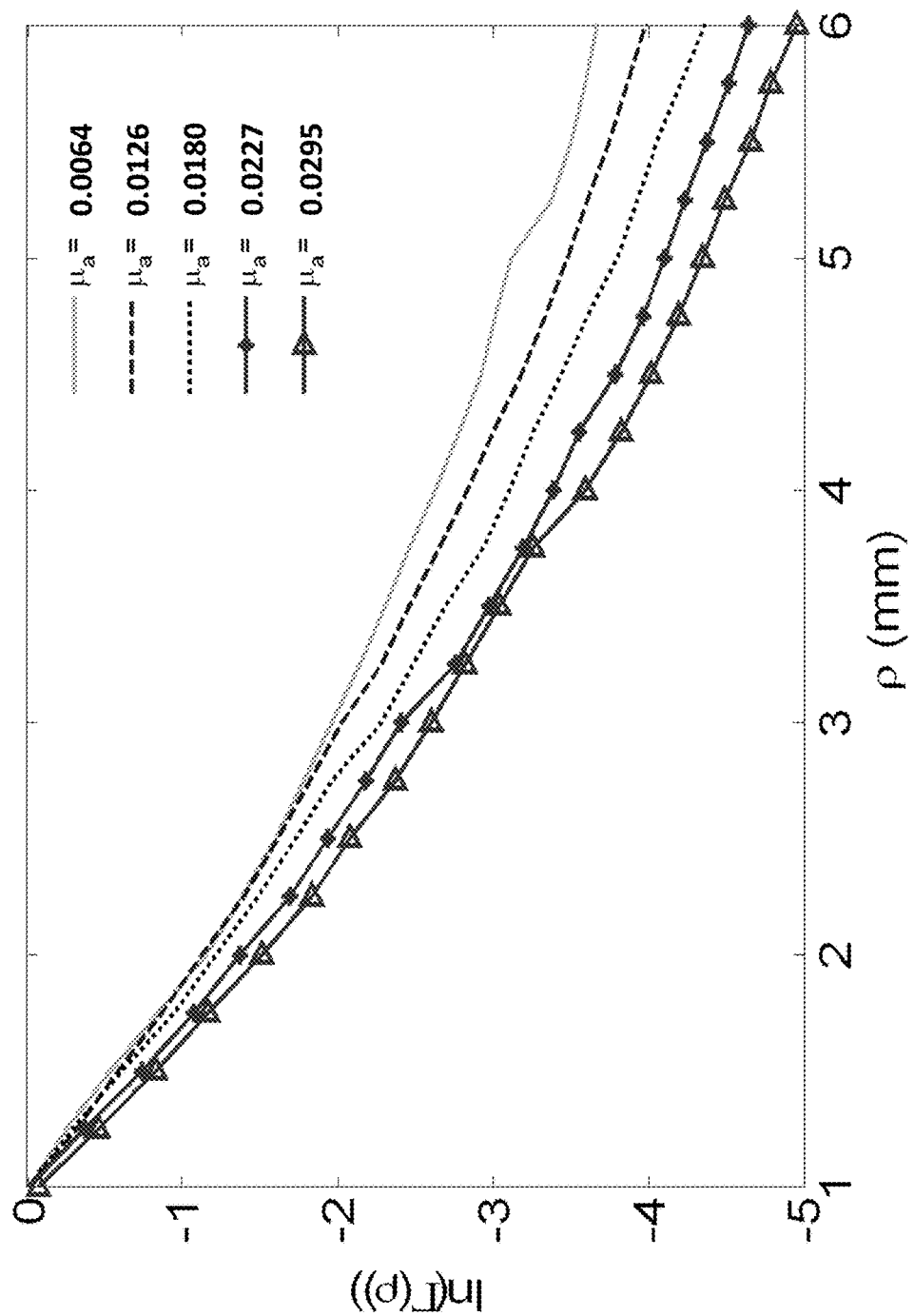
FIG. 5 is a diagram, showing the diffusion reflection intensity (in semi-logarithmic scale) as a function of the distance between the detector and the light source, for different phantoms as follows: a homogeneous phantoms with the same reduced scattering property $\mu s'=1.6$ mm$^{-1}$ but different absorption coefficients of 0.0064, 0.0126, 0.0180, 0.0227, and 0.0295 mm$^{-1}$ (the solid, dashed, dotted, diamond marked, and triangle marked lines, respectively).
Figure 6:
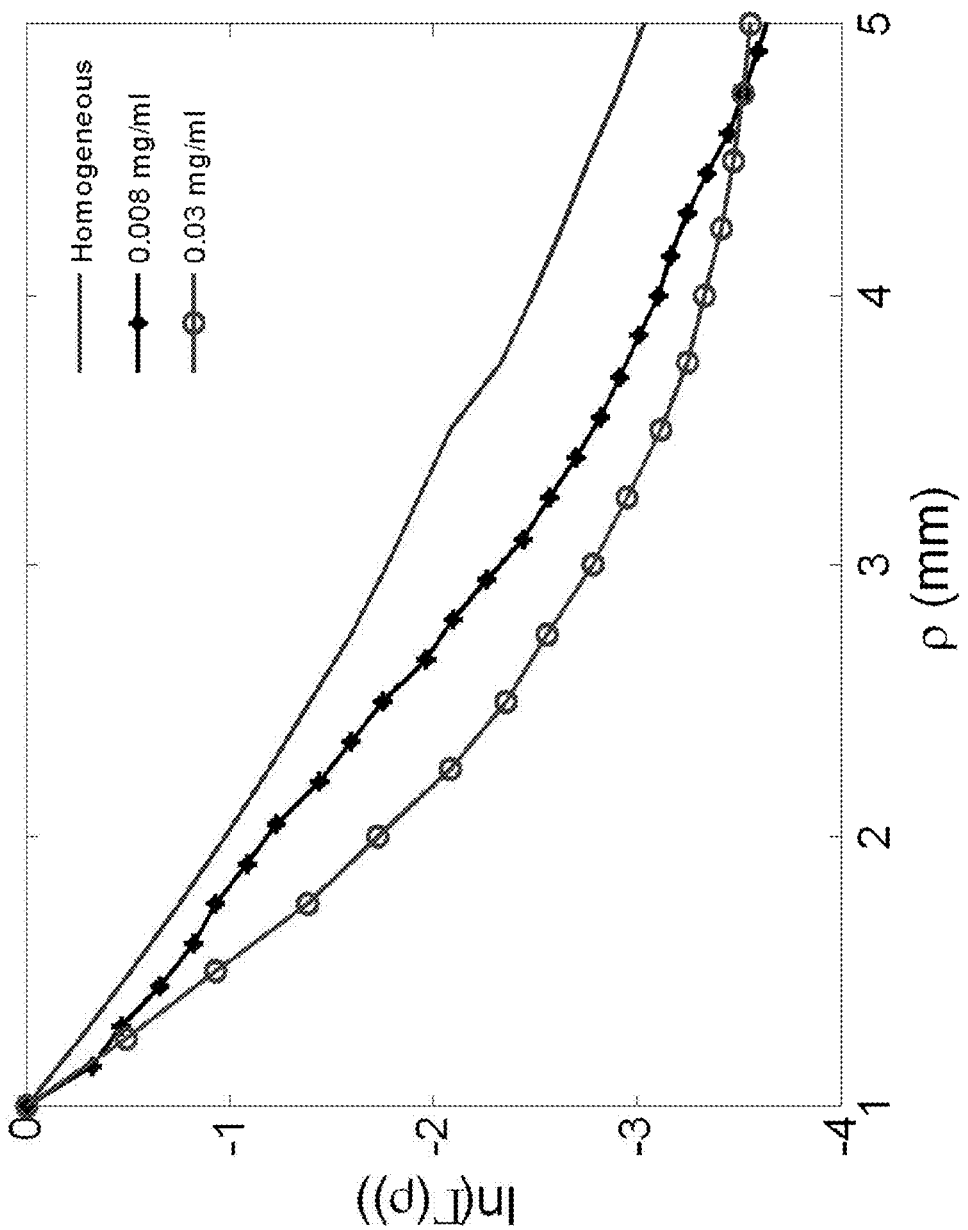
FIG. 6 is a diagram showing the diffusion reflection intensity (in semi-logarithmic scale) as a function of the distance between the detector and the light source, for different phantoms as follows: a homogeneous phantom (the solid line) and phantoms with gold.

Results of Experimental set I:

Phantom Results:

The reflected light intensity from five different phantoms was measured using the experimental setup described above (i.e. in FIG. 2B). Representative results of the reflected light intensity profiles are presented in FIG. 5. The experimental results correlate well with the analytical predictions of the diffusion theory: the larger the absorption coefficient $\mu_s$, the sharper the graph's slope. The phantoms' absorption coefficients were 0.0064, 0.0126, 0.0180, 0.0227, and 0.0295 $mm^{-1}$, and the slopes represent increasing respective negative values of: 0.57, 0.64, 0.69, 0.74, and 0.81. The increasing negative values of the slopes directly correlate with the increasing concentrations of ink in the phantoms. These results Indicate the ability of the system used in the experimental work to clearly distinguish between different absorption coefficients. FIG. 6 presents the reflected light intensity from three solid phantoms as follows: one homogeneous phantom (a solid phantom without GNR, $\mu_s=0.0115$ $mm^{-1}$ and $\mu_s'=1.6$ $mm^{-1}$) and two phantoms containing 0.008 and 0.030 mg/mL of GNR The results clearly indicate that the presence of GNR within the phantom increases the slope of the reflected intensity profile. Moreover, the higher the GNR concentration, the sharper the reflectance graph slope. The phantom with 0.008 mg/mL of GNR represents a negative slope of 1.11, while the phantom containing 0.030 mg/mL of GNR represents a negative slope of 1.39. As mentioned above, GNR have high absorption at 650 nm but negligible scattering properties. Therefore, the observed increase in the graph's slope is due to the increase in the absorption of the irradiated phantom resulting from the presence of the GNR.

In Vitro Results:

To evaluate the specificity of the interaction between the EGFR antibody-coated GNR and the A-431 SCC cancer cells (which highly express the EGFR), two types of GNR were introduced to the cells; the first was specifically coated with anti-EGFR antibody; whilst the second, which was used as a negative control, was coated with a nonspecific antibody (anti-rabbit IgG). Flame atomic absorption spectroscopy measurements quantitatively demonstrated that the active tumor targeting (anti-EGFR-coated GNR) was significantly more specific than the control experiment (anti-rabbit IgG coated GNR). The A-431 cells took up 21.8±2.3 μg of targeted GNR, whilst parallel cells in the negative control experiment absorbed only 0.20±0.01 μg of GNR (Reuveni et al. 2011). These results correlate well with previously published studies, which report that head and neck SCC express from $2 \times 10^4$ to $2 \times 10^6$ EGFRs per cell (Stanton et al 1994).

In Vivo Results:

The tumor-bearing mice were irradiated, under appropriate anesthesia, and the reflected light intensity was measured using the optical, setup described in FIG. 2B, The reflectance measurements were performed before the GNR injection and for several delay times (15 minutes, 3, 5, and over 10 hours) post-injection. The slopes of the reflected light intensity profiles were calculated, and average results are shown in FIG. 7.

Figure 7:
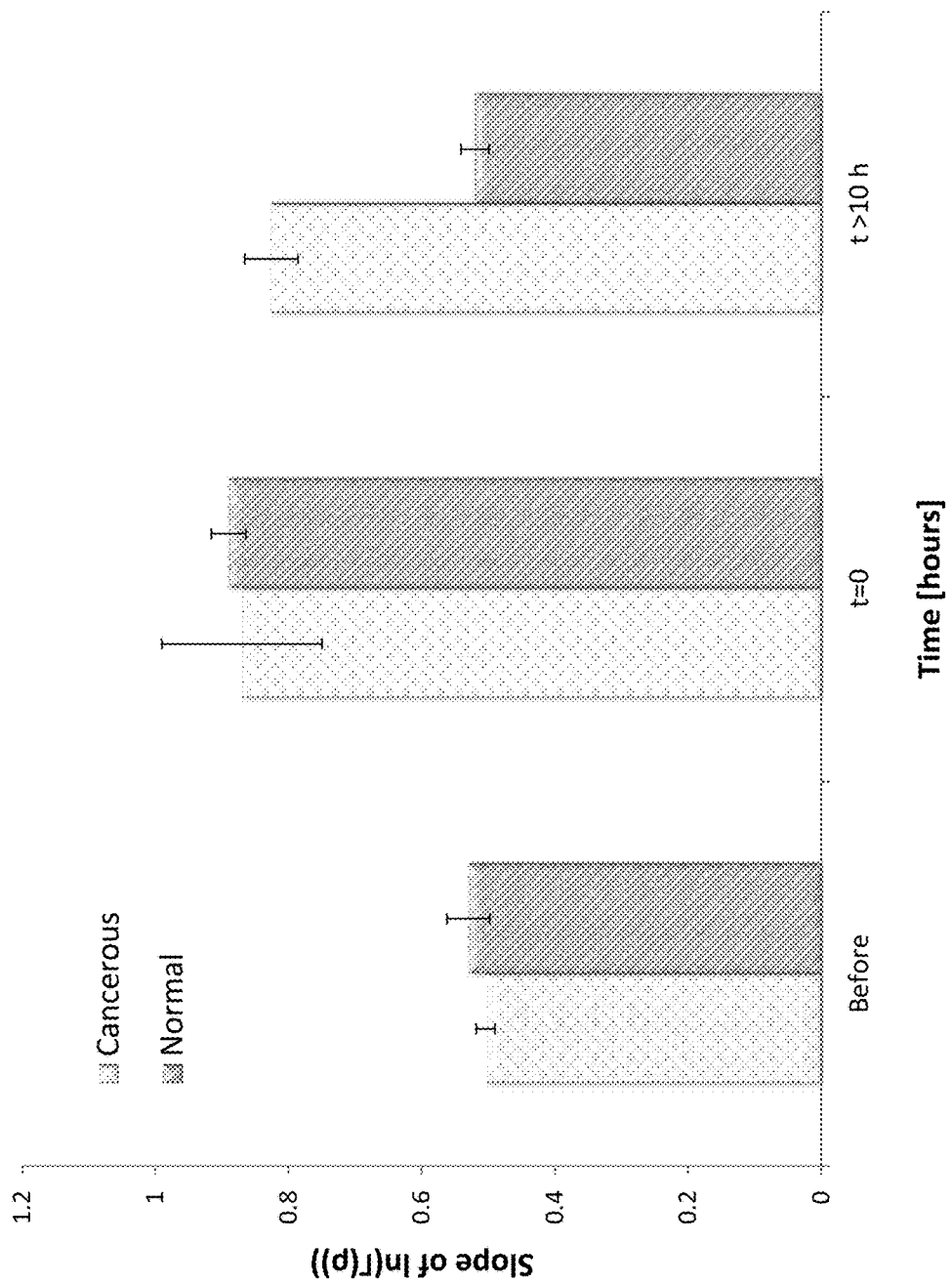
FIG. 7 shows a comparison between the reflected light intensity slopes (absolute values) of the cancerous and normal tissues at several time points. The results are the average of five to ten diffusion reflection measurements of different mice. The error bars represent error of the mean. The highest error bar is of the normal tissue immediately post injection, indicating different rates of the gold nanorod flow in the different mice's blood.

FIG. 7 compares the reflected light intensity slopes (absolute values) of the cancerous and the normal tissues, for three representative times: (1) before GNR injection (control #2 and #3), (2) immediately (~15 minutes) after intravenous injection, and (3) more than ten hours post-injection. It is clearly demonstrated that ten hours post GNR injection there is a significant change (of more than 60%) between the reflectance profiles of the cancerous and the normal tissue (control #1).

This change results from specific accumulation of GNR in the tumor. It is also demonstrated that immediately after GNR injection, as well as for the delay times of three and five hours post-injection (results not shown), the reflectance profiles of both the cancerous and the normal tissues present an increase in their slopes, which indicates the GNR's long circulating time in the blood. After that time, the GNR were gradually cleared from the blood until their complete clearance from the normal tissue, resulting in a decrease of its reflectance slope compared with the cancerous tissue, which kept a stable value of 0.8. Regarding control #3 (normal tissue before the GNR injection), the mice's normal tissues were irradiated in different areas in the mice's skin tissue, and the reflectance slopes of the different areas were almost identical, resulting in a small standard deviation (small error bar in the left column in FIG. 7). This high similarity of these slopes indicates that any non-cancerous area of the skin can be irradiated, and the resulted reflection slope will always be lower than the tumor reflection slope ten hours or more post the GNR injection, enabling consistent tumor detection.

Figure 8:
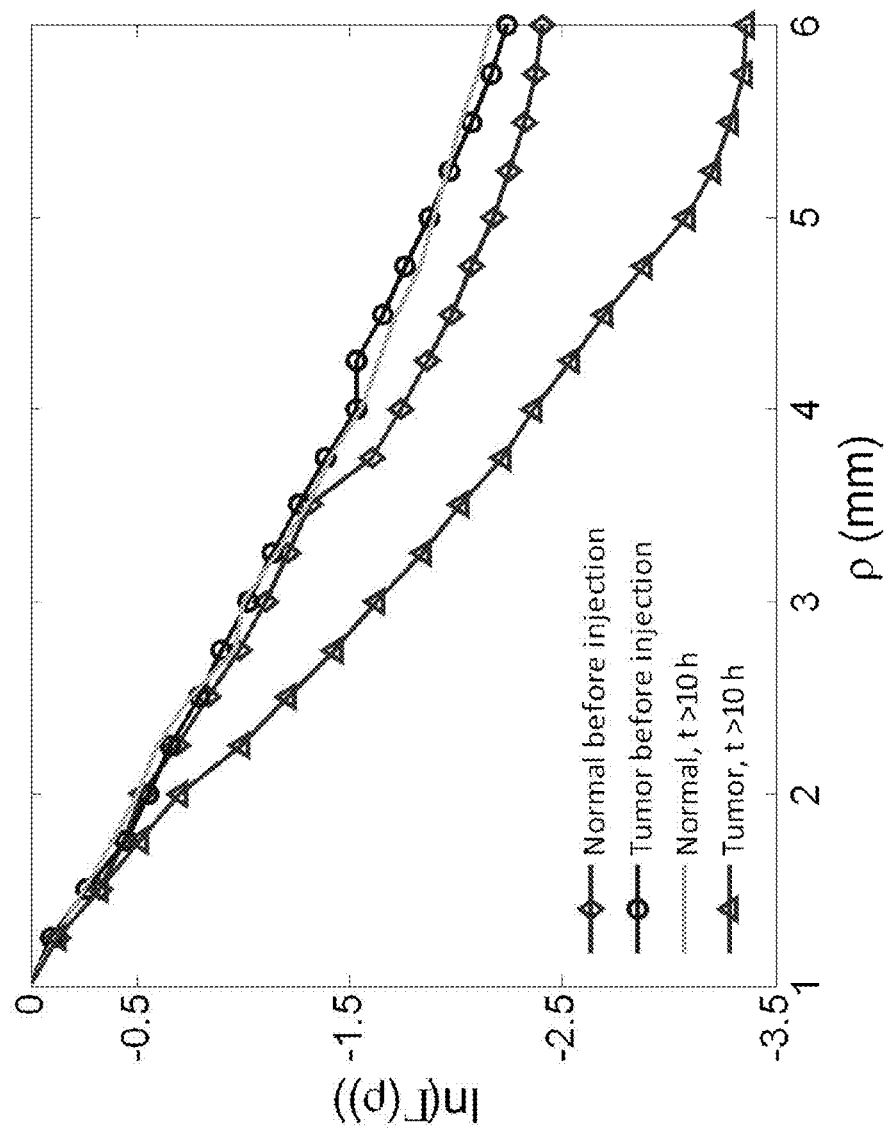
FIG. 8 shows Diffusion reflection intensity (in semi logarithmic scale) as a function of the distance between the detector and the light source. The graph emphasizes the difference between the slopes before GNRs injection and >10 hours post-injection for the cancerous and normal tissues. While the absorption value and the reflectance slope of the normal tissue is the same before GNRs insertion and more than 10 hours post-injection, the tumor clearly presents a higher absorption value resulting in a sharper slope.

FIG. 8 emphasizes the difference between the slopes before GNR injection and more than ten hours post-injection for the cancerous and normal tissues, as directly obtained from the reflected light intensity measurements. While the reflectance slope, which directly indicates the absorption coefficient of the normal tissue, is the same before GNR insertion and more than ten hours post-injection, the tumor clearly represents a sharper slope. This clear discrimination between cancerous and normal tissue enables sensitive and specific cancer detection based on diffusion reflection measurements.

Experiments Set II:
Materials and Methods
The Optical Setup:

In this experiment double-wavelength measurements were performed, where the first wavelength correlates with the absorption peak of the suspended GNR and the second wavelength correlates with the expected extension and red-shift ($\Delta\lambda$) of the GNR's absorption spectrum. For this purpose, a noninvasive optical technique was designed and built for reflected light intensity measurements. The system setup is similar to that described in FIG. 2B.

The set-up included two laser diodes, with wavelengths of 650 nm and 780 nm, which, were optically bundled to a split fiber (125 mm in diameter) for irradiation. A portable photodiode, deposited at different, distances $\rho$ on the samples' surface, served as a detector, enabling DR intensity ($\beta$) measurements in several light-source detector separations ($\Gamma(q)$). The photodiode's cross-section diameter was 1 mm². The initial distance $\rho$ between the light source and the first location of the photodiode was approximately 1 mm. A micrometer plate, to which the optic fiber was attached, enabled a consecutive reflected light intensity measurement. The micrometer plate was moved in 21 incremental steps of 250 µm each. The reflected light intensity was collected from 1 mm. (the initial distance between the light source and the photodiode) to 6.25 mm. The reflected intensity $\Gamma(\rho)$ (in Voltage) was collected using the digital scope (Agilent Technologies, Mso7034a, Santa Clara, Calif.) as well as a DAQ (USB-6008, National Instruments, Israel), The data was processed using the MATLAB (the Mathworks inc., 2010) and Lab View (National Instruments, 2009) softwares.

Figure 9:
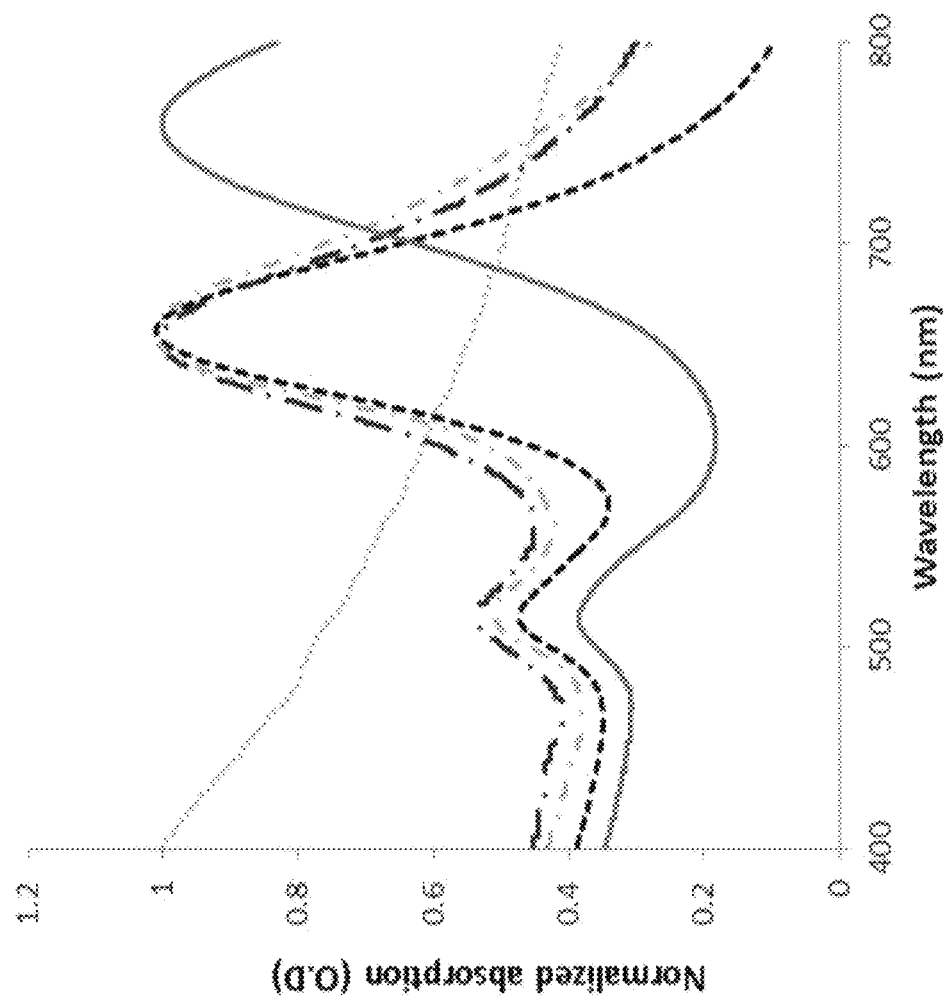
FIG. 9 shows UV-Vis absorption spectra (normalized) of 3% India Ink (dotted line); bare GNR$_{650}$ (25×65 nm, thin dashed line); PEG coated GNR$_{650}$ (thick dashed line); anti-EGFR coated GNR$_{650}$ (dotted-dashed line) and bare GNR$_{780}$ (52×13 nm) (solid line).

Gold Nanorods Fabrication:

Two sizes of GNR types, presenting absorption spectra in 650 and 780 nm, were prepared and the DR method ability to distinguish between their different SPR values was proved. The GNR were synthesized using the seed mediated growth method (Nikoobakht et al., 2003). Their size, shape and uniformity were characterized using transmission electron microscopy (TEM) (FIG. 9) and presented a narrow size distribution (10%). The absorption spectra of the GNR solutions were measured and are presented in FIG. 9. Two kinds of GNR were synthesized; the first, named as $GNR_{650}$, have average dimensions of 65×25 nm, resulting in an aspect ratio "R" of 2.6 and an average effective radius "$r_{eff}$" of 19 am (Jain et al., 2006). These GNR presented an absorption peak at 650 nm. The second kind of GNR, named as $GNR_{780}$, presented average dimensions of 52×13 nm, resulting in R=4; $r_{eff}$=12.5 nm and an absorption peak at 780 nm. According to Jain et al., 2006, these GNR have high absorption properties at 650 nm and 780 nm but much less dominant scattering properties: while $GNR_{650}$ are expected to have an absorption coefficient three times higher than their scattering coefficient, $GNR_{780}$ are expected to present an absorption coefficient that is about 14 times higher than their scattering coefficient.

Only $GNR_{650}$ were used for the in-vivo measurements in order to illuminate with 780 nm laser, according to the expected spectral red-shift.

Solid Phantoms Preparation:

Solid phantoms were prepared and simulated the skin tissue optical properties (Dam et al., 2001). The phantoms were prepared using $3\times10^{-3}$% of India Ink, as an absorbing component, 2% of Intralipid (Lipofundin MCT/LCT 20%, B, Braun Melsungen AG, Germany) as a scattering component (Cubeddu et al., 1997) and 1% Agarose powder (SeaKem LB Agarose, Lonza, USA), in order to convert solution into a gel We determined the absorption spectrum of the India ink (see FIG. 9, dotted line) using a spectrophotometer and calculated the absorption coefficient $\mu_s$ of each phantom according to the concentration of the ink in each solution. The scattering properties of the phantoms were experimentally determined in our previous work. The resulted $\mu_a$ of the phantoms was 0.0137 mm$^{-1}$ and the reduced, scattering coefficient $\mu'_s$ was ~1.45 mm$^{-1}$.

Into six identical phantom, solutions, $GNR_{650}$ (4 mg/mL) were added to achieve final concentrations of 0.01, 0.02, 0.05, 0.1, 0.15 and 0.2 mg/ml of gold. In addition, $GNR_{780}$ (4 mg/mL) were added to another phantom and presented a final concentration of 0.02 mg/ml.

All phantom solutions were heated and mixed at a temperature of approximately 90° C. while the Agarose powder was slowly added. All phantom solutions were poured into a 24 wells plate (each well of a 16 mm diameter) and were cooled under vacuum conditions (to avoid bubbles).

Dark field Reflectance Imaging:

Dark field reflectance images of GNR650 were captured using the hyper spectral imaging system (Nuance, CRi, Mass., USA). A Xenon illumination, along with a 40× dark field objective (0.75 NA) and 32-bit ultrasensitive CCD camera detector (N-MSIEX, CRi, Mass., USA) were used for imaging in RGB (red green blue) mode. Microscopy then was performed on a Nikon 80i Microscope (Nikon instruments, Inc). Images were acquired using the Nuance software version 2.1. In dark field microscopy, a very narrow beam of white light is delivered on top of the sample. The large scattering angle allows detection of highly scattering objects (such as GNR, due to their enhanced SPR) with a very little background signal. We prepared three different concentrations of $GNR_{650}$ solutions as three volumes of 5, 12 and 20 µl were taken from a solution presenting 3.1 mg/ml of $GNR_{650}$. The resultant densities of the $GNR_{650}$, on slides with dimensions of 1 cm², were 0.0155, 0.0372 and 0.062 mg/cm².

In Vivo Experiment:

In-vivo DR measurements were evaluated using mice bearing human HNC derived from an A-431 SCC cell line. A-431 cells (2×106) were injected subcutaneously into the back flank area of 10-11 week-old nude mice. Two concentrations of $GNR_{650}$ were injected into two groups of mice: group 1 received 200 ml of ~10 mg/ml while group 2 received 200 µl of ~30 mg/ml. When the tumor reached a size of live to seven millimeters in diameter, the mice received the $GNR_{650}$ by tail vein injection. Mice tumor and normal tissue were scanned before $GNR_{650}$ injection and ~16 hours post injection. Diffusion reflection measurements were performed on three to five different sites on the mice's skin.

All in-vivo measurements were performed under appropriate anesthesia: the mice barrier-controlled facility was under the strict care of the veterinarian, in charge of the Institutional Animal Care and Use Committee (IACUC), The mice were inspected daily by the veterinarian, who handles the appropriate tests and treatment protocols, as required. All research protocols were followed closely by the veterinarian. Ail major procedures were performed in the surgical facilities using general anesthesia and standard, aseptic surgical techniques.

In this line of experiments it was shown that the key advantage of the DR imaging based detection is that it correlates the absorber's molecules concentration and the irradiated light intensity $\Gamma(\rho)$. This correlation can be used for identifying the tumor's size.

Figure 10A:
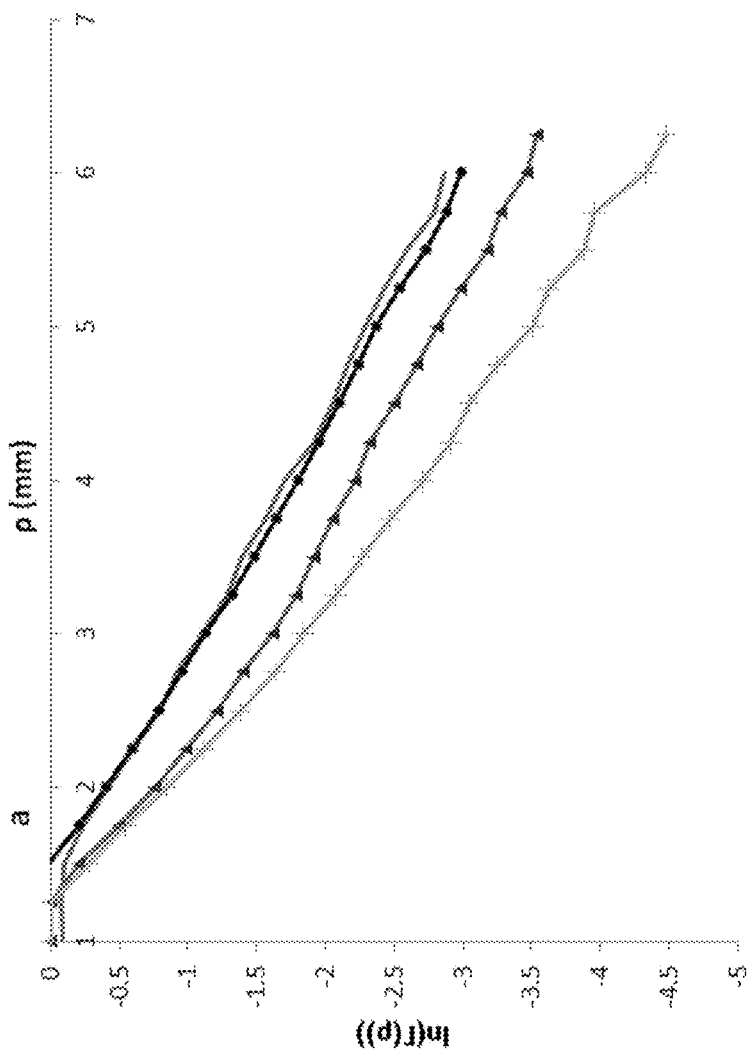
FIGS. 10A-10B show diffusion reflection intensities (in semi-logarithmic scale), as a function of the distance between the detector and the light source, of different phantoms as follows.

Results of Experiments Set II:
DR measurements of Solid Phantoms Containing GNR:

DR measurements of solid phantoms containing both, $GNR_{650}$ and $GNR_{780}$, were performed using the experimental set-up described above. Representative results of the reflected light intensity profiles of a phantom with 0.01 mg/ml of $GNR_{650}$ are presented in FIG. 10A. The experimental results correlate well with the predicted behavior: first, the solid phantom without GNR (named as a homogeneous phantom) presents a DR profile with a more negative slope following 650 nm illumination compared to 780 nm illumination (the slopes were 0.69 and 0.60 for the triangle marked line and solid line, respectively). This is in a good correlation with the ink absorption spectrum presented in FIG. 9, which shows a higher absorption in the 650 nm. While the 650 nm illumination results in a more negative slope (of 0.87, the cross marked line in FIG. 10A) than the homogeneous phantom, the phantom that was illuminated with 780 nm kept a constant slope before and after the 650 nm illumination.

Figure 10B:
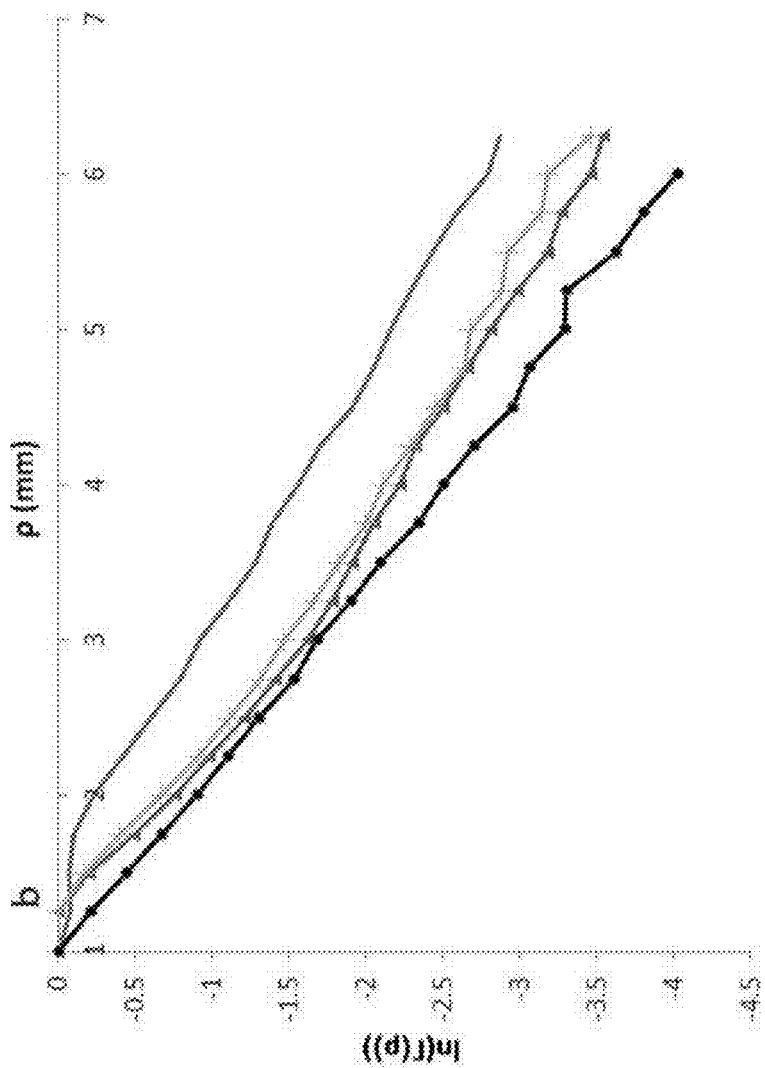

FIG. 10B presents similar results for 780 nm illumination of a phantom, containing 0.02 mg/ml of $GNR_{780}$. While the DR curve following 780 nm illumination presented an increase in its DR slope compared to the phantom without GNR (the slopes values of the circle marked and solid lines were 0.79 and 0.60, respectively). The DR curve following 650 nm illumination remained the same (a slope of 0.63, the cross marked line in FIG. 10B). As mentioned above, these GNR present high absorption properties at 650 and 780 nm but much less dominant scattering properties. Therefore, the observed increase in the graphs' slopes is due to the increase in the absorption of the irradiated phantom, resulting from the presence of the GNR. These results suggest that our detection method can observe different sizes of GNR (based on their different SPRs).

Figure 11:
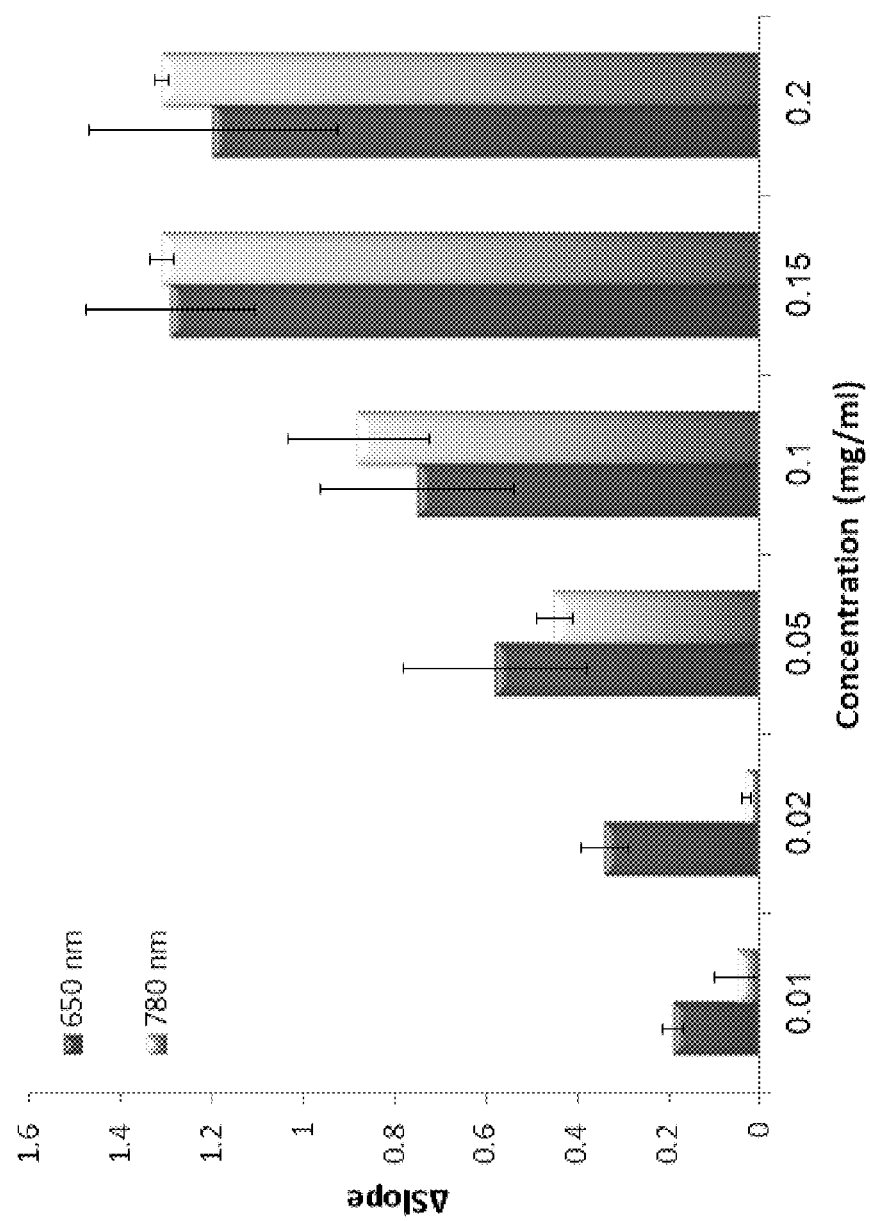
FIG. 11 shows a comparison between the Δ slopes (absolute values) of the reflected light intensity from phantoms containing GNR$_{650}$ following 650 and 780 nm illuminations at different GNR concentrations.

FIG. 11 presents the Δ slopes of all irradiated phantoms, calculated from their DR profiles. The Δ slope is defined as the difference between the DR slopes of a phantom with $GNR_{650}$ and a homogeneous phantom. It is well seen that for low GNR concentrations (0.01 and 0.02 mg/ml in FIG. 11) the DR profiles present, the predicted behavior, as the Δ slopes present significant values following 650 nm illumination only (0.19±0.02 and 0.34±0.05 for 0.01 and 0.02 mg/ml, respectively). Starting from 0.05 mg/ml, the Δ slopes following 780 nm illumination became significant, resulting in 0.45±0.04, 0.88±0.21, 1.3±0.18 and 1.31±0.27 for 0.05, 0.1, 0.15 and 0.2 mg/ml of $GNR_{650}$, respectively. The resulted Δ slopes following 650 nm illumination present similar values of 0.58±0.2, 0.75±0.21, 1.29±0.18 and 1.19±0.27 for the same concentrations, respectively. This similarity in the Δ slopes following both wavelengths irradiation, despite the fact that the phantoms contained $GNR_{650}$ only, indicates that a red-shift and peak expansion occurred in the GNR absorption spectrum. In order to identify this spectral red-shift, dark-field microscopy was used.

Figure 12:
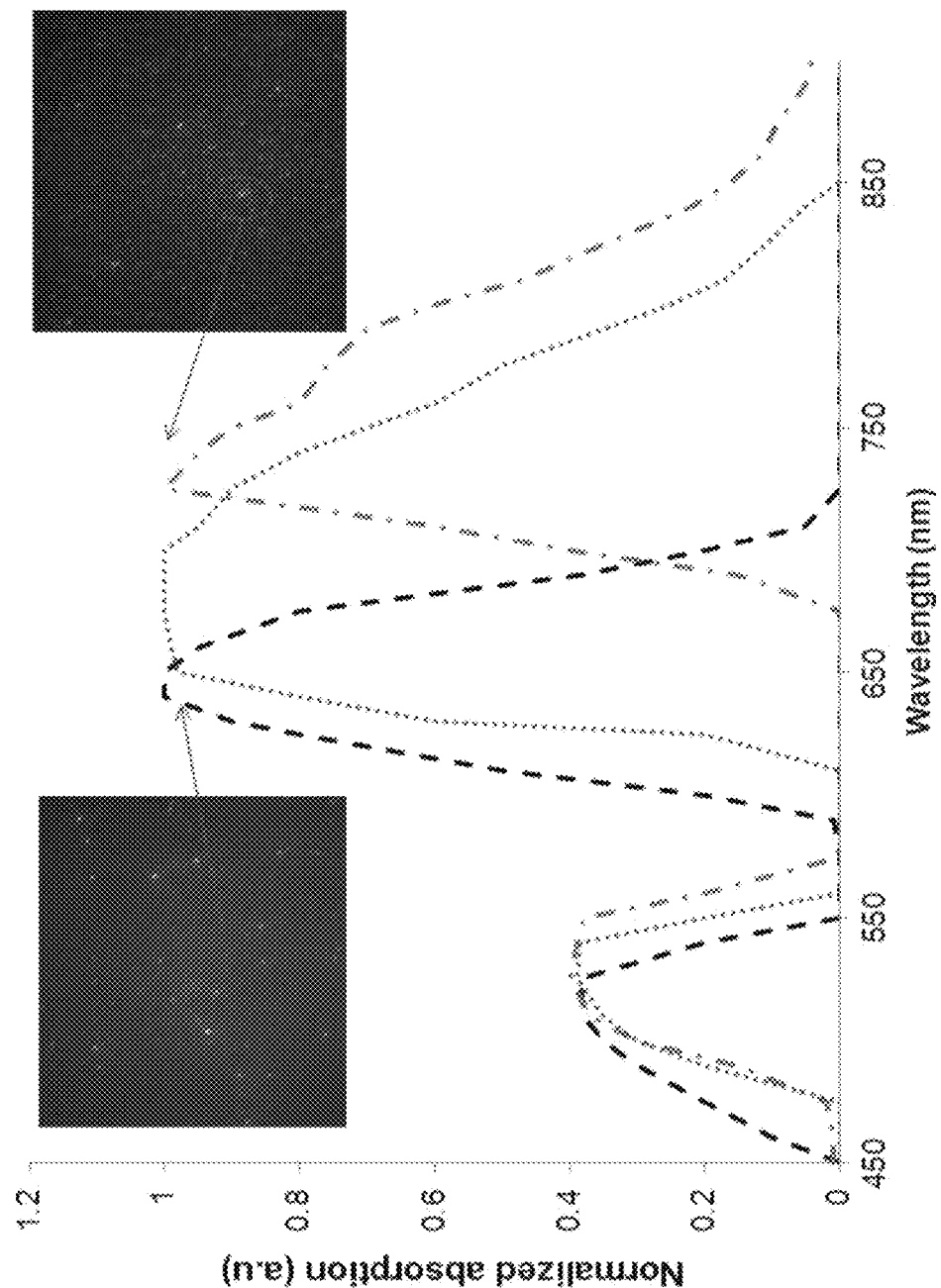
FIG. 12 shows the measured absorption spectra (normalized absorption vs. wavelength) of GNR$_{650}$ from two slides presenting densities of 0.0155 mg/cm$^2$ (dashed line) and 0.0372 mg/cm$^2$ (dashed-dotted line).

In Vitro Dark Field Reflectance Imaging of Different GNR Concentrations:

Different, concentrations of $GNR_{650}$ were measured using the dark-field microscopy and their total absorption spectra were collected, according to the description in the Materials and Method section of Experiment 2, discussed above. The resulted absorption spectra of two different densities, 0.0155 and 0.0372 mg/cm², are presented in FIG. 12. The dashed curve shows the absorption spectrum of $GNR_{650}$ in a relatively low density on the slide, of 0.0155 mg/cm². This spectrum well correlates the absorption properties of the $GNR_{650}$ suspended in water (the dashed line in FIG. 9), presenting a colloidal suspension with high spacing between particles, therefore no red-shift is observed ($\Delta\lambda=0$). The dashed-dotted curve in FIG. 12 is the resulted absorption spectrum of $GNR_{650}$ with a higher density of 0.037 mg/cm². The absorption spectrum still presents the GNR "fingerprint" peak in 530 nm, yet the SPR coupling of the $GNR_{650}$ is well observed as the intense absorption peak shifted to the red region, resulting in an absorption peak of 733 nm ($\Delta\lambda=83$ nm). A larger red shift (to approximately 750 nm, $\Delta\lambda=100$ nm) was observed for $GNR_{650}$ density of 0.062 mg/cm² (data not shown). These results indicate that in high densities of $GNR_{650}$, SPR coupling occurs. It explains the increase in the DR slopes of phantoms with high $GNR_{650}$ concentrations following 780 nm illumination.

Still, since the GNR are not homogeneously dispersed on the slide, the total spectrum should include different. SPR peaks, of 650 nm and of several red shifted peaks toward the 750 nm. Indeed, the dotted line in FIG. 12 shows a broaden graph which was also observed in high densities of $GNR_{650}$ (0.037 and 0.062 mg/cm2). The broadening indicates an inhomogeneous dispersion of the nanoparticles, resulted in an ensemble of red shifts (as was also previously presented by Mallidi et al., 2009). Since the DR slopes of phantoms containing highly concentrated $GNR_{650}$ increased following both, 650 nm and 780 nm illuminations, the possibility that this broadening in the absorption spectrum result from a change in the refractive index of the GNR within the Intralipid surrounding or the tissue was also tested. Simulations and other research were done and suggested that the refractive index of the phantom or tumorous tissue surrounding the GNR do not influence the $GNR_{650}$ SPR. Thus it can be deduced that A slopes presented in FIG. 11, result from the SPR coupling that occurred in the phantoms that contained high concentrations of $GNR_{650}$.

Figure 13A:
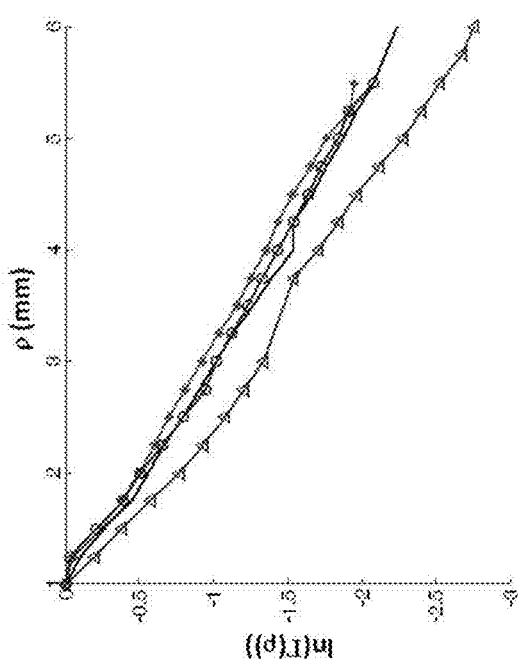
FIGS. 13A-13B show diffusion reflection intensities (in a semi-logarithmic scale) $\ln(\Gamma(\rho))$ as a function of the source-detector separation $\rho$.
Figure 13B:
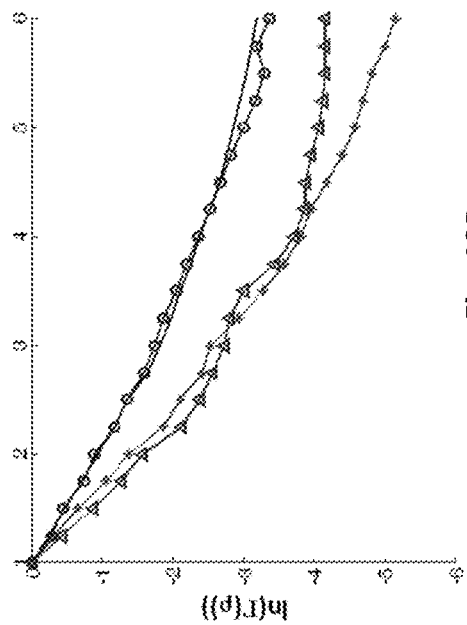

In Vivo DR Measurements of Tumor-Bearing Mice:

The tumor-bearing mice were irradiated, under appropriate anesthesia, and the reflected light intensity was measured using the optical set-up described above. The reflectance measurements were performed before the $GNR_{650}$ injection and approximately sixteen hours post-injection. The slopes of the reflected light intensity profiles were calculated and representative results are shown in FIGS. 13A and 13B. FIG. 13A presents the DR profiles of the tumor bearing mice, group 1. As was mentioned in the Materials and methods section relating to experimental work of experiment 2, this group received a relatively low concentration of $GNR_{650}$. Indeed, the DR spectra presents the same behavior observed for phantoms containing low concentrations of $GNR_{650}$ as the slope of the curve increased following 650 nm illumination only (0.50±0.014 and 0.67±0.02 before and 16 hours post injection, solid and triangle marked lines, respectively), while illumination with 780 nm did not affect the DR slope (an average slope of 0.46±0.042, circle and asterisk marked lines, before and 16 hours post injection, respectively).

In contrast, the DR spectra of group 2, shown in FIG. 13B, present the behavior observed for highly concentrated $GNR_{650}$ in phantoms, as the DR curves show an increase in their slope following both 650 nm (triangle marked line) and 780 nm (asterisk marked line) illuminations compared to their slopes before illumination (solid and circle marked lines, respectively). The average slopes increased from 0.55±0.032 to 0.8±0.009 before and 16 hours post illumination, respectively. These results well indicate that DR measurements can identify a red-shift in tumors in vivo in real time.

Spatial diffusion reflection measurements with GNR as contrast agents is based on the change in the absorption properties of the tumor site following intravenous injection of EGFR targeted GNR. In this above-described experiment 2, the spectral red-shift occurs in high concentrations of GNR was suggested as an additional parameter for DR-based tumor detection measurements.

In the above study, it is well observed that the higher the $GNR_{650}$ concentration, the more intense is the $\Delta$ slope following $780_{nm}$ illumination. In order to verify whether the observed red-shift of the $GNR_{650}$ in phantoms resulted from SPR coupling only, and not from the difference between the refractive indexes of the water and die phantom, the discrete dipole approximation (DDA) method (Draine et al., 2004) was used.

The results suggested that, a very small red-shift of $\Delta\lambda$, of approximately 10 nm, is expected for the $GNR_{650}$ in phantoms or tissues compared to $GNR_{650}$ suspended in water. The expected spectral red-shift of different concentrated $GNR_{650}$ was calculated from in vitro measurements, using the dark-field microscopy. The results, shown in FIG. 12, present a spectral red-shift of $\Delta\lambda=83$ nm in high densities of $GNR_{650}$. This shift was observed while a single GNR (each surrounded by other GNR) was detected. As for a group of GNR, an expansion of the absorption peak was observed, indicating an inhomogeneous dispersion of the GNR.

It was also exhibited (e.g. in FIG. 11) that a broadening in the absorption spectra, as in high concentrations of $GNR_{650}$, the DR slope increased almost identically following both, 650 nm and 780 nm illuminations. If only a red-shift occurred, the DR slopes should introduce an increase in the DR slopes following 780 nm illumination only.

FIGS. 13A and 13B present real-time DR measurements of two groups of tumor bearing mice. The two groups presented different $GNR_{650}$ concentrations in tumor 16 hours post $GNR_{650}$ injection. The results indicate a behavior similar to the observed behavior in FIG. 11: the DR measurements of group 1, which received a low concentration of $GNR_{650}$, showed an increase in their slopes following 650 nm illumination only, indicating that no red-shift occurred in the accumulated GNR in tumor. In contrast, DR measurements of group 2 presented an increase in the DR slope following both, 650 and 780 nm illuminations, suggesting a broadening of the SPR toward the red wavelengths range.

Intravenous administration of targeted GNR results either in a specific binding between the EGFR-targeted GNR and the cancer cells (like SCC), or the inevitable non-specific distribution in the blood and other organs. Further investigation is required in order to demonstrate our ability to distinguish between non-specific and specific (targeted) binding of the functionalized nanoparticles based on their spectral shift. Targeted GNR will present a $\Delta\lambda$ in the tumor site due to their specific attachment to the HNC cells resulting in an inter-particle coupling effect. If there are no cells of interest in the sample, the measured resonant wavelength peak will be the same as of a single GNR. Thus, by screening the skin tissue with a double-wavelength DR set-up, the tumor can be detected.

In conclusion, this section demonstrated in tissue-like phantoms and in vivo mice model that DR imaging can detect the spectral red-shift and the peak broadening that occur in highly concentrated GNR.

Experiments Set III:
Materials and Methods
Monte Carlo Simulation of Reflected Light Intensify from Irradiated Tissues:

In order to substantiate and extend the experimental results, a MC simulation of photon migration within irradiated tissues was built. The simulated tissues presented optical properties that were chosen to skin optical properties (Dam et al., 2001; Cubeddu et al., 1907). A constant reduced scattering coefficient $\mu'_s=1.6$ mm$^{-1}$ and varying absorption coefficients, $\mu_a=0{:}0115$, 0.0126, 0.0182 and 0.0227 mm$^{-1}$, were used. The absorption coefficients just slightly differed from each other, in order to test the sensitivity of the reflected light, profiles to different absorption properties of the tissue. The main assumptions of the simulations were as follows:

(i) A turbid three dimensional medium was defined according to the scattering coefficient $\mu_s$, anisotropy factor g, layer width L and a changing absorption coefficient $\mu_s$. L was set to be 1 meter, much larger than a photon, step "dr". As will be described hereinafter, L>>dr), thus the tissue can be considered infinite. The reduced scattering coefficient $\mu'_s$ was calculated by the following equation: $\mu'=(1-g)\ \mu_s$.

(ii) Photons were launched, without reflection, perpendicular to the surface, into a single point on the lattice plane x=y=z=0.

(iii) For each photon, with a given location ($x_{old}$, $y_{old}$, $z_{old}$) and a propagation direction ($\theta_{old}$, $\varphi_{old}$), the direction ($\theta_{new}$, $\varphi_{new}$) after a step of dr=250 μm was calculated according to the scattering and absorption properties, as follows: (3.1) The probability of a photon to survive was determined by $\exp(-\mu_a \cdot dr)$. (3.2) The probability of a photon to scatter was $[1-\exp(-\mu_a \cdot dr)]$. If the photon scattered, its new direction was calculated: $\theta_{new}=\theta_{old} s_1 \cdot s_2 \cdot \cos(g)$ and $\varphi_{new}=\varphi_{old}+(1-s_1) \cdot s_2 \cdot \cos(g)$. While $S_1$ is a random number from the group $\{0, 1\}$ and $s_2$ is a random number from the group $\{-1, 1\}$.

(iv) If the photon survived, the new location ($x_{new}$, $y_{new}$, $z_{new}$) was calculated using: $x_{new}=x_{old}+dr \cdot \sin\theta_{new} \cdot \cos\varphi_{new}$; $y_{new}=y_{old}+dr \cdot \sin\theta_{new} \cdot \sin\varphi_{new}$; $z_{new}=z_{old}+dr \cdot \cos\theta_{new}$.

(v) When, photons returned to the surface z=0 they were emitted from the system. The locations in which the photons reached the lattice surface (x, y, 0) were saved. The simulation displayed the radial distribution of reflected photons around the injection point to perform simulated $\ln(\rho^2 \Gamma(\rho))$ graphs for the different absorption coefficients.

The Experimental Set-Up:
A noninvasive optical technique was designed and built similar to that described above, in respect to FIG. 2B. The setup included a laser diode with a wavelength of 650 nm as an excitation source. The choice of this wavelength is due to its safety and proximity to the NIR region, in which light can more easily penetrate the tissue. The irradiation was carried out using an optic fiber with a diameter of 125 μm to achieve a pencil beam illumination. We used a portable photodiode as a photo detector. The photodiode was deposited in different distances (source-detector separations) ρ on the sample surface in order to enable $\Gamma(\rho)$ measurements. The photodiode had a cross-section diameter of 1 mm$^2$ and was kept, in close contact with the tissue surface to avoid ambient light from entering the detection system and to avoid potential light loss through the specimen edges. The initial source-detector separation ρ between the light source and the first photodiode was approximately 1 mm.

A consecutive reflected light intensity measurement was enabled using a micrometer plate which was attached to the optical fiber. The micrometer plate was moved by Incremental steps of 250 μm each. As a result, the reflected light intensity was collected from 21 source-detector distances with p varying between 1 mm (the distance between the light, source fiber output and the first photodiode) and 6.25 mm. The reflected intensity $\Gamma(\rho)$, presenting units of Volt per mm, was collected using a digital scope (Agilent Technologies, Mso7034a, Santa Clara, Calif.) and the data was processed using MATLAB designated software.

Solid Phantoms:

Solid phantoms with different, absorption coefficients were prepared in order to simulate skin tissues with different optical properties (Dam et al., 2001). The phantoms were prepared using varying concentrations of India ink 0.1%, as an absorbing component and a constant concentration of Intralipid (IL) 20% (Lipofundin MCT/LCT 20%, B. Braun Melsungen AG, Germany), as a scattering component (Cubeddu et al., 1994), Agarose powder 1% (SeaKem LE Agarose, Lonza, USA) was added in order to convert solution into gel. The absorption spectrum of the India ink was determined using a spectrophotometer and the absorption coefficient of each phantom was calculated according to the concentration of the ink in each solution. All phantoms presented the same scattering properties using 2% of IL (this concentration refers to the solid fraction in the examined solution). The phantoms were prepared in cell culture plates (90 mm) and were cooled in vacuum conditions (to avoid bubbles). The phantoms' solutions were stirred continuously (except for the period in which they were solidified in vacuum) in order to obtain high uniformity.

The optical properties of the irradiated solid phantoms are presented in the following Table 2, Eight different phantoms were prepared. The ink and IL concentrations, as well as the resultant absorption properties of the phantoms, are presented in Table 2. The concentration of IL refers to the fraction of solids in the solution while the concentration of ink pertains to the fraction of the original product.

TABLE 2

|   | Ink concentration [%] | Intralipid concentration [%] | Absorption coefficient $\mu_a$ [mm$^{-1}$] |
|---|---|---|---|
| 1. | $1 \times 10^{-3}$ | 2 | 0.0092 |
| 2. | $1.5 \times 10^{-3}$ | 2 | 0.0104 |
| 3. | $2 \times 10^{-3}$ | 2 | 0.0115 |
| 4. | $2.5 \times 10^{-3}$ | 2 | 0.0126 |
| 5. | $3 \times 10^{-3}$ | 2 | 0.0137 |
| 6. | $4 \times 10^{-3}$ | 2 | 0.016 |
| 7. | $5 \times 10^{-3}$ | 2 | 0.0182 |
| 8. | $7 \times 10^{-3}$ | 2 | 0.0227 |

In addition, GNR (3.1 mg/mL) were added into six phantom solutions, containing different ink concentrations but a constant concentration of IL, as shown in Table 3 below, which shows GNR, Ink and IL concentrations in the phantoms used. Small quantities of GNR were added to the Ink and IL phantoms solutions in order to test the DR method sensitivity to small GNR concentrations.

TABLE 3

| GNR Concentration [mg/ml] | Ink concentration [%] | Intralipid concentration [%] |
|---|---|---|
| 0.002 | $1.5 \times 10^{-3}$ | 2 |
| 0.003 | $1.5 \times 10^{-3}$ | 2 |
| 0.006 | $1.5 \times 10^{-3}$ | 2 |
| 0.008 | $3 \times 10^{-3}$ | 2 |
| 0.02 | $2 \times 10^{-3}$ | 2 |
| 0.088 | $1.5 \times 10^{-3}$ | 2 |

The solutions were heated and mixed at a temperature of approximately 90° C. while the agarose powder was slowly added. The phantom solutions were then poured into cell culture plates (90 mm) and cooled under vacuum conditions.

GNR Fabrication and Targeting:

GNR were synthesized using the seed mediated growth method (Nikoobakht et al., 2003), Their size, shape and uniformity were characterized using transmission electron microscopy (TEM) and the resultant shape was 25 nm×65 nm, with narrow size distribution (10%). In order to prevent aggregation, to stabilize the particles in physiological solutions and to improve blood circulation time, a layer of polyethylene glycol (mPEG-SH, MW 5,000 gr/mol) (creative PEGWorks, Winston Salem, USA) was adsorbed onto the GNR. This layer also provided the chemical groups that are required for antibody conjugations (SH-PEG-COOH MW 3,400 gr/mol). A solution of GNR suspended in cetyl-trimethylammonium bromide (CTAB) (Sigma Aldrich, USA) was centrifuged at 11,000 g for 10 minutes, decanted and resuspended in water to remove excess CTAB. 200 μl of mPEG-SH (5 mM) (85%) and SH-PEG-COOH (1 mM) (15%) were added to 1 ml of GNR solution. The mixture was stirred for 24 hours at room temperature and was dialyzed for three days. The absorption spectrum of PEGylated GNR solution presented a strong peak in 650 nm. The cell targeting was performed using the heterofunctional PEG that was covalently conjugated to the anti-EGFR monoclonal antibody Cetuximab (Erbitux, Merck KGaA, Germany), known to specifically target SCC HNC tumors and to be non-toxic in therapeutic concentrations in humans (Baselga, 2001). The antibody conjugated GNR were stable for up to three months, confirmed by their maintenance of the same plasmon resonance. Also, we found that the PEGylated GNR were highly stable. Zeta-potentials (Maldiney et al., 2011) (ZetaSizer 3000HS, Mai vera Instruments, UK) of the bare GNR showed cationic surfaces ('mV), while the PEGylated GNR showed a nearly neutral surface (−0.5 mV).

In Vivo Experiment:

The method of the invention for tumor detection, was evaluated using mice bearing human HNC derived from an A-431 SCC cell line. A-431 cells ($2 \times 10^6$) were injected subcutaneously into the back flank area of 10-11 week-old nude mice. When the tumor size reached a size of approximately 9 mm in diameter, the mice received 100 μL (25 mg/mL) of immuno-targeted GNR via tail vein injection. The mice tumor was scanned immediately after GNR injection and up to ten hours post-injection.

All in vivo measurements were performed under appropriate anesthesia: the mice barrier controlled facility was under the strict care of the veterinarian in charge of the Institutional Animal Care and Use Committee (IACUC). The mice were inspected daily by the veterinarian, who handles the appropriate tests and treatment protocols, as required. All research protocols were followed closely by the veterinarian. All major procedures were performed in the surgical facilities using general anesthesia and standard, aseptic surgical techniques.

Flame Atomic Absorption Spectroscopy:

The Flame Atomic Absorption (FAA) (AA 140; Agilent Technologies, Santa Clara, Calif.) spectroscopy was used for the evaluation of the GNP concentration in tumor. The tumor was dissolved in Aqua Regia HCl:HNO$_3$ (1:3) (SigmaAldrich, USA) and the resulting solution was warmed to a temperature of 70° C. until the total evaporation of the Aqua Regia. The suspension was then dissolved in 10 ml HCl 0.05 M. The HCl acid was filtered using a 0.45 μm pore size syringe filter (Miller-GC, Millipore Irland LTD, IRL) to remove tissue residues. The filtered HCl solution absorbance was determined using the FAA spectroscopy. The sample was introduced into the flame by conventional aspiration.

Results of Experiments Set III:
Simulation Results:

Simulations of the reflected light intensity from tissues with different optical properties were performed according to the description in the Materials and Methods section above. Photons penetrated and advanced randomly in the tissue. Several absorption coefficients were considered and the resultant logarithmic graphs of the reflected light intensity are shown in FIG. 2(a).

Figure 14:
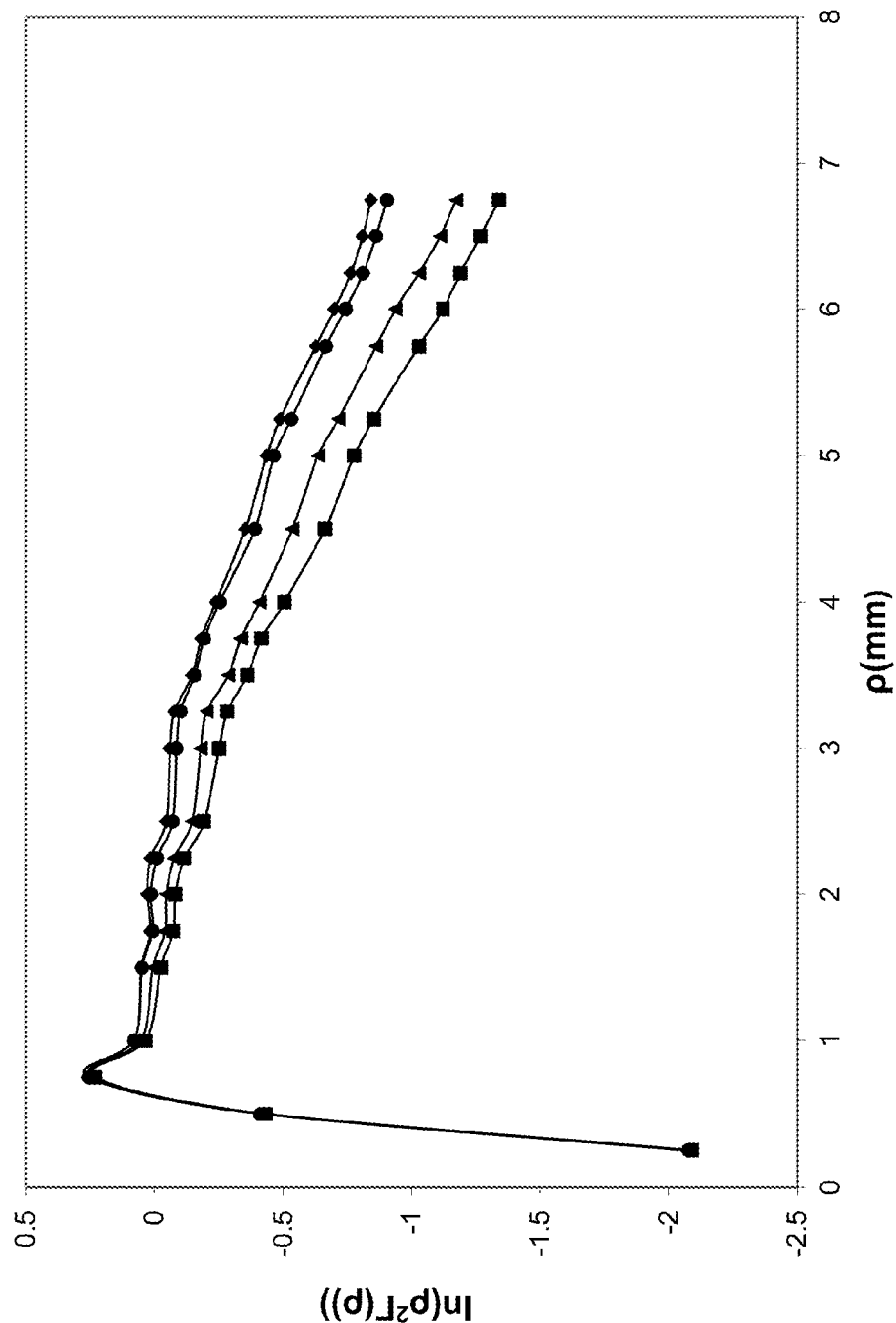
FIG. 14 shows the DR intensity profile results from Monte Carlo simulation: $\rho^2\Gamma$ in semi-logarithmic scale as a function of source-detector separation $\rho$; $\ln(\rho^2\Gamma(\rho))$, for a simulated homogeneous tissue presenting four different absorption coefficients $\mu_a=0.015$ mm$^{-1}$ (diamond marked line); 0.0126 mm$^{-1}$ (circle marked line); 0.018 mm$^{-1}$ (triangle marked line); and 0.0227 mm$^{-1}$ (square marked line).

The simulation results in FIG. 14 present the predicted dependence of the reflected light intensity profile on the lattice absorption coefficient: the higher the absorption coefficient, the sharper the decay of the reflected light intensity profile. This is in agreement with the $\Gamma(\rho)$ equation; $\Gamma(\rho)= [c1/\rho^a]\exp(-\mu\rho)$, in which the absorption coefficient is presented in the exponential decay term. Furthermore, despite the small differences between the absorption coefficients the slopes still differ from each other, resulting in: 0.03, 0.033, 0.054 and 0.084 for the absorption coefficients $\mu_a$ of: 0.0115 mm$^{-1}$, 0.0126 mm$^{-1}$, 0.018 mm$^{-1}$ and 0.0227 mm$^{-1}$, respectively.

Figure 15:
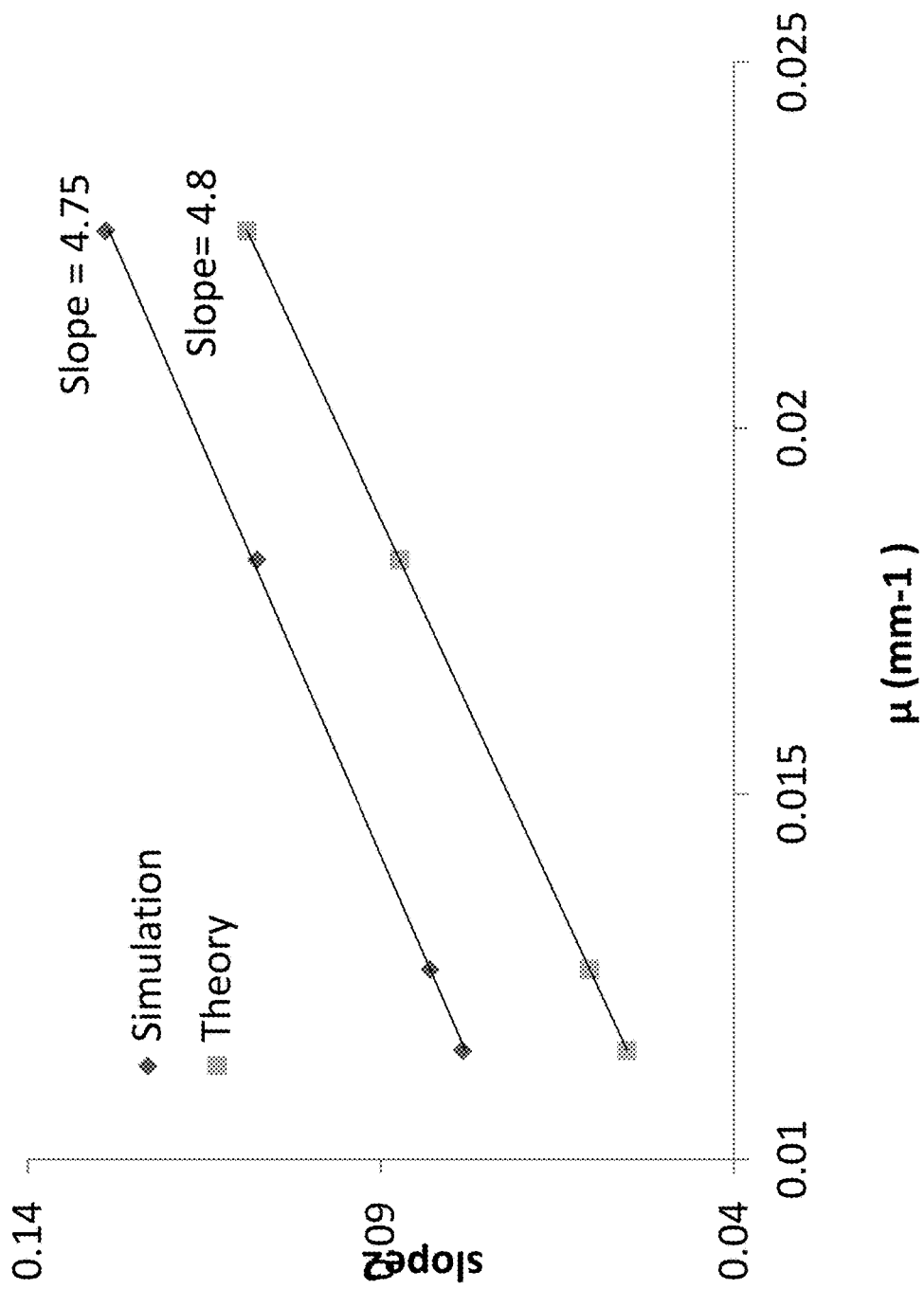
FIG. 15 shows the theoretically calculated and simulated curves indicating the linear dependence of the square slopes of the profile $\ln(\rho^2\Gamma(\rho))$ for the same simulated tissues mentioned in FIG. 14.

FIG. 15 presents the square slopes of $\ln(\rho^2\Gamma(\rho))$ curves versus the varying absorption coefficients $\mu_a$ of all simulated tissues, as well as the predicted square slopes (according to the absorption and scattering coefficients that were inserted into the simulation parameters) calculated from Eq. 2, According to Eq. 2 and 3, the square slope of the resultant linear curve is equal to $3 \cdot \mu'_s$. The simulated linear relation resulting from FIG. 15 was: $(\text{slope}^2) = 4.75 \mu_s - 0.027$. The $\mu'_s$ that was inserted into the simulation parameters was 1.6 mm$^{-1}$, resulting in the theoretical product $3 \cdot \mu'_s$ of 4.8. The resulted slope in the above equation, pointing on 4.75, is almost identical to the theoretical product. Thus, these simulation results suggest that the term $\ln(\rho^2\Gamma(\rho))$ is adequate for the correlation between DR measurements and the optical properties of low absorbing media.

Figure 16:
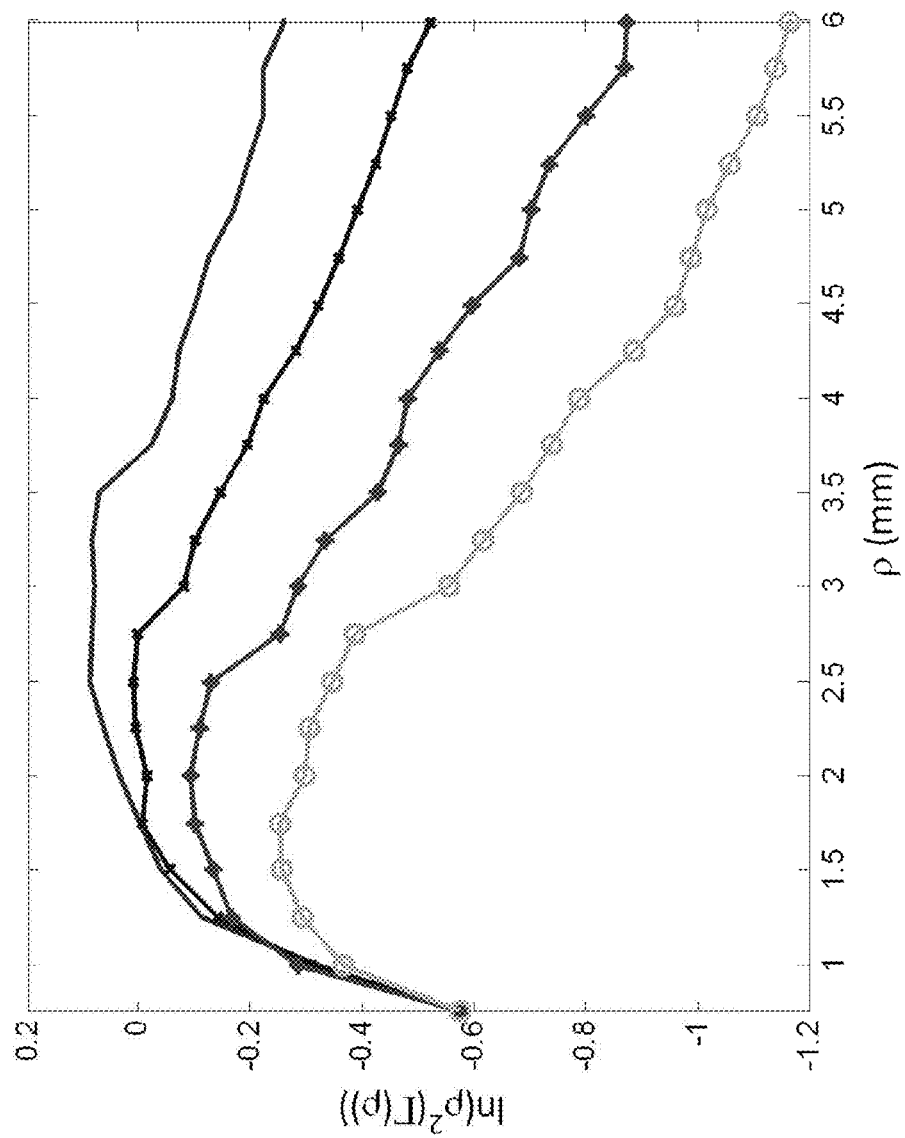
FIG. 16 shows DR profile, $\ln(\rho^2\Gamma(\rho))$, of four tissue-like phantoms having a constant intralipid (IL) concentration, resulting in a constant reduced scattering coefficient, and different ink concentrations resulting in different absorption coefficients of: $\mu_a=0.0115$ mm$^{-1}$ (solid line): 0.01.26 mm$^{-1}$ (marked as "x"); 0.018 mm$^{-1}$ (marked as "*"); and 0.0227 mm$^{-1}$ (marked as "o").

DR Measurements of Solid Phantoms:

The reflected light intensity from eight different solid phantoms was measured using the experimental set-up described above. Representative results of the reflected light intensity profiles, plotted as the logarithm of the product between the square distance and the reflectance versus the distance, are presented in FIG. 16. The experimental results well confirm the analytical predictions of the diffusion theory: the larger μa, the sharper the graph's slope. The phantoms' absorption coefficients were: $\mu_a$=0.0115 mm$^{-1}$ (marked by "◇"); 0.0126 mm$^{-1}$ (marked by circles); 0.018 mm$^{-1}$ (marked by triangles); and 0.0227 mm$^{-1}$ (marked by squares) and their $\ln(\rho^2\Gamma(\rho))$ slopes present increasing respective values (in absolute units) of: 0.003±0.0009, 0.01±0.0005, 0.025±0.0001 and 0.06±0.0002, respectively.

The slopes were calculated from the distance of ρ≈3 mm, where the graphs start a monotonous decay. Some deviations in the slopes values occurred, as presented in FIG. 17, mainly since the resultant phantoms were not totally homogeneous and therefore some variations in their optical properties occurred.

Figure 17:
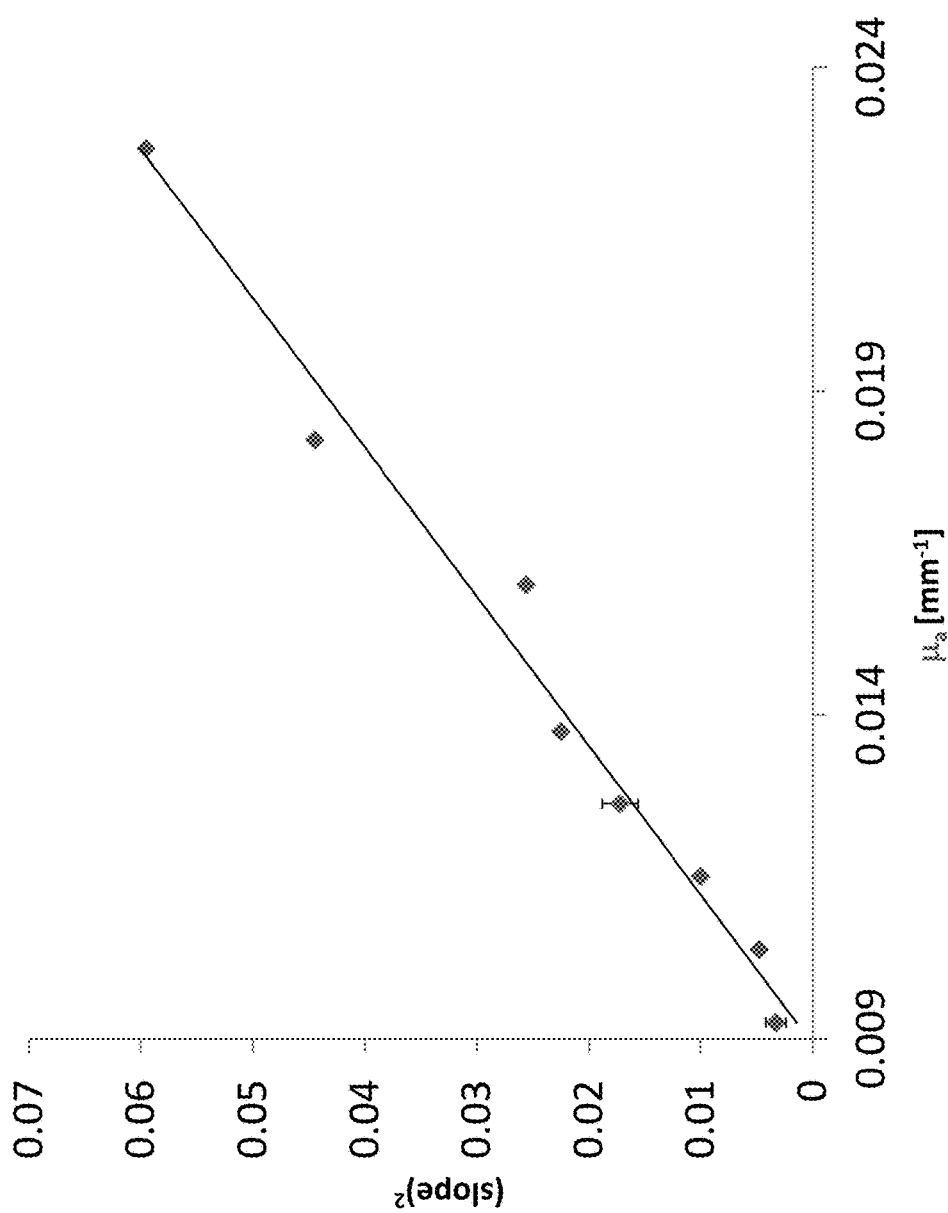
FIG. 17 shows the linear dependence of the $\ln(\rho^2\Gamma(\rho))$ square slopes of solid phantom with different absorption coefficients on the absorption coefficients.

FIG. 17 presents the increasing values of the $\ln(\rho^2\Gamma(\rho))$ square slopes versus the absorption coefficients of the phantoms. The slope of $\ln(\rho^2\Gamma(\rho))$ one gets a simple correlation to the tissue-like phantoms' optical properties. Since the varying component in the phantoms' solutions was the ink (the absorbing component), the square slope of each graph is equal to $3 \cdot \mu'_s$. The resulting equation for the correlation between the square slopes of $\ln(\rho^2\Gamma(\rho))$ and the absorption coefficients of the irradiated phantoms was: $(\text{slope})^2 = 4.35 \mu_a - 0.038$, referred to as Eq. (8).

According to the analytical prediction and our simulation results, the resulted slope of the linear curve, which is equal to $4.35 \cdot \mu'_s$, represents the product $3 \cdot \mu'_s$. The resultant $\mu'_s$ is 1.45 mm$^{-1}$. This is similar to the resultant $\mu'_s$ of phantom containing 2% IL, as was suggested by Cubeddu et al., 1997. Using Eq. (8), the absorption coefficient of any phantom, presenting $\mu'_s$=1.45 mm$^{-1}$, can be deduced from the slope of its reflected light intensity plotted as $\ln(\rho^2\Gamma(\rho))$.

Figure 18:
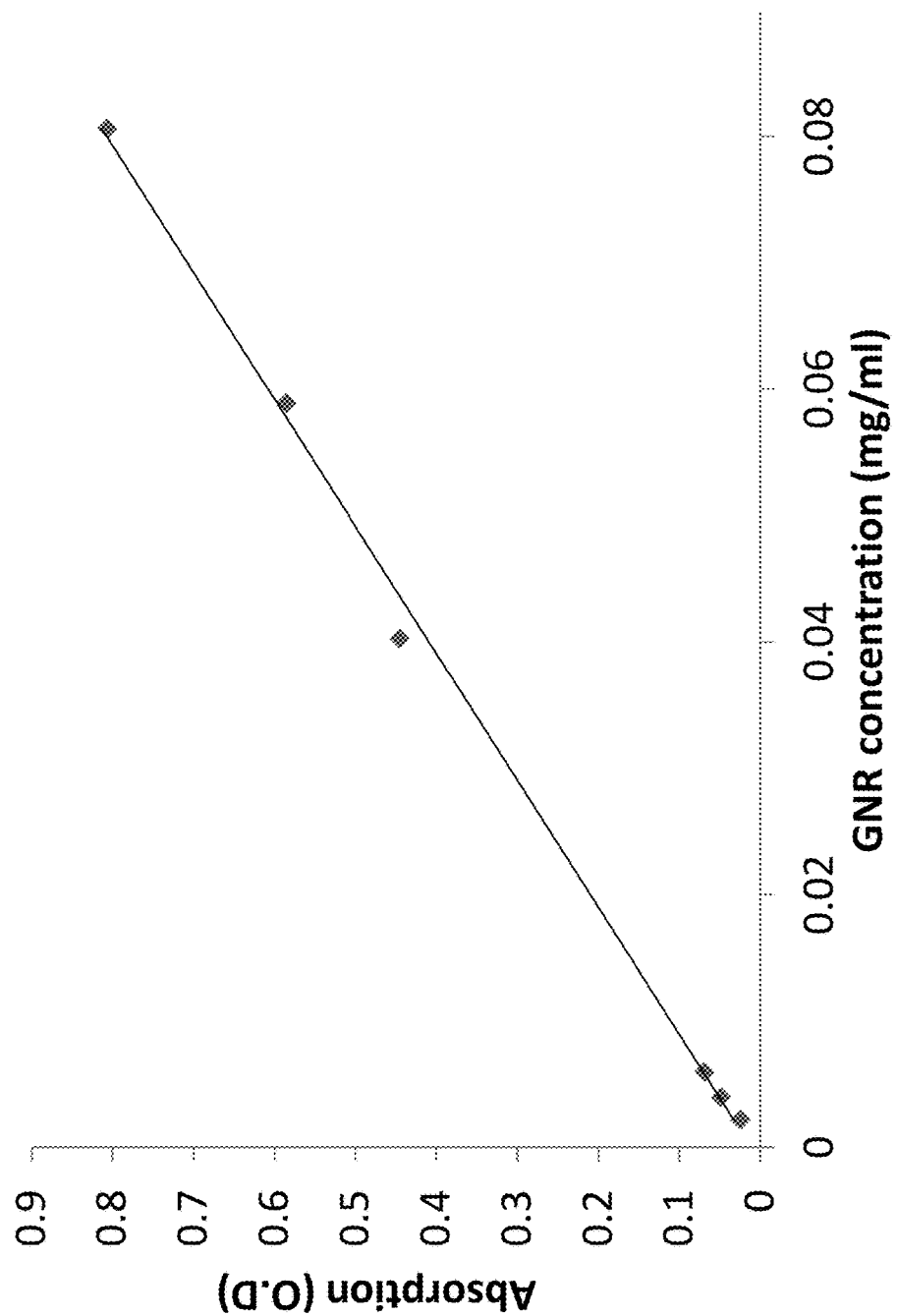
FIG. 18 shows spectrometric results for GNR absorption vs. GNR concentration.
Figure 19:
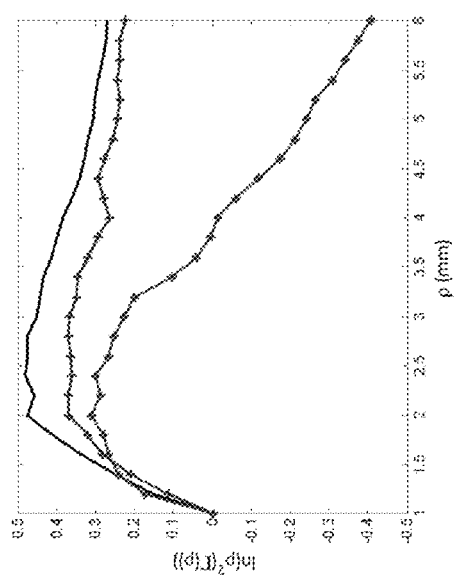
FIG. 19 shows experimental results of the DR measurements for three phantoms containing different concentrations of GNR; 0.0022 mg/ml (solid line); 0.003 mg/ml (marked by "x"); and 0.0057 mg/ml (marked by "*").

DR Measurements of Solid Phantoms Containing GNR:

FIG. 18 presents the absorption spectrophotometer results of GNR solutions (the GNR were suspended in double distilled water) with the varying GNR concentrations of 0.002, 0.004, 0.006, 0.04, 0.06, 0.08 mg/ml. From the graph's slope we found that the mean extinction coefficient of the GNR was approximately 1 ml/(mm·mg). Combining DR measurements of solid phantoms with the GNR optical properties, DR measurements of the six phantoms presented in Table 2 were performed. By multiplying this extinction coefficient with the known GNR concentration, the GNR absorption coefficients in each phantom were calculated. FIG. 19 shows representative results for the DR measurements (plotted as $\ln(\rho^2\Gamma(\rho))$) of three solid phantoms containing 0.002, 0.003 and 0.006 mg/ml of GNR. The results indicate that the higher the GNR concentration, the sharper the reflectance graph's slope. The six phantoms' square slopes of the $\ln(\rho^2\Gamma(\rho))$ profiles are presented in the following Table 4:

TABLE 4

| Calculated $\mu_a$ [mm$^{-1}$] | (slope)$^2$ | Experimental $\mu_a$ [mm$^{-1}$] |
|---|---|---|
| 0.0123 | 0.011 ± 0.006 | 0.012 ± 0.0007 |
| 0.0132 | 0.0143 ± 0.003 | 0.0131 ± 0.0031 |
| 0.0152 | 0.0256 ± 0.003 | 0.0146 ± 0.0007 |
| 0.0216 | 0.0625 ± 0.004 | 0.0229 ± 0.001 |
| 0.0312 | 0.0137 ± 0.006 | 0.0397 ± 0.0004 |
| 0.0986 | 0.042 ± 0.001 | 0.104 ± 0.0002 |

As mentioned in the Material and Method section, the GNR have high absorption at 650 nm but negligible scattering properties in this wavelength. Therefore, the increase in each of the graphs' slopes is due to the increase in the absorption of the irradiated phantom, resulting from the presence of the GNR (since the ink concentration in each phantom has been kept constant).

The absorption coefficients of the phantoms were calculated according to the sum of the GNR and ink absorption coefficient. The resultant total $\mu_a$ of each of the six measured phantoms are presented in the left column of Table 3. The middle column of the table presents the square slopes of $\ln(\rho^2\Gamma(\rho))$ from which the absorption coefficients of each, phantom were calculated. The right, column in Table 3 presents the resultant, absorption coefficients of the irradiated phantoms containing the GNR, as were calculated from the square slopes using on Eq. (8). One can notice the good correlation between the calculated and the experimental absorption coefficient values. These results confirm that the DR measurements can serve for the absorption coefficient extraction of turbid media containing GNR.

Figure 20:
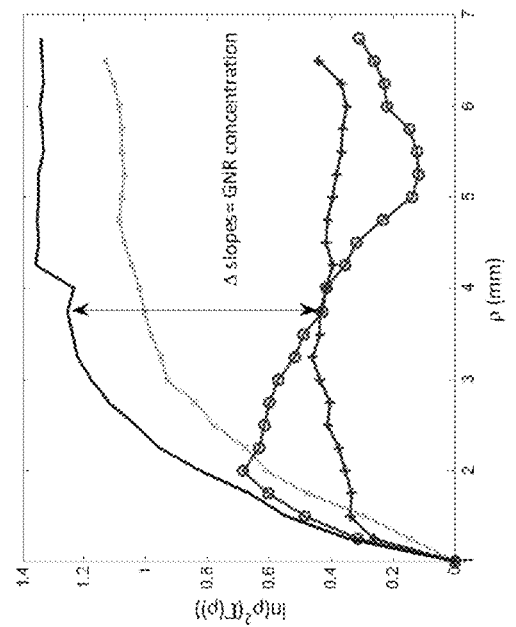
FIG. 20 shows the $\ln(\rho^2\Gamma(\rho))$ curves of the in-vivo DR measurements from the bearing tumor mice. Since the reflectance of tumor before the GNR injection shows a non-decaying behavior, the Δ-slopes of the DR after 5 and 10 hours results from the GNR accumulation in the tumor. Thus, along with the resulted Eq. (8) from the phantoms DR measurements and the GNR extinction coefficient, the Δslopes of the curves can be used for the calculation of the GNR concentration in tumor.

In Vivo Results:

Tumor-bearing mice were Irradiated and the reflected light intensity was collected using the optical set-up described in the Materials and Methods section above. The reflectance measurements of the tumor were performed before the GNR injection and for several delay times post-injection (15 minutes, 5 and 10 hours). FIG. 20 shows representative reflected light intensity profiles as was collected from three mice. Before the GNR injection, no negative slope was observed, pointing on low absorption and scattering properties of the tissue. The slope became sharper after 15 minutes but still not sharp enough for the GNR absorption coefficient calculation. After 5 and 10 hours, the slope of $\ln(\rho^2 \Gamma(\rho))$ was sharp enough for this calculation.

Since before the GNR injection the graph's slope did not present any decay, the slope after 5 and 10 hours directly indicates the GNR accumulation in tumor. As a result, the GNR absorption coefficient was deduced from the change in the graphs' slopes (Δslope) for the different delay times, compared to the slope of the tumor's DR profile before the GNR injection.

Table 5 below shows the Δslopes of the reflected light intensity presented in FIG. 20:

TABLE 5

| Time | Δslope$^2$ | Experimental $\mu_a$ [mm$^{-1}$] |
|---|---|---|
| Before GNR injection | 0 | 0 |
| 15 min post GNR injection | — | — |
| 5 h post GNR injection | 0.0036 | 0.0096 |
| 10 h post GNR injection | 0.0275 | 0.015 |

The GNR absorption coefficients in the different delay times were first deduced by comparing the measured Δslopes with the slopes of the DR curves of the phantoms containing GNR (presented in Table 4).

The measured square Δslope 10 hours post injection was (Δslope)$^2$=0.0275, similar to the square slope of the phantom presenting $\mu_a$=0.015 mm$^{-1}$. As was shown in Table 3, this absorption coefficient also resulted from Eq. (8), which was extracted from the DR measurements of phantoms with a specific scattering (due to the constant concentration of 2% IL). Despite the unknown scattering properties of the mice tumor, the scattering properties of the phantoms were adjusted to skin scattering properties (Dam et al., 2001).

The mice tumors (without GNR) presented a slope similar to the slope of a 'regular' tissue (without tumor, data not shown) therefore, the tumor optical properties can be related to those of the 'regular' tissue. Thus, Eq. (8) can also fit for the calculation of GNR concentration in the tumor.

Accordingly, the absorption coefficient of the GNR in tumor 5 hours post injection was also calculated from this equation and the result was 0.0096 mm$^{-1}$. Using the extinction coefficient of GNR (approximately 1 ml/(mm·mg), see FIG. 18), the GNR concentration in the tumor 5 and 10 hours post GNR injection was 0.0096 mg/ml and 0.015 mg/ml, respectively. As a control measurement, the total concentration of GNR within the tumor was determined using the FAA spectroscopy and the result was 0.0218 mg/ml. Our GNR concentration result 10 hours post injection, calculated using Eq. (8), presents a lower value than the FAA result. This is obvious since the FAA measured the concentration of the GNR present in the entire tumor, on its surface and within the tumor (which was considered as a sphere, with a diameter of approximately 9 mm), while the reflectance measurements presented a maximal length of 6.25 mm and an approximated penetration depth of 9 mm. The DR measurements detected only-part of the GNR concentration in tumor. Still, the slope after 10 hours reflects a high percentage (68%) of the total GNR concentration, indicating an inhomogeneous dispersing of the GNR in the tumor.

In certain embodiments of the invention, the DR method is used for the in vivo detection of arterial vascular disorders such as ASVD, by detection of accumulated of macrophages that uptake metal nanoparticles such as GNPs. This is based on the known finding that phagocyte cells, including macrophages, can uptake metal nanoparticles (Carlson et al., 2008 and Arnida et al., 2011) and since macrophages are major components of the unstable, inflammatory active atherosclerotic plaque (see Lameijer et al., 2013 and Plascencia et. al., 2013), the accumulation of GNPs in an atherosclerotic active plaques is expected. Thus, the combined DR of GNPs presents a new method to detect ASVD at its early stages.

In the below study results we show that the DR method is able to detect, non-invasively, vascular diseases following GNPs injection. We present GNPs uptake by the macrophages (referred to herein also as "golden macrophages") through a preliminary phagocytosis process, as was captured by a hyper spectral imaging system, DR measurements of tissue-like phantoms with macrophages, 24 hours post GNPs injection, demonstrate in vitro that the DR method does detect the golden macrophages. In addition, in vivo DR measurements of carotid arteries in rats, as a model for atherosclerotic vascular diseases, are presented, showing a clear difference between the DR profiles of arteries following vascular injury vs. control arteries. Ex vivo high resolution CT measurements clearly prove the GNPs accumulation within the rat arteries, confirming the DR results.

Experimental Settings:

Macrophages Cells Preparation

Human peripheral blood mononuclear cells (PBMCs) were isolated from BUFFY COAT donated from healthy blood donors (from Sheba, Tel Hashomer Hospital Blood Bank, Ramat Gan, Israel) by density-gradient centrifugation on Ficoll-Hypaque. Monocytes were purified by adherence to plastic in RPMI 1640 supplemented with 10% fetal bovine serum (FBS) and antibiotics. PBMCs (106 cells ml) were first seeded into 24-well plates (0.5 ml per well), after 2 hours, non-adherent cells were removed by several washes with warm PBS. Freshly isolated monocytes were differentiated into macrophages in complete RPMI1640 supplemented with human recombinant macrophage colony stimulating factor (100 ng/ml) for 6 days. To confirm macrophage cell lineage, direct immunostaining was performed with antibody directed against cd11b/mac1 (Biolegend Inc., San Diego, Calif., USA), 80% of positive staining was observed both by flowcytometry analysis and by inverted microscop analysis (data not shown). Macrophages cell culture viability was measured by using the MTT viable test kit (Sigma, St. Louis, USA) according to the manufacturer's protocol.

Balloon Injury of Carotid Arteries in Rats as a Model for Atherosclerosis

We used a standard technique for rat carotid artery balloon injury (Tulis, 2007a). Adult male Wistar rats (Charles River, Mass., USA) weighing 400 g were anesthetized with pentobarbital (50 mg/kg intraperitoneally) to cause a balloon injury of the rat carotid artery. Heparin (35 IU) was administered systemically by intraperitoneal injection. The left external carotid artery was injured using a 2F Fogarty embolectomy catheter to be introduced into the common carotid artery through the external carotid, inflated to 2 atmospheres and withdrawn three times. The catheter was removed and the incision hole was ligated. Perfusion was restored in the common carotid and the neck incision was closed using 4-0 silk sutures. Carotids were collected 7 and 14 days post injury (after intraperitoneal injection of a lethal dose of pentobarbital), included in cryomatrix (OCT), and frozen at −80° C. 12-μm cross-sections were made from the entire length of the carotid and were used for immunohistochemistry analysis (Tulis, 2007b; Keuylian et al., 2012). DR measurements were performed on both groups 2 weeks after artery balloon injury. Immunohistochemistry analyses were also performed to evaluate inflammatory cell accumulation and the results presented at FIGS. 25A-25B.

Gold Nanoparticles Fabrication

Two types of gold nanoparticles (GNRs) were utilized: gold nanospheres (GNSs) and gold nanorods (GNRs). 30 nm GNS were prepared using sodium citrate, according to the methodology described by Enüstun and Turkevich (1963). Particle size, shape, and uniformity were measured using transmission electron microscopy and proved to be 30 nm diameter spheres with narrow size distribution. The PEG layer consisted of a mixture of thiol-polyethylene-glycol (mPEG-SH) (~85%, MW ~5 kDa) and a heterofunctional thiol-PEG-acid (SH-PEG-COOH) (~15%, MW ~3.4 kDa) (Creative PBGWorks, Winston Salem, N.C.).

The GNRs were synthesized using the seed mediated growth method (Nikoobakht et al., 2003). Their size, shape and uniformity were characterized using transmission electron microscopy (TEM). The resultant average shape was 52×13 nm, with narrow size distribution. The GNRs extinction coefficient spectrum was determined using a spectrophotometer, and the resultant extinction peak was 780 nm. A solution of GNRs suspended in cetyltrimethylammonium bromide (CTAB) (Sigma-Aldrich, USA) was centrifuged at 11,000 g for 10 min, decanted and resuspended in water to remove excess CTAB. In order to prevent aggregation, and to stabilize the particles in physiological solutions, a layer of polyethylene glycol (mPEG-SH, MW 5,000 gr/mol) (creative PEGWorks, Winston Salem, USA) was adsorbed onto the GNRs. A 200 µl mixture of mPEG-SH (5 mM) (85%) and SH-PEG-COOH (1 mM) (15%) was added to 1 ml of GNRs solution. The mixture was stirred for 24 hours at room temperature. The absorption spectrum of PEGylated GNRs solution presented the same absorption peak in 780 nm (data not shown). The GNRs were chosen as contrast agents for the tissue-like phantoms and the in vivo experiments since they present the strongest absorption properties, rather than GNS or gold nanoshells.

The Optical Setup

Hyper Spectral Imaging System

Brightfield images of GNRs and vascular tissues were captured using the hyper spectral imaging system (Nuance, CRi, Mass., USA). A Xenon illumination (UN2-PSE100, Nikon, Japan), along with 40× objective (0.75 NA) and a 32-bit ultrasensitive CCD camera detector (N-MSI-EX) were used for imaging in RGB mode. Microscopy was then performed with a Nikon 80i Microscope (Nikon Instruments, Inc). Images were acquired using tire Nuance software version 2.1.

Setup for Diffusion Reflection Measurements

A noninvasive optical technique was designed and built (NEGOH-OP TECHNOLOGIES, Israel) for diffusion reflection (DR) measurements, as was previously described in Ankri et al., 2012a, 2012b, 2011 and in U.S. patent application Ser. No. 14/149,925, to which the present application is a OP. The setup included a laser diode with wavelengths of 650 and 780 nm as an excitation source. Irradiation was carried out using a 1.25 µm diameter optic fiber to achieve a pencil beam, illumination. A portable photodiode was used as a photo detector. The photodiode was kept in close contact with the tissue surface to prevent ambient light from entering the detection system and to avoid potential light loss through specimen edges. The distance between the light source and the photodiode is ρ, and the initial distance was ~1 mm. A consecutive reflected light intensity (Γ) measurement was enabled using a micrometer plate which was attached to the optical fiber. The micrometer plate was moved by incremental steps of 250 µm each. As a result, the reflected light intensity was collected from 20 source-detector distances with ρ varying between 1 mm and 5 mm. The reflected Intensity Γ(ρ), presenting units of Volt per mm, was collected using a digital scope (Agilent Technologies, Mso7034a, Santa Clara, Calif., USA) and data was processed using the Lab View program.

CT Measurements:

All scans were performed using a micro-CT scanner (Skyscan Model 1176). In vivo scans were performed at a nominal resolution of 8.5 microns employing an applied x-ray tube voltage of 50 kV, source current of 500 µA and 0.5 mm aluminum (Al) filtering. Ex-vivo (artery) measurements were performed with the following scanning parameters: the source voltage was 40 kVe, a source current of 600 µA, a pixel size of 12.12 µm and no filtering was used.

Tissue-Like Phantoms

Solid phantoms with different absorption coefficients were prepared in order to simulate skin tissues with different optical properties. The phantoms were prepared using India ink 0.1%, as an absorbing component and Intralipid (IT) 20% (Lipofundin MCT/LCT 20%, B. Braun Melsungen AG, Germany), as a scattering component using methods described in Cubeddu (1997). All phantoms presented the same ink and IL concentrations. Agarose powder 1% (SeaKem LE Agarose, Lonza, USA) was added in order to convert solution into gel. The solutions were heated and mixed at a temperature of approximately 90° C. while the Agarose powder was slowly added. The phantoms were cooled in vacuum conditions to avoid bubbles. The phantoms' solutions were stirred continuously (except for the period in which they were solidified in vacuum) in order to obtain high uniformity. Four types of solid phantoms were prepared: homogeneous phantoms, containing ink and IL only, phantoms with 0.2 mg/ml GNRs, phantoms with about $2 \cdot 10^6$ cells/ml macrophages cells and phantoms with macrophages cells post 24 hours incubation with GNRs. The phantoms with the macrophages were prepared in a 500 µl Eppendorf, in order to keep a significant concentration of macrophages within the phantom.

Results:

Macrophages Uptake of GPN

Figure 21A:
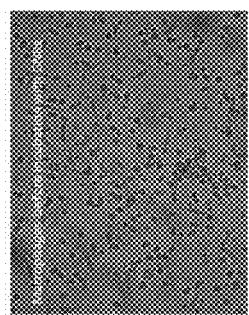
FIGS. 21A-21C show GNS uptake by macrophages captured by the hyper spectral microscopy and are brightfield images of macrophage cells before and after their incubation with two different concentrations of GNS. Nanoparticles appear as dark dots within cells due to light absorption by the particles.
Figure 21B:
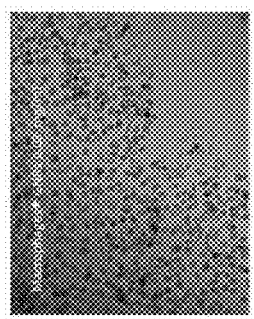
Figure 21C:

The uptake of gold nanospheres (GNS) by macrophages cells was verified using hyper spectral microscopy. A primary human macrophage cell culture was incubated with 50 µL GNS (25 mg/ml) for 24 hours at 37° C. After incubation, the medium was washed twice with phosphate buffered saline and the cells images were captured using the hyper spectral imaging system. FIGS. 21A-21C present pictures of the cells before and after their incubation with two different concentrations of GNS: 0.02 mg/ml and 0.2 mg/ml; FIG. 21A shows the cells before GNRs incubation: FIG. 21B shows the cells with 0.02 mg/ml GNS; and FIG. 21C shows the cells with 0.2 mg/ml GNS. The cellular uptake of the GNS is clearly observed in FIGS. 21B-21C as dark dots that appear within the cells (dots are dark due to the absorption properties of the GNS). These in vitro experiments also demonstrate that the GNS uptake depends on their concentration: for the same amount of cells, the higher the GNS concentration the more dark dots appear within the cells.

Figure 22:
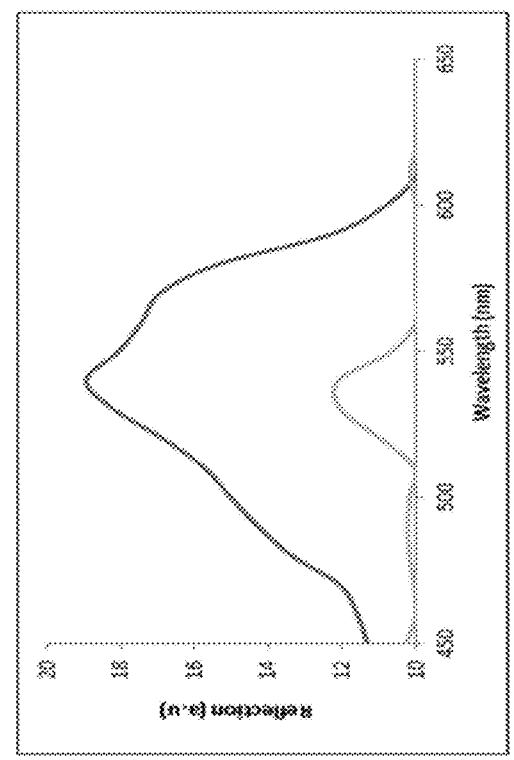
FIG. 22 shows graphs of reflectance intensity from the macrophages of the experiment of FIGS. 21A-21C 24 hours after their incubation with 0.02 mg/ml of GNS (dotted line) and with 0.2 mg/ml of GNS (solid line).

FIG. 22 shows the reflectance spectra of the macrophages after their incubation with the GNS. The spectra ensure the gold uptake by the macrophages, as they are very similar to the absorption spectrum of the GNS, Moreover, the GNS uptake by the macrophages clearly depends on the GNS concentration: the higher the concentration, the higher the reflection intensity.

Diffusion Reflection Measurements of Macrophages within Tissue-Like Phantoms

Macrophages were incubated with gold nanorods (GNRs) (0.2 mg/ml) for 24 hours, then were dissociated from the surface with Trypsin and solidified within tissue-like phantoms. The DR from the phantoms with and without macrophages was measured using our DR system. The phantoms were irradiated with 780 nm illumination, according to the absorption peak of the GNRs (see FIG. 22).

Figure 23:
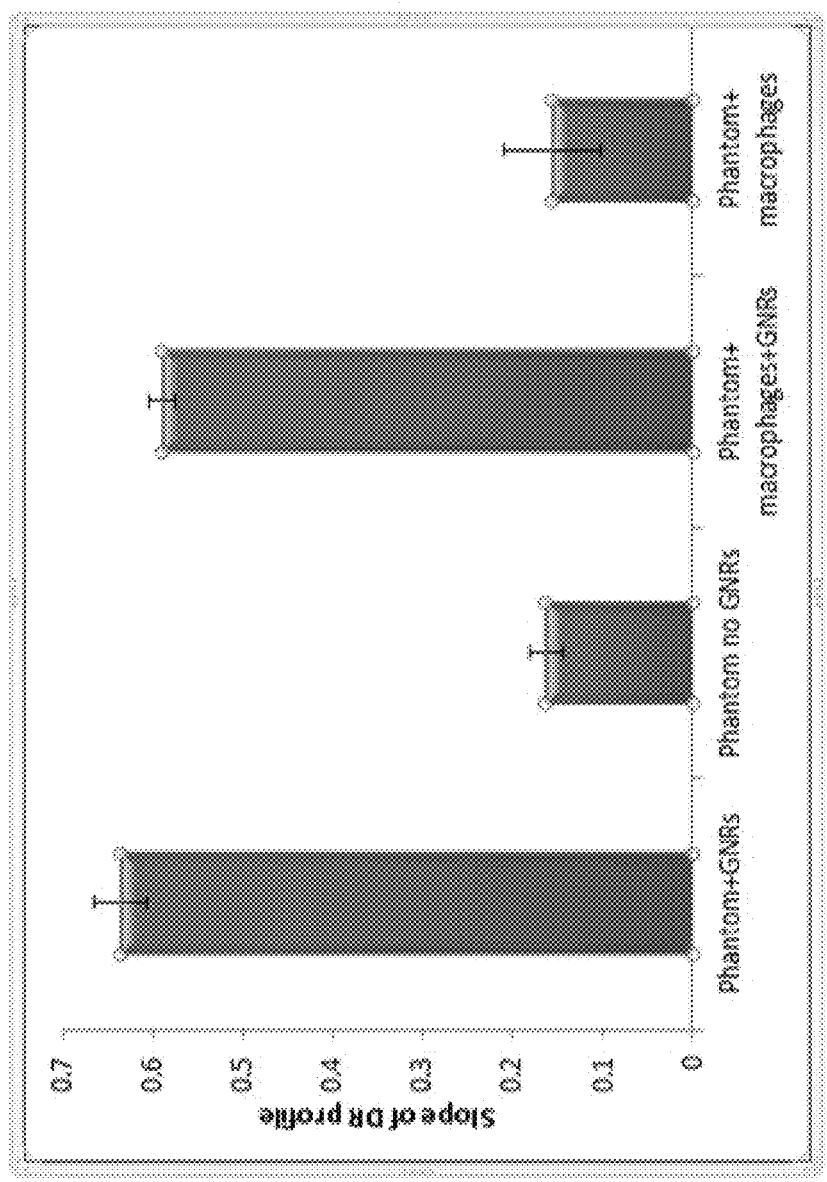
FIG. 23 shows diffusion reflection measurements of tissue-like phantoms. The first and second columns represent phantoms with and without GNRs (0.2 mg/ml), respectively. The third, a phantom with macrophages following their 24 hours incubation with 0.2 mg/ml GNRs. The fourth column represents a phantom with macrophages that were not incubated with GNRs. The slope of the phantom with macrophages that were not incubated with GNRs was very similar to the phantom without GNRs, indicating that the macrophages presence within a tissue does not change the optical properties of the tissue.

FIG. 23 shows DR profile slopes for four types of phantoms: phantoms with GNRs (0.2 mg/ml), phantoms without GNRs, phantoms with macrophages and phantoms with macrophages that were incubated for 24 hours with GNRs. The slope of each reflectance spectrum was extracted (the procedure for the slope extraction is detailed in Ankri et al, 2012) and the average slopes are presented in FIG. 23. It is well noted that the slopes resulting from the DR of phantoms with GNRs are very similar to those associated with the phantoms containing macrophages post GNRs incubation. These results indicate the GNRs uptake by the macrophages and particularly, the capability of the DR method to detect macrophages in tissue-like condition.

Diffusion Reflection Measurements of Rat Carotid Arteries

Figure 24:
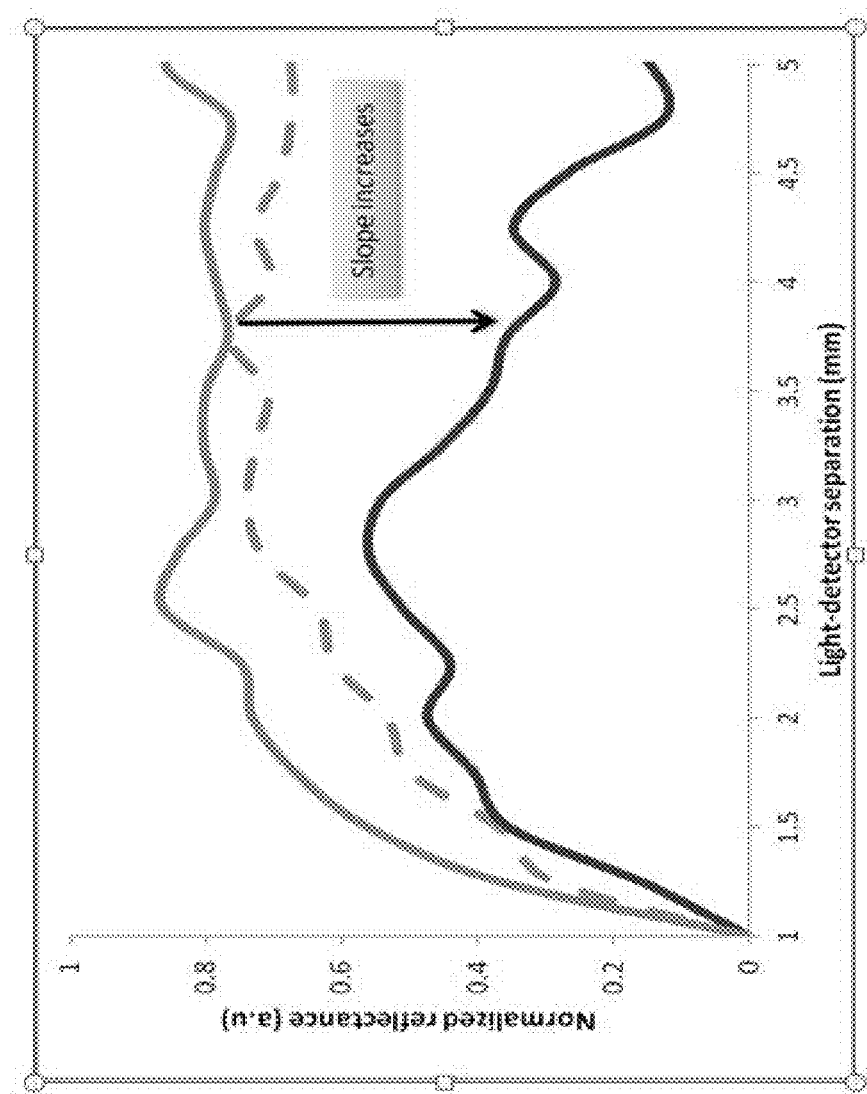
FIG. 24 shows normalized diffusion reflection (DR) of a rat balloon-injured carotid, artery measured by the DR technique used in the present application. The dashed line represents the reflection from the injured artery before the GNRs injection. The dark solid line represents the reflection from the injured artery 24 hours post. GNRs injection, and the solid Sight line the reflection from the non-injured healthy arteries (control). The slopes directly depend on the absorption coefficient of the tissue, correlated with the GNRs concentration within the tissue. Thus, the slope of the injured artery increased following the GNRs administration due to GNRs uptake by the macrophages.

Atherosclerotic vascular disease (ASVD) model in rats was Induced using carotid artery balloon injury (Tulis, 2007a). Immunohistochemistry analyses were performed following the treatment to evaluate inflammatory cell accumulation (see FIGS. 25A-25B)). Rats were scanned in our DR system after a balloon injury of one of their carotid arteries. The injured artery was scanned noninvasively through the rat neck 24 hours post the GNRs injection. Another carotid artery, located in the opposite side of the rat's neck was also scanned and served as a control. In addition, both the injured and the non-injured healthy arteries were irradiated with 650 nm illumination, which is spectrally far from the injected GNRs absorption peak (see FIG. 23). Representative reflectance spectra are presented in FIG. 24. The results clearly demonstrate that the DR method is highly effective in detecting the injured artery, as the reflection slope of the injury artery was about five times higher than the slope of the same artery before the GNRs injection, as well as compared to the non-injured artery.

CT of Rat Carotid Arteries

FIGS. 25A and 25B present high resolution CT images of the arteries of the rat 24 hours post GNRs injection. GNRs along the arteries can be clearly identified, marked as golden regions, since gold induces stronger X-ray attenuation. FIG. 25A shows the CT scan of the injured artery, distorted due to the balloon injury, in the injured region of the artery high concentrations of GNRs were accumulated. The GNR accumulation in this region was likely due to the GNRs uptake by macrophages and other mononuclear cells, known to be recruited and to infiltrate the arterial vessel wall following injury. FIG. 25B depicts a CT image of the healthy non-injured artery, on the opposite side of the rat's neck. Presence of gold can still be observed, but in significantly lower amounts. Importantly, no GNR accumulation in a specific region was observed, suggesting that macrophages did not accumulate in this artery. These CT images strengthen our diffusion reflection results, as both indicate accumulation of GNRs in the injured artery.

The differences between the GNRs spreading in the injured and the healthy arteries are such that while the GNRs in the Injured artery were specifically concentrated in the artery's walls. In the healthy artery GNRs were homogeneously dispersed, indicating the absence of macrophage accumulation. Another important finding is that a regular in vivo CT scan does not reveal GNRs in the injured artery (see FIG. 23), while the DR method did reveal it under the same conditions.

The objective of the present invention, inter alia, is to allow to specifically detect vascular areas with accumulation of macrophages, typical of unstable atherosclerotic plaques. The in vivo model for ASVD was based on a rat carotid artery balloon injury, in which macrophages and other mononuclear cells are recruited and infiltrate the arterial vessel wall following injury. The vascular injury area was specifically identified by GNRs uptake, presumably by macrophages. Our results demonstrate the high efficiency of the DR method, using GNPs, in the detection of macrophages in vitro, and in vascular areas following local injury in vivo. The high resolution CT images (see FIGS. 25A-25B) as well as the histology prove that GNRs can accumulate within vessel walls, as in the injured artery's walls in the current study, causing a change in its optical properties, and thereby, a change in the DR profile of the irradiated tissue. It is Important to note that in contrast to other imaging methods using GNPs, such as for cancer detection such as methods described in Mieszawska et al (2013) and Eissa et al. (2014), there is no need to bio conjugate the GNPs in the detection of ASVD, since the macrophages, known to be a major component of unstable atherosclerotic plaques, uptake pure GNPs. Moreover, in previous embodiments relating to cancer detection we have shown that with the DR method even very small concentrations of GNRs can be detected (see also Ankri et al., 2012b, 2013). Thus, small, early, but inflammatory active atherosclerotic plaques, can be detected in subjects with ASVD at its early stages by the DR method.

The DR method, according to some embodiments of the present invention, is able to detect macrophage accumulation following vascular injury and thus provides a promising novel detection tool for identification of early ASVD and unstable atherosclerotic plaques.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the Invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention Is explicitly contemplated as within the scope of the invention.

The words used in this specification to describe the Invention and its various embodiments are to be understood not only in the sense of their commonly defined meanings, but to Include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

REFERENCES

Ankri R, V. Peretz, M. Motiei et al. "A new method for cancer detection based on diffusion reflection measurements of targeted gold nanorods" Int. J. Nanomedicine, 7, 449-455, 2012(a)

Ankri R, H. Duadi, M. Motiei, D. Fixler, "In-vivo tumor detection using diffusion reflection measurements of targeted gold nanorods—a quantitative study," J. Biophotonics, 5(3), 263-273, 2012(b).

Ankri R, A. Meiri, S L Lau, M. Motiei, Rachela Popovtzer, D. Fixler, "Intercoupling surface plasmon resonance and diffusion reflection measurements for real-time cancer detection" J. Biophotonics, 6(2), 188-196, 2013 (published online 28 Mar. 2012).

Ankri, R., Taitelbaum, H. & Fixler, D. Reflected light intensity profile of two-layer tissues; phantom experiments. *J Biomed Opt* 16, 3605694 (2011).

Arnida, Janát-Amsbury, M. M., Ray, A., Peterson, C. M. & Ghandehari, H. Geometry and surface characteristics of gold nanoparticles influence their biodistribution and uptake by macrophages. *European Journal of Pharmaceutics and Biopharmaceutics* 77, 417-423 (2011).

Baselga J. The EGFR as a target for anticancer therapy—focus on cetuximab. *Eur J Cancer*, 37:16-22, 2001

Biglo I J, Bown S G, Briggs G, et al. Diagnosis of breast cancer using elastic-scattering spectroscopy: preliminary clinical results. *J Biomed Opt*. 5:221-228, 2000.

Bonner R F, R. Nossal, and. Weiss G H, Photon Migration in Tissues, B. Chance (e&) (Plenum, New-York, 1998), pp. 11-23.

Carlson, C, et al. Unique Cellular interaction of Silver Nanoparticles: Size-Dependent Generation of Reactive Oxygen Species. *The Journal of Physical Chemistry B* 112, 13608-33619 (2008).

Cubeddu R, Pifferi A, Taroni P, Torricelli A, Valentini G. A. solid tissue phantom for photon migration studies. *Phys Med Biol* 42: 1971-1979, 1997.

Dagdug L, Weiss G H, and Gandjbakhche A H, *Phys. Med. Biol.* 48, 1361-1370 (2003).

Dam J S, Pedersen C B, Dalgaard T, Fabricius P E, Aruna P, Andersson-Engels S, Fiber-optic probe for noninvasive real-time determination of tissue optical properties at multiple wavelengths. *Appl Opt*. 40:11.55-1164, 2001.

Doornbos, R. M. P., Lang, R., Aalders, M. C, Cross, F. W. & Sterenborg, H. J. C. M. The determination of in vivo human tissue optical properties and absolute chromophore concentrations using spatially resolved steady-state diffuse reflectance spectroscopy. *Physics in Medicine and Biology* 44, 967 (1999).

Draine B T, and Flatau P J. User Guide to the Discrete Dipole Approximation Code DDSCAT 7.0. http://arXivorg/abs/10021505v1 809, 1-79 (2004).

Eissa, S., Shawky, S. M., Matboli, M., Mohamed, S. & Azzazy, H. M. E. Direct detection of unamplified hepatoma upregulated protein RNA in urine using gold nanoparticles for bladder cancer diagnosis. *Clinical Biochemistry* 47, 104-110 (2014).

Enustun, B. V. & Turkevich, J. Coagulation of Colloidal Gold. *Journal of the American Chemical Society* 85, 3317-3328 (1963).

Eustis S. & El-Sayed M. A. Why gold nanoparticles are more precious than pretty gold: Noble metal surface plasmon resonance and its enhancement of the radiative and nonradiative properties of nanocrystals of different shapes. *Chemical Society Reviews* 35 (2006).

Feather J W, Ellis D J, and Leslie G. *Phys. Med, Biol.* 33, 711-722 (1988).

Fixler, D. & Ankri, R. Subcutaneous gold nanorods [corrected] detection with diffusion reflection measurement. *J Biomed Opt* 18, 061226 (2013(a)).

Fixler, D. & Zalevsky, Z. In Vivo Tumor Detection Using Polarization and Wavelength Reflection Characteristics of Gold Nanorods. *Nano Letters* 13, 6292-6296 (2013(b)).

Gobin A M, Lee M H, Halas N J, James W D, Drezek R A, West J L. Near-infrared resonant, nanoshells for combined optical imaging and photothermal cancer therapy. *Nano Lett.* 7: 1929-1934, 2007.

Hielscher A H, Mourant J R, and Bigio I J. *Appl. Opt.* 36, 125-135 (3997).

Huang X, El-Sayed I H, Qian W, El-Sayed AM. Cancer cell imaging and photothermal therapy in the near-Infrared region by using gold nanorods. *J Am Chem Sac.* 128: 2115-2120, 2006.

Jacques S T, Pogue B W. Tutorial on diffuse light transport. *J Biomed Opt.* 13:0413021-0413019, 2008.

Jain P. K., Lee K. S., El-Sayed I. H. & El-Sayed M. A. Calculated Absorption and Scattering Properties of Gold Nanoparticles of Different Size, Shape, and Composition: Applications in Biological imaging and Biomedicine. *J. Phys. Chem. B* 110, 7238-7248 (2006).

Keuylian. Z. et al. The Notch Pathway Attenuates Interleukin 1β (IL1β)-mediated induction of Adenylyl Cyclase 8 (ACS) Expression during Vascular Smooth Muscle Cell (VSMC) Trans-differentiation. *Journal of Biological Chemistry* 287, 24978-24989 (2012).

Kienle, A. et al. Spatially resolved absolute diffuse reflectance measurements for noninvasive determination of the optical scattering and absorption coefficients of biological tissue. *Appl. Opt* 35, 2304-2314 (1996).

Lal S, Clare S B, Halas N J. Nanoshell-enabled photothermal cancer therapy: impending clinical impact. *Acc Chem Res.* 4:1842-1851, 2008.

Lameijer, M. A., Tang, J., Nahrendorf, M., Beelen, R. H. J. & Mulder, W. J. M. Monocytes and macrophages as nanomedicinal targets for improved diagnosis and treatment of disease. *Expert Review of Molecular Diagnostics* 13, 567-580 (2013).

Lin A J, Koike M A, Green K N. et al. "Spatial frequency domain imaging of intrinsic optical property contrast in a mouse model of alzheimer's disease," *Ann. Biomed.* Eng., 39, 1349-1357 (2011).

Lowery A R, Gobin A M, Day E S, Halas N J, West J L. Immunonanoshells for targeted photothermal ablation of tumor cells. *Int J Nanomedicine* 1:149-154, 2006.

Mallidi S, Larson T, Tam J, Joshi PP, Karpiouk A, Sokolov K, and Emelianov S. *Nano Letters* 9, 2825-2831 (2009).

Mieszawska, A. J., Mulder, W. J. M., Fayad, Z. A. & Cormode, D. P. Multifunctional Gold Nanoparticles for Diagnosis and Therapy of Disease. *Molecular Pharmaceutics* 10, 831-847 (2013).

Nikoobakht B, El-Sayed M A. Preparation and growth mechanism of gold nanorods (NRs) using seed-mediated growth method. *Chem Mater.* 2003; 15: 1957-1962

Parmar, J. P. et al. Magnetic Resonance imaging of Carotid Atherosclerotic Plaque in Clinically Suspected Acute Transient Ischemic Attack and Acute Ischemic Stroke. *Circulation* 122, 2031-2038 (2010).

Pham T H, Coquoz O, Fishkin J B. et al. "Broad bandwidth frequency domain instrument for quantitative tissue optical spectroscopy," Review of scientific instruments, 71, (2000).

Popovtzer R. et al. Targeted gold nanoparticles enable molecular CT imaging of cancer. *Nano Lett.* 8, 4593-4596 (2008).

Plascencia-Villa, G., Bahena, D., Rodriguez, A. R., Ponce, A. & Jose-Yacaman, M. Advanced microscopy of star-shaped gold nanoparticles and their adsorption-uptake by macrophages. *Metallomics* 5, 242-250 (2013).

Reuveni T, Motiei M, Romman Z, Popovtzer A, Popovtzer R, Targeted gold nanoparticles enable molecular CT imaging of cancer: an in vivo study. *Int J Nanomedicine* 6:2859-2864, 2011.

Robinson T. J. et al. High Performance In Vivo Near-IR (>1 μm) Imaging and Photothermal Cancer Therapy with Carbon Nanotubes. *Nano Res.* 3, 779-793 (2010).

Schmitt J M, Zhou G X, Walker E C, Wall R T. Multi-layer model of photon diffusion in skin. *J Opt Soc Am A.* 7:2141-2153, 1990.

Shimada M, Sato C, Hoshi Y, Yamada Y. Estimation of the absorption coefficients of two-layered media by a simple method using spatially and time-resolved reflectance. *Phys. Med Biol.* 54:5057-5071, 2009.

Stanton P, Richards S, Reeves J, et al. Epidermal growth factor receptor expression by human squamous cell carcinomas of the head and neck, cell lines and xenografts. *Br J Cancer* 70:427-433, 1994.

Tromberg B J, Coquoz O, Fishkin J B, et al. "Non-invasive measurements of breast tissue optical properties using frequency-domain photon migration," Phil. Trans. R. Soc. Lond. B 352, 661-668 (1997).

Tubs, D. A. Rat carotid artery balloon injury model. *Methods Mol Med* 139, 1-30 (2007(a)).

Tulis, D. in Vascular Biology Protocols, Vol. 139, (eds, N. Sreejayan & J. Ren) 1-30 (Humana Press, 2007 (b)).

Zaccanti G, Alianelli L, Blumetti C, and Carraresi *S. Opt. Lett.* 24, 1290-1292 (1999).

Zhang Q. et al. Gold nanoparticles as a contrast agent for in vivo tumor Imaging with photoacoustic tomography. *Nanotechnology* 20, 395102-339519 (2009).

The invention claimed is:

1. A non-invasive and real-time optical method based on diffusion reflection measurements for detection of arterial vascular disorders or cancer, said method comprising the steps of:
    a) administering to an individual a composition comprising noble metal nanoparticles that accumulate in an injured vascular or cancerous tissue;
    b) optically irradiating an area of a tissue suspected of being a cancerous or injured vascular tissue of the individual with an optical light source outputting an optical signal of at least one wavelength; and
    c) measuring diffusion reflection of said area of the irradiated tissue using at least one detector configured for detecting light reflecting from said area of said irradiated tissue and a processing unit for receiving output data from said at least one detector in real time and processing thereof; whereby
    detection from the measured diffusion reflection of accumulation of the noble metal nanoparticles in said area indicates that the irradiated tissue is an injured vascular or cancerous tissue.

2. The method according to claim 1, wherein measuring of the diffusion reflection is carried out by detecting the changes in intensities of the area of the irradiated tissue for different distances between said light source and said at least one detector.

3. The method according to claim 1, wherein said irradiation is carried out with a laser device alone or together with at least one optical fiber for guiding light outputted from the laser device to the tissue area.

4. The method according to claim 1, wherein the noble metal nanoparticles are gold nanoparticles selected from gold nanorods or gold nanospheres.

5. The method for detection of cancer according to claim 4, wherein said gold nanoparticles are conjugated to targeting moieties that specifically home the golden nanoparticles to the cancerous tissue.

6. The method according to claim 5 for the detection of epidermal growth factor receptor (EGFR) expressing cancer, comprising the steps:
    (i) administering to an individual suspected of having EFGR expressing cancer a composition of gold nanorods (GNRs) conjugated to anti-EGFR antibodies;
    (ii) optically irradiating said area with a light source outputting an optical signal of wavelength 650 nm or 780 nm;
    (iii) measuring diffusion reflection of said tissue area; whereby
    detection from the measured diffusion reflection of accumulation of the conjugated GNRs in said area indicates that the irradiated tissue is a cancerous tissue of a EGFR-expressing cancer.

7. The method according to claim 6, wherein said EGFR-expressing cancer is melanoma or head and neck squamous cell carcinoma.

8. The method detection of cancer according to claim 5, further comprising measuring the concentration of the conjugated gold nanoparticles in the irradiated tissue, based on calculation of red-shift of the reflected light caused by surface plasmon resonance of the conjugated gold nanoparticles.

9. The method according to claim 1, wherein the noble metal nanoparticles are gold nanoparticle and said at least one wavelength in step b) is in the range of 500-900 nm.

10. The method for detection of arterial vascular disorders according to claim 9, wherein said gold nanoparticles are up taken by macrophages and other phagocytic cells present in injured vascular tissue.

11. The method according to claim 10, wherein said arterial vascular disorder is atherosclerotic vascular disease and said injured vascular tissue is inflammatory active atherosclerotic plaque.

12. A non-invasive and real time optical system based on diffusion reflection measurements for detection of arterial vascular disorders or cancer, said system comprising:
    a) an optical light source setup for irradiating an area of a tissue suspected of being a cancerous or injured vascular tissue of an individual to whom a composition of noble metal nanoparticles that accumulate in an injured vascular or cancerous tissue has been administered, said optical light source comprising a device configured for outputting an optical signal of at least one wavelength;
    b) at least one detector configured for detecting light reflected from the area of said irradiated tissue; and
    c) a processing unit for receiving output data from said at least one detector in real time and processing thereof for measuring diffusion reflection of said irradiated tissue, whereby
    detection from the measured diffusion reflection of accumulation of the noble metal nanoparticles in said area indicates that the irradiated tissue is an injured vascular or cancerous tissue.

13. The system according to claim 12, wherein said optical source setup and/or said at least one detector is configured for changing location thereof for measuring reflected light for various source-detector separations, defined as different distances between the light source and the at least one detector, wherein measuring of the diffusion reflection is carried out by detecting the changes in intensities of the irradiated tissue for different source-detector separations.

14. The system according to claim 13, wherein said detector or at least part of said optical source setup is configured for being moved at predefined distance intervals for changing the source-detector separation.

15. The system according to claim 12 further comprising multiple optical detectors and/or multiple optical fibers for guiding the output light from the laser device to multiple locations, for allowing simultaneous detection of reflected light for multiple source-detector separations for the diffusion reflection measuring.

16. The system according to claim 12, wherein said detector and/or said optical source setup is configured for continuous measuring of spatial reflectance from said irradiated area.

17. The system according to claim 12, wherein said optical source setup further comprises at least one optical fiber for guiding light outputted by the laser device to said area, and said optical source setup comprises at least one micrometer plate attached to a distal edge of said at least one optical fiber.

18. The system according to claim 12, wherein said system further comprises a signal collecting unit for collecting output signals from said at least one detector and outputting signal related data, said signal collecting unit is configured to transmit the signal related data to said processing unit in real time or near real time via at least one communication link.

19. The system according to claim 18, wherein said signal collecting unit is an oscilloscope, a central processing unit (CPU) communicating with said processing unit or a software program operable through said processing unit capable of receiving input data from said at least one detector through hardware of said processing unit.

20. The system according to claim 12, wherein said optical source setup comprises at least one laser diode outputting an optical signal of a narrow wavelength bandwidth.

21. The system according to claim 12, wherein said at least one detector is further configured for detecting frequency spectral data of the optical signal reflected from said tissue and said processing unit processes the received spectral data for measuring the concentration of the noble metal nanoparticles in the irradiated tissue, based on calculation of red-shift of the reflected light caused by surface plasmon resonance of the noble metal nanoparticles.

* * * * *